(12) United States Patent
Henley et al.

(10) Patent No.: US 8,328,788 B2
(45) Date of Patent: *Dec. 11, 2012

(54) METHODS AND SYSTEMS FOR ELECTROKINETIC DELIVERY OF A SUBSTANCE

(75) Inventors: Julian L. Henley, New Haven, CT (US); Kuo Wei Chang, Waltham, MA (US); Joseph Potter, Oak Bluffs, MA (US); Dennis I. Goldberg, South Brookline, MA (US); James Derouin, Taunton, MA (US)

(73) Assignee: Nitric Biotherapeutics, Inc., Bristol, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/105,630

(22) Filed: May 11, 2011

(65) Prior Publication Data

US 2011/0213295 A1    Sep. 1, 2011

Related U.S. Application Data

(60) Continuation of application No. 11/373,301, filed on Mar. 13, 2006, which is a division of application No. 10/724,160, filed on Dec. 1, 2003, now Pat. No. 7,016,724, which is a division of application No. 10/117,346, filed on Apr. 8, 2002, now Pat. No. 6,792,306, which is a continuation-in-part of application No. 09/584,138, filed on May 31, 2000, now Pat. No. 6,477,410, and a continuation-in-part of application No. 09/523,217, filed on Mar. 10, 2000, now Pat. No. 6,553,253.

(60) Provisional application No. 60/123,934, filed on Mar. 12, 1999.

(51) Int. Cl.
*A61N 1/30* (2006.01)

(52) U.S. Cl. .......................................... 604/501; 604/20
(58) Field of Classification Search .................. 604/501, 604/20, 22, 19, 289, 500; 607/15, 115, 120, 607/149, 152; 601/1, 2; 206/368, 369; 15/104.94
See application file for complete search history.

(56) References Cited

U.S. PATENT DOCUMENTS 206,474 A      7/1878   Morel
(Continued)

FOREIGN PATENT DOCUMENTS

AT    OE 0232642    3/1964
(Continued)

OTHER PUBLICATIONS

Henley et al., "Iontophoretic treatment of oral herpes." 1984, Laryngoscope 94(1):118-121.
(Continued)

*Primary Examiner* — Kevin C Sirmons
*Assistant Examiner* — Michael J Anderson
(74) *Attorney, Agent, or Firm* — Riverside Law LLP

(57) ABSTRACT

A method for delivering a substance to an infected nail of an individual is described. The method includes the step of applying a device to at least one infected nail of an individual, where the device includes at least one active electrode and at least one counter electrode, where the at least one counter electrode is in contact with the individual, and where the device is connected to at least one power source. The method also includes the steps of disposing a medicament between the at least one active electrode and the at least one infected nail, applying a salt solution to the at least one infected nail, and providing an electrical current from the power source to the at least one active electrode to facilitate delivery of the medicament into the region of the at least one infected nail.

19 Claims, 38 Drawing Sheets

U.S. PATENT DOCUMENTS

| | | | |
|---|---|---|---|
| 279,524 A | 6/1883 | Beaty | |
| 484,522 A | 10/1892 | McBride | |
| 600,290 A | 3/1898 | Muir | |
| 887,482 A | 5/1908 | Lammers | |
| 1,626,617 A | 5/1927 | Last | |
| 1,715,027 A | 5/1929 | Benjamin | |
| 1,786,541 A | 12/1930 | Last | |
| 1,967,927 A | 7/1934 | Deustch | |
| 2,047,308 A | 7/1936 | Chapman | |
| 2,078,391 A | 4/1937 | Last | |
| 2,123,980 A | 7/1938 | Warwick | |
| 2,126,070 A | 8/1938 | Wappler | |
| 2,151,458 A | 3/1939 | Allen | |
| 2,433,233 A | 12/1947 | Meminger | |
| 2,635,175 A | 4/1953 | Hodge | |
| 2,834,344 A | 5/1958 | Kanai | |
| 3,019,787 A | 2/1962 | Simmons | |
| 3,048,170 A | 8/1962 | Lemos | |
| 3,107,672 A | 10/1963 | Hofmann | |
| 3,163,166 A | 12/1964 | Brant et al. | |
| 3,279,468 A | 10/1966 | Le Vine | |
| 3,298,368 A | 1/1967 | Charos | |
| 3,447,537 A | 6/1969 | King | |
| 3,520,297 A | 7/1970 | Bechtold | |
| 3,556,105 A | 1/1971 | Shepard | |
| 3,645,260 A | 2/1972 | Cinotti et al. | |
| 3,716,054 A | 2/1973 | Porter et al. | |
| 3,831,598 A | 8/1974 | Tice | |
| 3,848,600 A | 11/1974 | Patrick, Jr. et al. | |
| 3,964,477 A * | 6/1976 | Ellis et al. | 604/20 |
| 3,971,387 A | 7/1976 | Mantell | |
| 4,116,238 A | 9/1978 | Pettijohn | |
| 4,126,937 A * | 11/1978 | Ellis et al. | 433/228.1 |
| 4,166,457 A | 9/1979 | Jacobsen et al. | |
| 4,211,222 A | 7/1980 | Tapper | |
| 4,292,968 A | 10/1981 | Ellis | |
| 4,301,794 A | 11/1981 | Tapper | |
| 4,325,367 A | 4/1982 | Tapper | |
| 4,383,529 A | 5/1983 | Webster | |
| 4,393,884 A | 7/1983 | Jacobs | |
| 4,406,658 A | 9/1983 | Lattin et al. | |
| 4,416,274 A | 11/1983 | Jacobsen et al. | |
| 4,429,703 A | 2/1984 | Haber | |
| 4,474,570 A | 10/1984 | Ariura et al. | |
| 4,510,939 A | 4/1985 | Brenman et al. | |
| 4,528,265 A * | 7/1985 | Becker | 424/654 |
| 4,639,244 A | 1/1987 | Rizk et al. | |
| 4,655,229 A | 4/1987 | Sensabaugh, Jr. et al. | |
| 4,665,921 A | 5/1987 | Teranishi et al. | |
| 4,689,039 A | 8/1987 | Masaki | |
| 4,702,732 A | 10/1987 | Powers et al. | |
| 4,708,716 A | 11/1987 | Sibalis | |
| 4,725,263 A * | 2/1988 | McNichols et al. | 604/20 |
| 4,735,217 A | 4/1988 | Gerth et al. | |
| 4,747,819 A * | 5/1988 | Phipps et al. | 604/20 |
| 4,756,318 A | 7/1988 | Clearman et al. | |
| 4,763,660 A | 8/1988 | Kroll et al. | |
| 4,764,164 A | 8/1988 | Sasaki | |
| 4,767,402 A | 8/1988 | Kost et al. | |
| 4,771,796 A | 9/1988 | Myer | |
| 4,776,353 A | 10/1988 | Lilja et al. | |
| 4,786,278 A | 11/1988 | Masaki | |
| 4,787,888 A | 11/1988 | Fox | |
| 4,793,366 A | 12/1988 | Hill | |
| 4,800,903 A | 1/1989 | Ray et al. | |
| 4,808,152 A | 2/1989 | Sibalis | |
| 4,813,437 A | 3/1989 | Ray | |
| 4,820,263 A | 4/1989 | Spevak et al. | |
| 4,821,740 A | 4/1989 | Tachibana et al. | |
| 4,838,273 A | 6/1989 | Cartmell | |
| 4,865,582 A | 9/1989 | Sibalis | |
| 4,907,606 A | 3/1990 | Lilja et al. | |
| 4,913,148 A | 4/1990 | Diethelm | |
| 4,917,119 A | 4/1990 | Potter et al. | |
| 4,919,648 A | 4/1990 | Sibalis | |
| 4,922,901 A | 5/1990 | Brooks et al. | |
| 4,931,046 A | 6/1990 | Newman | |
| 4,942,883 A | 7/1990 | Newman | |
| 4,950,229 A | 8/1990 | Sage, Jr. | |
| 4,953,565 A | 9/1990 | Tachibana et al. | |
| 4,957,480 A | 9/1990 | Morenings | |
| 4,979,938 A | 12/1990 | Stephen et al. | |
| 4,997,418 A | 3/1991 | DeMartini | |
| 5,002,527 A | 3/1991 | Reller et al. | |
| 5,006,108 A | 4/1991 | LaPrade | |
| 5,019,034 A | 5/1991 | Weaver et al. | |
| 5,037,381 A | 8/1991 | Bock et al. | |
| 5,042,975 A | 8/1991 | Chien et al. | |
| 5,047,007 A | 9/1991 | McNichols et al. | |
| 5,053,001 A | 10/1991 | Reller et al. | |
| 5,060,671 A | 10/1991 | Counts et al. | |
| 5,090,402 A | 2/1992 | Bazin et al. | |
| 5,115,805 A | 5/1992 | Bommannan et al. | |
| 5,133,352 A | 7/1992 | Lathrop et al. | |
| 5,135,478 A | 8/1992 | Sibalis | |
| 5,135,479 A | 8/1992 | Sibalis et al. | |
| 5,147,291 A | 9/1992 | Cukier | |
| 5,160,316 A | 11/1992 | Henley | |
| 5,162,042 A | 11/1992 | Gyory et al. | |
| 5,167,242 A | 12/1992 | Turner et al. | |
| 5,169,384 A | 12/1992 | Bosniak et al. | |
| 5,171,215 A | 12/1992 | Flanagan | |
| 5,203,768 A | 4/1993 | Haak et al. | |
| 5,236,413 A * | 8/1993 | Feiring | 604/21 |
| 5,250,022 A | 10/1993 | Chien et al. | |
| 5,254,081 A | 10/1993 | Maurer et al. | |
| 5,279,543 A | 1/1994 | Glikfeld et al. | |
| 5,284,471 A | 2/1994 | Sage, Jr. | |
| 5,298,017 A | 3/1994 | Theeuwes et al. | |
| 5,310,404 A | 5/1994 | Gyory et al. | |
| 5,312,326 A | 5/1994 | Myers et al. | |
| 5,314,502 A | 5/1994 | McNichols et al. | |
| 5,320,597 A * | 6/1994 | Sage et al. | 604/20 |
| 5,320,598 A * | 6/1994 | Haak et al. | 604/20 |
| 5,331,979 A | 7/1994 | Henley | |
| 5,354,321 A | 10/1994 | Berger | |
| 5,360,440 A | 11/1994 | Andersen | |
| 5,362,307 A | 11/1994 | Guy et al. | |
| 5,362,308 A | 11/1994 | Chien et al. | |
| 5,374,241 A | 12/1994 | Lloyd et al. | |
| 5,374,242 A | 12/1994 | Haak et al. | |
| 5,374,283 A * | 12/1994 | Flick | 607/46 |
| 5,376,107 A | 12/1994 | Inagi et al. | |
| 5,391,195 A | 2/1995 | Van Groningen | |
| 5,395,310 A | 3/1995 | Untereker et al. | |
| 5,413,590 A | 5/1995 | Williamson | |
| 5,415,629 A | 5/1995 | Henley | |
| 5,421,816 A | 6/1995 | Lipkovker | |
| 5,441,936 A | 8/1995 | Houghten et al. | |
| 5,443,441 A | 8/1995 | De Claviere | |
| 5,458,569 A | 10/1995 | Kirk, III et al. | |
| 5,464,387 A | 11/1995 | Haak et al. | |
| 5,466,217 A | 11/1995 | Myers et al. | |
| 5,470,349 A | 11/1995 | Kleditsch et al. | |
| 5,494,679 A | 2/1996 | Sage, Jr. et al. | |
| 5,501,705 A | 3/1996 | Fakhri | |
| 5,514,167 A | 5/1996 | Smith et al. | |
| 5,527,357 A | 6/1996 | Springer | |
| 5,538,503 A | 7/1996 | Henley | |
| 5,540,669 A | 7/1996 | Sage, Jr. et al. | |
| 5,551,953 A | 9/1996 | Lattin et al. | |
| 5,558,632 A | 9/1996 | Lloyd et al. | |
| 5,562,607 A | 10/1996 | Gyory | |
| 5,589,563 A | 12/1996 | Ward et al. | |
| 5,591,123 A | 1/1997 | Sibalis et al. | |
| 5,603,693 A | 2/1997 | Frenkel et al. | |
| 5,607,461 A | 3/1997 | Lathrop | |
| 5,607,691 A | 3/1997 | Hale et al. | |
| 5,618,275 A | 4/1997 | Bock | |
| 5,658,247 A | 8/1997 | Henley | |
| 5,667,487 A | 9/1997 | Henley | |
| 5,668,170 A | 9/1997 | Gyory | |
| 5,676,648 A | 10/1997 | Henley | |
| 5,678,273 A | 10/1997 | Porcelli | |
| 5,688,233 A | 11/1997 | Hofmann et al. | |
| 5,697,896 A | 12/1997 | McNichols et al. | |
| 5,700,457 A | 12/1997 | Dixon | |

| | | |
|---|---|---|
| 5,711,761 A | 1/1998 | Untereker et al. |
| 5,713,846 A | 2/1998 | Bernhard et al. |
| 5,720,773 A | 2/1998 | Lopez-Claros |
| 5,722,397 A | 3/1998 | Eppstein |
| 5,722,404 A * | 3/1998 | Lundback ............ 600/387 |
| 5,725,817 A | 3/1998 | Milder |
| 5,733,255 A | 3/1998 | Dinh et al. |
| 5,755,750 A | 5/1998 | Petruska et al. |
| 5,788,666 A | 8/1998 | Atanasoska |
| 5,794,774 A | 8/1998 | Porcelli |
| 5,795,321 A | 8/1998 | McArthur et al. |
| 5,797,867 A | 8/1998 | Guerrera et al. |
| 5,830,175 A | 11/1998 | Flower |
| 5,840,057 A | 11/1998 | Aloisi |
| 5,846,217 A | 12/1998 | Beck et al. |
| 5,865,786 A | 2/1999 | Sibalis et al. |
| 5,879,323 A | 3/1999 | Henley |
| 5,882,676 A | 3/1999 | Lee et al. |
| 5,899,875 A | 5/1999 | Millot |
| 5,899,876 A | 5/1999 | Flower |
| 5,908,401 A | 6/1999 | Henley |
| 5,911,319 A | 6/1999 | Porcelli et al. |
| 5,913,883 A | 6/1999 | Alexander et al. |
| 5,919,155 A * | 7/1999 | Lattin et al. ............ 604/20 |
| 5,931,859 A | 8/1999 | Burke |
| 5,935,598 A | 8/1999 | Sage et al. |
| 5,954,684 A | 9/1999 | Flower et al. |
| 5,961,482 A | 10/1999 | Chien et al. |
| 5,961,483 A | 10/1999 | Sage et al. |
| 5,968,005 A | 10/1999 | Tu |
| 5,968,006 A | 10/1999 | Hofmann |
| 5,983,130 A | 11/1999 | Phipps et al. |
| 6,001,088 A | 12/1999 | Roberts et al. |
| 6,004,309 A | 12/1999 | Phipps |
| 6,004,547 A | 12/1999 | Rowe et al. |
| 6,006,130 A | 12/1999 | Higo et al. |
| 6,018,679 A | 1/2000 | Dinh et al. |
| 6,023,639 A | 2/2000 | Hakky et al. |
| 6,032,073 A | 2/2000 | Effenhauser |
| 6,038,485 A | 3/2000 | Axelgaard |
| 6,041,252 A | 3/2000 | Walker et al. |
| 6,041,253 A | 3/2000 | Kost et al. |
| 6,048,545 A | 4/2000 | Keller et al. |
| 6,057,374 A | 5/2000 | Huntington et al. |
| 6,078,842 A | 6/2000 | Gross et al. |
| 6,101,411 A | 8/2000 | Newsome |
| 6,104,950 A | 8/2000 | Higo et al. |
| 6,119,036 A | 9/2000 | Allen |
| 6,141,582 A | 10/2000 | Mori et al. |
| 6,148,231 A | 11/2000 | Henley |
| 6,148,232 A | 11/2000 | Avrahami |
| 6,167,302 A | 12/2000 | Millot |
| 6,267,736 B1 | 7/2001 | McCambridge et al. |
| 6,283,938 B1 | 9/2001 | McConnell |
| 6,293,900 B1 | 9/2001 | Bove et al. |
| 6,375,990 B1 | 4/2002 | Nemeroff et al. |
| 6,385,487 B1 | 5/2002 | Henley |
| 6,393,318 B1 | 5/2002 | Conn et al. |
| RE37,796 E | 7/2002 | Henley |
| 6,477,410 B1 | 11/2002 | Henley et al. |
| 6,490,482 B2 | 12/2002 | Mori et al. |
| RE38,000 E | 2/2003 | Henley |
| 6,553,253 B1 | 4/2003 | Chang |
| 6,560,482 B1 | 5/2003 | Parienti |
| 6,567,693 B1 | 5/2003 | Allen |
| 6,597,946 B2 | 7/2003 | Avrahami et al. |
| 6,611,706 B2 | 8/2003 | Avrahami et al. |
| 6,615,079 B1 | 9/2003 | Avrahami |
| 6,650,934 B2 | 11/2003 | Murdock |
| RE38,341 E | 12/2003 | Henley |
| 6,708,060 B1 | 3/2004 | Avrahami et al. |
| 6,711,435 B2 | 3/2004 | Avrahami |
| 6,735,470 B2 | 5/2004 | Henley et al. |
| 6,775,569 B2 | 8/2004 | Mori et al. |
| 6,792,306 B2 | 9/2004 | Henley et al. |
| 7,016,724 B2 | 3/2006 | Henley et al. |
| 7,069,073 B2 | 6/2006 | Henley et al. |
| 7,127,285 B2 | 10/2006 | Henley et al. |
| 7,164,942 B2 | 1/2007 | Avrahami et al. |
| 2002/0016562 A1 | 2/2002 | Cormier et al. |
| 2002/0042587 A1 | 4/2002 | Murdock |
| 2002/0055704 A1 | 5/2002 | Scott et al. |
| 2002/0161324 A1 | 10/2002 | Henley et al. |
| 2004/0013623 A1 | 1/2004 | Tolkoff et al. |
| 2004/0111051 A1 | 6/2004 | Henley et al. |
| 2006/0138583 A1 | 6/2006 | Henley |
| 2006/0167403 A1 | 7/2006 | Henley et al. |
| 2006/0276741 A1 | 12/2006 | Henley |

FOREIGN PATENT DOCUMENTS

| | | |
|---|---|---|
| EP | 0230749 | 8/1987 |
| EP | 039093 A1 | 3/1989 |
| EP | 617979 A1 | 10/1994 |
| FR | 1445703 | 6/1966 |
| FR | 2513129 | 3/1983 |
| GB | 0299553 | 11/1928 |
| JP | 3-170172 | 7/1991 |
| SU | 654254 | 3/1979 |
| SU | 931191 | 5/1982 |
| SU | 1003853 | 3/1983 |
| WO | WO 86/07269 | 12/1986 |
| WO | WO 90/06153 | 6/1990 |
| WO | WO 90/08571 | 8/1990 |
| WO | WO 93/03790 | 3/1993 |

OTHER PUBLICATIONS

Gangarosa et al., "Iontophoretic application of idoxuridine for recurrent herpes labialis: report of preliminary clinical trials," 1979, Methods Find Exp Clin Pharmacol. 1(2):105-109.

Gangarosa et al., "Iontophoresis of vidarabine monophosphate for herpes orolabialis." 1986, J Infect Dis 154(6):930-934.

Spruance et al., "The Natural History of Recurrent Herpes Simplex Labialis." 1977, N Engl J Med 297(2):69-75.

Nahmias et al., "Infection with Herpes-Simplex Viruses 1 and 2." 1973, N Engl J Med 289(13):667-674.

Comeau et al., "Anesthesia of the human tympanic membrane by iontophoresis of a local anesthetic." 1978, The Laryngoscope 88(2 Pt. 1):277-285.

Waud, "Iontophoretic application of drugs." 1967 J Appl Physiol 23(1):128-130.

LaForest et al., "Antibiotic iontophoresis in the treatment of ear chondritis." 1978 Physical Therapy 58(1):32-34.

Glass et al., "The quantity and distribution of radiolabeled dexamethasone delivered to tissue by iontophoresis." 1980 International Journal of Dermatology 19:519-525.

Hill et al., "Iontophoretic application of antiviral chemotherapeutic agents." 1977, Ann N Y Acad Sci. 284:604-12.

Hill, et al., "Ocular iontophoresis." 1993. in A. K. Mitra (ed.), Ophthalmic drug delivery systems. Marcel Dekker, Inc., New York. p. 331-354.

Park et al., "tophoretic application of adenine arabinoside monophosphate to herpes simplex virus type 1-infected hairless mouse skin," 1978, Antimicrob Agents Chemother 14(4):605-608.

Costello et al., "Iontophoresis: applications in transdermal medication delivery." 1995, Physical Therapy 75(6):554-63.

Kassan et al., "Physical enhancement of dermatologic drug delivery: iontophoresis and phonophoresis." 1996, J Am Acad Dermatol. 34(4):657-66.

Boxhall et al., "Iontophoresis and herpes labialis." 1984, Med J Aust.140(11):686-7.

Rapperport et al., "Iontophoresis. A method of antibiotic administration in the burn patient." 1965, Plastic and Reconstructive Surgery 36(5):547-552.

Gangarosa et al., "Iontophoresis for enhancing penetration of dermatologic and antiviral drugs." 1995, Journal of Dermatology 22(11):865-875.

Gangarosa et al., "Iontophoretic treatment of herpetic whitlow." 1989, Arch Phys Med Rehabil 70:336-340.

Gangarosa et al., "Iontophoretic Application of Antiviral Drugs," Proceedings of an International Symposium held in Tokushima City, Japan pp. 201-204; Jul. 27-30, 1981.

Gangarosa, "Iontophoretic application of adenine arabinoside monophosphate for the treatment of herpes simplex virus type 2 skin infections in hairless mice." 1979 Journal of Infectious Diseases 140(6)1014.

Kwon et al., "Effect of iontophoretic and topical application of antiviral agents in treatment of experimental HSV-1 keratitis in rabbits." 1979, Investigative Ophthalmology and Visual Science 18(9):984-988.

Hill et al., "Acyclovir and vidarabine monophosphate: Comparison of Iontophoretic and intravenous administration for the treatment of HSV-1 stromal keratitis." The American Journal of Medicine, Acyclovir Symposium, vol. 73, Issue 1, Part 1 , pp. 300-304, Jul. 20, 1982.

Hill et al., "Thymine arabinoside (Ara-T) topical and iontophoretic application for herpes simplex virus type 1 and type 2 skin infections in hairless mice." 1984, Meth and Find Exptl Clin Pharmacol 6(1):17-20.

Volpato et al., "Iontophoresis enhances the transport of acyclovir through nude mouse skin by electrorepulsion and electroosmosis." 1995, Pharmaceutical Research 12(11):1623-1627.

Spruance et al., "Early application of topical 15% idoxuridine in dimethyl sulfoxide shortens the course of herpes simplex labialis: a multicenter placebo-controlled trial." 1990, The Journal of Infectious Diseases 161:191-197.

Gangarosa, "Iontophoresis for surface local anesthesia," 1974, J Am Dent Assoc. 88:125-128.

Gangarosa et al., "Conductivity of drugs used for iontophoresis." 1978, Journal of Pharmaceutical Sciences 67(10):1439-1443.

Chang et al., "A pilot study of iontophoretic cisplatin chemotherapy of basal and squamous cell carcinomas of the skin." 1993, Arch Dermatol 129:425-427.

Gangarosa et al., "How Modern Iontophoresis Can Improve Your Practice." 1982, (Quintessence International) Oral Surgery No. 10, Report 2135, Oct. 1982, pp. 1027-1038.

Baron et al., "Postherpetic neuralgia. Are C-nociceptors involved in signalling and maintenance of tactile allodynia?" 1993, Brain 116:1477-1496.

Gangarosa et al., "Iontophoretic assistance of 5-Iodo-2'-deoxyuridine penetration into neonatal mouse skin and effects on DNA synthesis." 1977 Proc Soo Exp Biol Med. 154(3):439-43.

Kamath et al., "Electrophoretic evaluation of the mobility of drugs suitable for iontophoresis." 1995, Meth Find Exp Clin Pharmacol 17(4):227-232.

Singh et al., "Transdermal drug delivery by passive diffusion and iontophoresis: a review." 1993, Medicinal Research Reviews 13(5):569-621.

Guy et al., "Iontophoresis: electrorepulsion and electroosmosis" 2000, Journal of Controlled Release 64:129-132.

Emmert, "Treatment of common cutaneous herpes simplex virus infections." 2000, American Family Physician 61(6):1697-1704.

Kantaria et al., "Gleatin-stabilised Microemulsion-Based Oranogels: Rheology and Application in Iontophoretic Transdermal Drug Delivery." 1999, Journal of Controlled Release 60:355-365.

Merino et al., "Electrorepulsion versus electroosmosis: effect of pH on the iontophoretic flux of 5-fluorouracil." 1999, Phamaceutical Research 16(6).

Breathnach, "Azelaic acid: potential as a general antitumoural agent." 1999, Medical Hypotheses 52(3):221-226.

Javaly et al., "Treatment of mucocutaneous herpes simplex virus infections unresponsive to acyclovir with topical foscarnet cream in AIDS patients: a phase I/II study." 1999, Journal of Acquired Immune Deficiency Syndromes 21:301-306.

Spellman et al., "Efficacy and safety of azelaic acid and glycolic acid combination therapy compared with tretinoin therapy for acne." 1998, Clinical Therapeutics 20(4):711-721.

Park et al., "Passive versus electrotransport-facilitated transdermal absorption of ketorolac." 1998, Clinical Pharmacology and Therapeutics 63(3):303-315.

Gnann et al., "Sorivudine versus acyclovir for treatment of dermatomal herpes zoster in human immunodeficiency virus-infected patients: results from a randomized, controlled clinical trial. Collaborative Antiviral Study Group/AIDS Clinical Trials Group, Herpes Zoster Study Group." 1998, Antimicrobial Agents and Chemotherapy 42(5):1139-1145.

Gibson, "Azelaic acid 20% cream (AZELEX) and the medical management of acne vulgaris." 1997, Dermatology Nursing 9(5):339-344.

Whitley "Sorivudine: a promising drug for the treatment of varicella-zoster virus infection." 1995, Neurology 45(Supp 8):S73-S75.

Machida et al., "Antiherpesviral and anticellular effects of 1-beta-D-arabinofuranosyl-E-5-(2-halogenovinyl) uracils." 1981, Antimicrobial Agents and Chemotherapy 20(1):47-52.

"Herpes Simplex," American Academy of Dermatology, 1987, Revised 1991, 1993.

Haney, 2000, "Common Cold Virus is Near," The Associated Press, Jan. 15, 2000.

Hemphill, "New Medicines Move to Eradicate Acne." The New York Times, Feb. 29, 2000.

"Warts." American Academy of Dermatology, 1997, Revised 1991, 1993.

"Psoriasis." American Academy of Dermatology 1994.

"Eczema/Atopic Dermatitis." American Academy of Dermatology, 1987, revised 1991, 1993, 1995.

"Skin Cancer: An Undeclared Epidemic." American Academy of Dermatology, 1988, Revised 1989, 1993, 1994.

Gröning "Electrophoretically Controlled Dermal or Transdermal Application Systems with Electronic Indicators." 1987, International Journal of Pharmaceutics 36:37-40.

\* cited by examiner

Fig. 27
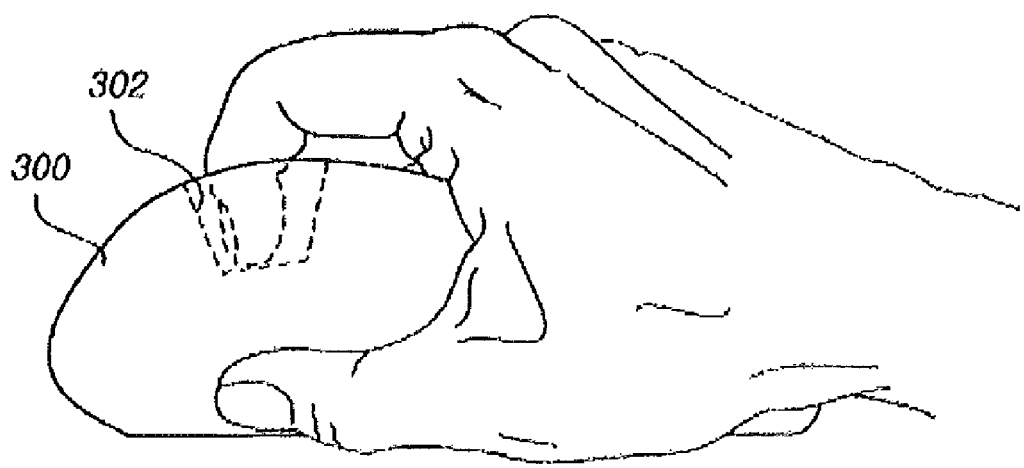
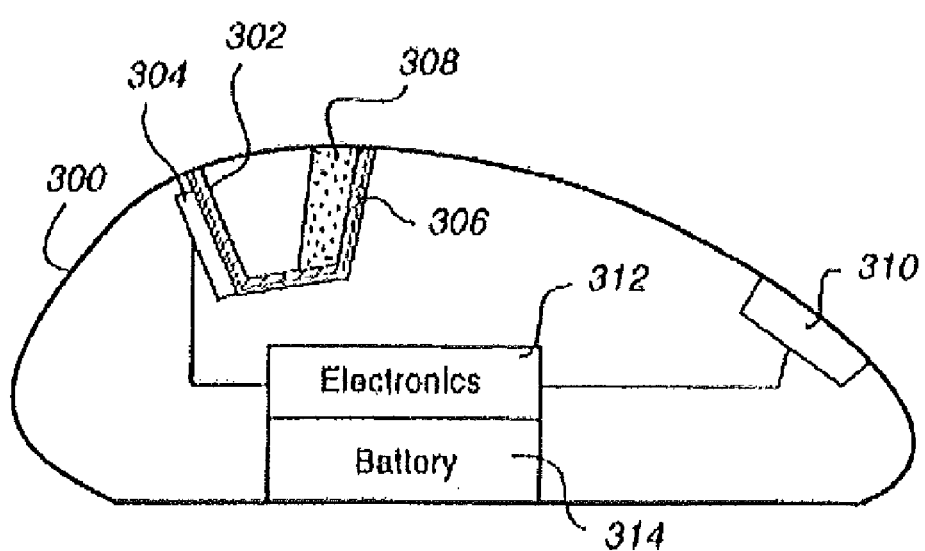
Fig. 28

Source Risk-Current Limits

METHODS AND SYSTEMS FOR ELECTROKINETIC DELIVERY OF A SUBSTANCE

CROSS REFERENCE TO RELATED APPLICATIONS

The present application is a continuation of U.S. patent application Ser. No. 11/373,301, filed Mar. 13, 2006, which is a division of U.S. patent application Ser. No. 10/724,160, filed Dec. 1, 2003, now U.S. Pat. No. 7,016,724, which is a division of U.S. patent application Ser. No. 10/117,346, filed on Apr. 8, 2002, now U.S. Pat. No. 6,792,306, which is a continuation-in-part of both U.S. patent application Ser. No. 09/584,138, filed on May 31, 2000, now U.S. Pat. No. 6,477,410, and of U.S. patent application Ser. No. 09/523,217, filed Mar. 10, 2000, now U.S. Pat. No. 6,553,253, which claims priority from U.S. Provisional Application No. 60/123,934, filed Mar. 12, 1999, all of which are incorporated by reference herein as if each is being set forth herein in its entirety.

BACKGROUND OF THE INVENTION

Electrokinetic delivery of medicaments for applying medication locally through an individual's skin is known. One type of electrokinetic delivery mechanism is iontophoresis, i.e., the application of an electric field to the skin to enhance the skin's permeability and to deliver various ionic agents, e.g., ions of soluble salts or other drugs. In certain situations, iontophoretic transdermal or transmucocutaneous delivery techniques have obviated the need for hypodermic injection for many medicaments, thereby eliminating the concomitant problem of trauma, pain and risk of infection to the individual. Other types of electrokinetic delivery mechanisms include electroosmosis, electroporation, electromigration, electrophoresis and endosmose, any or all of which are generally known as electrotransport, electromolecular transport or iontophoretic methods. The electrokinetic delivery mechanism may also be accompanied by ultrasonic vibration to further facilitate electrokinetic transport of the substance, e.g., by opening pores in the skin. Ultrasound may be employed in a number of ways such as (i) traditional piezoelectric elements, (ii) Application Specific Integrated Circuits (ASIC) with ultrasound transmitter built in or (iii) by thin foil sheets with incorporated piezoelectric dipole elements.

There are several difficulties with electrokinetic delivery of substances such as medicaments. One is the heretofore need for somewhat cumbersome, bulky and costly equipment which oftentimes requires the presence of an individual at a doctor's office or treatment center and use of medical professionals to administer the medicament. Private, self-administration of medicaments or for diagnostic application by the individual at non-medical or non-professional facilities is highly desirable. Also, an easily transportable apparatus for electrokinetic delivery of medication, for example, a lightweight, compact portable device useful with an applicator packaged as a single or unit dosage applicator, appears ideal as a patient/consumer friendly self-administration system appropriate for many circumstances.

BRIEF SUMMARY OF THE INVENTION

The present invention relates to a method for delivering a substance to an infected nail of an individual. The method includes the step of applying a device to at least one infected nail of an individual, where the device includes at least one active electrode and at least one counter electrode, where the at least one counter electrode is in contact with the individual, and where the device is connected to at least one power source. The method also includes the steps of disposing a medicament between the at least one active electrode and the at least one infected nail, applying a salt solution to the at least one infected nail, and providing an electrical current from the power source to the at least one active electrode to facilitate delivery of the medicament into the region of the at least one infected nail.

In one embodiment, the application of the salt solution occurs prior to delivery of the medicament. In another embodiment, the medicament is an anti-fungal. In another embodiment, the medicament is contained within a pad. In another embodiment, the medicament comprises a conductive fluid. In another embodiment, the nail is a toenail. In another embodiment, the medicament is delivered directly into the nail bed. In another embodiment, the medicament is delivered into the nail bed and surrounding nail tissue.

The present invention also relates to a system for delivering a substance to an infected nail of an individual. The system includes a power source, a device connected to the power source, where the device includes at least one active electrode and at least one counter electrode, where the at least one counter electrode is in contact with the individual, a medicament disposed between the at least one active electrode of the device and the infected nail of the individual, where the infected nail is first treated with a salt solution, and subsequently an electrical current is provided from the power source to the at least one active electrode to electrokinetically drive the medicament into the salt-treated region of the infected nail.

Further, the present invention relates to a device for delivery of a substance to a treatment site on an individual. The device includes a power supply, an applicator including a first electrode and a pad for containing a substance, where the first electrode is connected to the power supply and the pad is positioned on a first side of the applicator with the first electrode overlying the pad, and a second electrode connected to the power supply. After application of a salt solution to the treatment site, the applicator is applied against the treatment site and the second electrode is placed in contact with a portion of the individual's body, and an electrical circuit is completed between the first electrode through the treatment site, the portion of the individual's body and the second electrode for electrokinetically driving the substance into the treatment site.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 27 is a schematic representation of a device for electrokinetically treating a fungal infestation of the nail beds of an individual's fingers;

FIG. 28 is a schematic illustration of the electronics and thimble pad applicator of the device of FIG. 27;

DETAILED DESCRIPTION OF THE INVENTION

Figure 1:
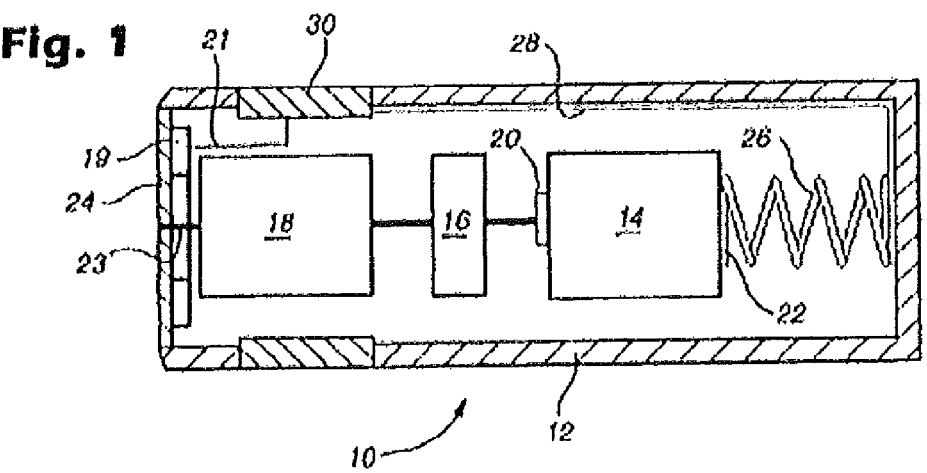
FIG. 1 is a schematic illustration of an electrokinetic medicament delivery device for use with an applicator in accordance with the present invention.

The invention relates to systems and methods for treating a fungal infection of the nail of an individual. In various embodiments, the methods include applying a device to at least one nail of the individual that is infected by a fungus. In various embodiments, the devices include at least one active electrode and at least one counter electrode, with the at least one counter electrode in contact with the individual.

A. Electrokinetic Delivery of Medicaments

In accordance with a preferred embodiment of the present invention, there is provided a portable, self-contained, hand-held lightweight, compact and wireless electrokinetic device for delivering or removing a substance, e.g., a medicament, and a unit dosage substance applicator for use with the device for the self-administration of a medicament to the skin. By the term substance is meant a medicament as well as natural or homeopathic products that may be outside the definition of medicament, e.g., inks and pigments for tattoos, and more generally includes any substance capable of electrokinetic transport through skin or mucocutaneous membrane, e.g., into a treatment site or from a site, e.g., for diagnostic purposes. The majority of applications using the present invention are for applying medicaments to treatment sites and therefore the term medicament is used in lieu of the term substance throughout this specification. By medicament is meant any chemical or biologic that may be used on or administered to humans or animals as an aid in the diagnosis, treatment or prevention of disease or other abnormal or cosmetic condition or for the relief of pain or to control, diagnose or improve any physiologic or pathologic condition.

Major therapeutic classes include but are not limited to, ACE inhibitors, such as ranitidine, anti-infectives such as antibacterials, antivirals and antimicrobials, vasodilators, including general, coronary, peripheral and cerebral, adrenocortical steroids, alpha-adrenergic agonists, alpha-adrenergic antagonists, selective alpha-two-adrenergic agonists, analgesics, and analgesic combinations, androgens, local and general anesthetics, antiaddictive agents, antiandrogens, antiarrhythmic agents, antiasthmatic agents, anticholinergic agents, anticholinesterase agents, xanthine derivatives, cardiovasculars including calcium channel blockers such as nifedipine, beta agonists such as dobutamine and ritodine, anticoagulants, including heparin, anticonvulsants, antidiabetic agents, antidiarrheal agents, antidiuretic, antiemetic and prokinetic agents, antiepileptic agents, antiestrogens, antihypertensives, such as atenolol, antimigraine agents, antimotionsickness preparations such as scopolamine, ondansetron, meclizine, antinausants, antimuscarinic agents, antiprurtics, antipsychotics, antipyretics, antispasmodics such as gastrointestinal and urinary, antineoplastic agents, antiparasitic agents, anti-Parkinson's agents, antiplatelet agents, antiprogestins, antithyroid agents, antitussives, atypical antidepressants, azaspirodecanediones, barbituates, benzodiazepines, benzothiadiazides, beta blockers, antiarrythmics beta-adrenergic agonists, beta-adrenergic antagonists, selective beta-one-adrenergic antagonists, selective beta-two-adreneric antagonists, bile salts, medicaments affecting volume and composition of body fluids, butyrophenones, agents affecting calcification, catecholamines and sympathomimetics, cholergic agonists, cholinesterase reactivators, dermatological medicaments, diphenylbutylpiperines, diuretics, ergot alkaloids, estrogens, ganglionic blocking agents, ganglionic stimulating agents, hydantoins, agents for control of gastric acidity, and treatment of peptic ulcers, hematopoitic agents, hisamines, histamine antagonists, 5-hydroxytryptamine antagonists, hyperlipoproteinemia medicaments, hypnotics and sedatives, tranquilizers, hormones, including pituitary hormones such as HGH, HMG, HCG, desmopressin acetate and the like; follicle luteolds, α-ANF, growth factor releasing factor (GFRF), β-MSH, somatostatin, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagons, hirulog, hyaluronidase, insulin like growth factors, m[a]enotropins (urofollitropin (FSH) and LH), oxytocin, streptokinase, tissue plasminogen activator, urokinase, ACTH analogs, ANP, ANP clearance inhibitors, angiotensin II antagonists, antidiuretic hormone agonists, antidiuretic hormone antagonists, bradykinin antagonists, CD4, ceredase, enkephalins, FAB fragments, IgE peptide suppressors, IGF-1, neurotrophic factors, colony stimulating factors, parathyroid hormone agonists, parathyroid hormone antagonists, pentigetide, protein C, protein S, rennin inhibitors, thymosin alpha-1, thrombolytics, TNF, vaccines, alpha-1 antitrypsin (recombinant), and TGF-beta, immunosuppressives, parasympatholytics, parasympathomimetics, psychostimulants, laxatives, methylxanthines, monomine oxidase inhibitors, neuromuscular blocking agents, organic nitrates, opoid analgesics and antagonists, pancreatic enzymes, phenothiazines, progestins, prostaglandins, e.g., alprostadil, agents for treatment of psychiatric disorders, sodium channel blockers, medicaments for spasticity and acute muscle spasms, e.g., muscle relaxants, succinimides, thioxanthines, thrombolytic agents, thyroid agents, tricyclic antidepressants, inhibitors of tubular transport of organic compounds, uterine motility affecting agents, and the like.

Representative medicaments, their analogs and derivatives thereof, included by way of example and not for purposes of limitation, are interferons, e.g., α-2b interferon, amphotericin β, angiopeptin, baclofen, bepridil, buserelin, buspirone, calcitonin, ciclopirox, olamine, copper, cyclosporin, zinc, tropisetron, vapreotide, vasopressin, vasopressin antagonist analogs, verapamil, warfarin, zacopride, zotasetron, cromolyn sodium, diltiazem, felodipine, isradipine, nicardipine, nifedipine, nimodipine, nitredipine, verapamil, isoproterenol, carterolol, labetalol, levobunolol, minoxidil, nadolol, penbuterol, pindolol, propranolol, sotalol, timolol, acebutolol, betaxolol, esmolol, metaprotenerol, pirbuterol, ritodrine, terbutaline, alclometasone, aldosterone, amcinonide, beclomethasone, dipropionate, betamethasone, clobetasol, clocortolone, cortisol, cortisone, corticosterone, desonide, desoximetasone, 11-desoxycortiosterone, 11-desoxycortisol, diflorasone, fludrocortisone, flunisolide, fluocinolone, fluocinonide, fluorometholone, flurandrenolide, G-CSF, GM-CSF, M-CSF, GHRF, GHRH, gonadorelin, goserlin, granisetron, halcinonide, hydrocortisone, indomethacin, insulin, insulinotropin, interleukins, e.g., interleukin-2, isosorbide dinitrate, leuprolide, lisinopril, LHRH, LHRH analogs such as buserlin and leuprolide, octreotide, endorphin, TRH, NT-36(-[[(s)-4-oxo-2-azetidinyl]carbonyl]-L-histidyl-L-prolinamide), liprecin, LMW heparin, i.e., enoxaparin, melatonin, medrysone, 6α-methylprednisolone, mometasone, paramethasone, prednisolone, prednisone, tetrahydrocortisol, trimcinolone, benoxinate, benzocaine, bupivacaine, chloroprocaine, dibucaine, dyclonine, etidocaine, mepivacaine, pramoxine, procaine, proparacaine, tetracaine, chloroform, cloned, cycloproane, desflurane, diethyl ether, droperidol, enflurane, etomidate, halothane, isoflurane, ketamine, hydrochloride, meperidine, methohexital, methoxylflurane, nitrogylcerine, propofol, scvoflurane, thiamyal, thiopental, acetaminophen, allopurinol, apazone, aspirin, auranofin, aurothioglucose, colchiine, diclofenac, diflunisal, etodolac, fenoprofen, flurbiprofen, gold sodium thiomalate, ibuprofen, indomethacin, ketoprofen, meclofenamate, mefenanic acid, mesalamine, methyl salicylate, nabumetone, naproxen, oxyphenbutazone, phenacetin, phenylbutazone, piroxicam, salicylamide, salicylate, salicylic acid, salsalate, sulfasalazine, sulindae, tometin, acetophenazine, chlorpromazine, fluphenazine, mesoridazine, perphenazine, thioridazine, triflurperazine, triflupromazine, disopyramide, encamide, flecinide, indecainide, mexiletine, moricizine, phenyloin, procainamide, propafenone, quinidine, tocaine, cisapride, domperdone, dronabinol, haloperidol, metoclopramide, nabilone, nicotine, prochlorperazine, promethazine, thiethylperazine, trimethobenzamide, buprenorphine, butorphanol, codeine, dezocine, diphenoxylate, drocode, doxazosin, hydrocodone, hydromorphone, levallorphan, levorphanol, lopermide, meptazinol, methadone, nalbuphine, nalmefene, naloxone, naltrexone, oxybutynin, oxycodone, oxymorphone, pentazocine, propoxyphene, isosobide, dinitrate, nitroglycerin, theophylline, phenylephrine, ephedrine, pilocarpine, furosemide, tetracycline, chlorpheniramine, ketorolac, bromocriptine, guanabenz, prazisin, doxazosin, and flufenamic acid.

Also, representative of medicaments, their analogs and derivatives thereof, which may be delivered are benzodiazepines such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam and the like; antimuscarinic medicaments such as anistropine, atropine, clininium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17β-estradiol (or estradiol), semi-synthetic estrogen derivatives such as esters of natural estrogen, such as estradiol-17β-enanthate, estradiol-17β-valerate, estradiol-3-benzoate, estradiol-17β-undecenoate, estradiol 16,17-hemisuccinate or estradiol-17β-cypionate, and the 17-alkylated estrogens, such as ethinyl estradiol, ethinyl estradiol-3-isopropylsulphonate, and the like; an androgen such as danazol, fluoxymestetone, methandrostenolone, methyltestosterone, nadrolone decanoate, nandrolone, phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonnorgestrel, medroxyprogesterone acetate, megestrol acetate, norethindrone, norethindrone acetate, norethynodrel, norgestrel, progesterone and the like.

For example, by employing the device and the applicator hereof, it is possible to electrokinetically deliver medicaments such as anti-virals, for treating human papilloma virus, (HPV), e.g., warts (common, flat, plantar and genital), examples of which are Imiquimod® sold as Aldara™ by 3M for genital warts, a type (HPV), Acyclovir®, sodium salicylate, tretinion, benzoyl peroxide, bleomycin, interferons, Podocon-25, OTC products such as Wart Off by Pfizer and Compound W by MedTech or anti-picornavirus class substances, e.g., Pleconaril, to treat coughs and colds, anti-inflammatory medicaments such as dexamethasone and antibacterial agents, proteins, as well as steroids and salts thereof, non-steroidal anti-inflammatory drugs (NSAIDs), and salts thereof, hormones, cytokines, viruses, bacteria, DNA, RNA, (and fragments of both), antihistamines, oligonuceotides, anti-proliferative agents (cancer), specifically 5-fluorouracil (5-FU) and cisplatin, Efudex, or a combination of 5-FU and soviudine, anti-angiogenics such as thalidomide, antibiotics, peptides and peptidomimetics and assemblages of amino acids, phenols and polyphenols, an example of which is PolyphenonE and cosmetic agents, such as retinoids, e.g., hyaluronic acid, vitamins and/or water, skin bulking agents, e.g., collagen, reactive monomers which may polymerize under the skin in non aqueous carriers and be activated by water, botulinum toxins, e.g. botox, bleaching agents, e.g., Eldopaque 4% by ICN Pharmaceuticals, or a combination of Ketorolac, hydroquinone 4%, Glycolic Acid, lactic acid with suitable vehicle and anesthetics, such as lidocaine, xylocaine, prontocaine, prilocaine, fetanyl, remifentanil, sufentanil, alfentanil, novocaine, procaine, morphine HCL and EMLA either in stand alone fashion or with a vasodilator such as epinephrine. Also, medicaments which inhibit fusion between the plasma membrane and viruses and other adventitious agents to prevent entry by viruses and/or other adventitious agents into cells may also be electrokinetically delivered, e.g., behenyl alcohols such as n-disocanol, its analogs or derivatives. Hair growth may be stimulated by Propecia (finasteride), minoxidil, blocking antidihydrotestosterones or antidihydroestrogens. Hair removal may be accomplished by dyeing the hair and or hair root to facilitate removal by laser means or by electrokinetically using, e.g., dihydrotestostersone or dihydroandrogens or dihydroestrogens. Using pigments, tattoos, either temporary (reversible) or permanent may be applied to a treatment site and tattoos when permanent may be removed using suitable medicaments and the instant invention. Water soluble dyes and decals or templates may be employed in conjunction with the device and applicators. Prostate conditions e.g., prostatitis may be treated with antineoplastics. Additionally, the diagnostic sweat test for cystic fibrosis using pilocarpine, peripheral vascular disease using vasodilators, eye (corneal) treatment using florescein, acne treatments with one or more steroids, NSAIDs, such as ketorolac or medicaments such as Benzamycin, benzoyl perixode, cleocin, T-Stat, over the counter (OTC) products two examples of which are Clearasil and Benzac or Accutane, tazarotene sold as Tazorac, adapalene sold as Differin by Allergan and Galderma respectfully or azelaic acid, a topical cream also sold by Allergan, erythromycin as well as combinations of such medicaments may be electrokinetically delivered. Psoriasis may be treated with an antimetabolite, retinoids, synthetic vitamin D, i.e., calciprotriene, cyclosporin A (CSA), Aristocort, from Lederle, anthrax-derm, by Dermik, methotrexate, cortisone like compounds psoralen or anthalin. Eczema and contact or atopic dermatitis may be treated with corticosteroids or antihistamines. Spider veins may be treated with antiangiogenics, or coagulants (clotting factors or fragmented cellulose polymer). Fluoride treatment of exposed single site hypersensitive dentin may be performed with this device and applicator system. Canker sores and RAS may be treated with, e.g., benzoin or sodium fluoride. Post herpetic neuralgia may be treated with local anesthetics mentioned throughout this disclosure and/or with antivirals, e.g., Acyclovir or combinations of anesthetic and antiviral. Erectile dysfunction may also be treated (transcutaneously at site of concern) using prostaglandins such as PGE or alprostadil, nitroglycerin, and the like or papaverine, yohimbine and the like or sildenafil citrate, i.e., viagra, or apomorphine HCl. Other diagnostic uses i.e., removal or extraction of animal or human bodily material, e.g., fluids, versus delivery of medicament include as examples, allergy screening, e.g., using an electrode mounted array of antigens. with a multiplexed-multi-channel application electrode, glucose monitoring and drug testing using electrode mounted specific binders (binder assay) combined with reverse iontophoretic plasma extraction. As a further diagnostic application, body material such as fluids can be extracted into a pad on the electrokinetic device, for example, by reverse iontophoresis. Wounds such as scrapes, cuts, burns, plant allergies, punctures and insect bites or stings can be treated with antihistamines, antibiotics, anti-infectives such as bactracin, Diprolene, topical steroids, and the like, aloe or aloe containing products or OTC products such as Ambesol, Lanocaine and the like, other wound healing agents, such as epidermoid derived growth factors as well as peptides that modulate the inflammatory response and modulators of collagen deposition and modeling as well as other wound healing agents all electrokinetically delivered. Pre-treatment may also include desensitizing agents such as the aforementioned analgesics or salicylic acid. Pruritis, dry skin and keratosis may also be treated using, cortisones and the like, Benadryl itch creme, Lazer creme or EMLA and the like. Actinic keratoses may be treated by electrokinetic delivery of aminolevulinic acid as well as other established antimetabolite agents such as methotraxate, 3% DICLOFENAC IN 2.5% hyaluronic acid, 5FU, 5FU and isotretinion, and the like. Bursitis or mild arthritis may be treated with magnesium sulfate or Dororac from Genderm.

A particular use of the device and applicator hereof is the delivery of Acyclovir® and derivatives and analogs thereof for treatment of recurrent herpetic symptoms, including lesions (oral or genital) and varicella zoster i.e., shingles. Other anti-herpetic medicaments capable of electrokinetic delivery in accordance with the present invention are 5-iodo-2 deoxyuridine (IUDR), cytosine arabinoside (Ara-C), adenine arabinoside (Ara-A), also known as vidarabine, adenine arabinoside monophosphate (Ara-AMP), arabinofuranosyl hypoxanthine (Ara-Hx), phosphonoacetic acid (PAA), thymine arabinoside (Ara-T), 5'-amino-2', 5'-dideoxy-5-iodouridine (AIU), 1-beta-D-arabinofuranosyl-E-5-(2-bromovinyl) uracil (BV-ara-U), also known as sorivudine, 1-beta-D-arabinofuranosyl-E-5(2-chlorovinyl)uracil (CV-ara-U), two halogenated deoxytidines (BrCdR and ICdR), bromovinyldeoxyuridine (BVDU), trifluorothymidin and Penciclovir®, its prodrug, Famciclovir® and analogs and derivatives thereof, e.g., penciclovir. Most if not all topical agents including both Acyclovir® and IUDR have demonstrated only limited efficacy when applied topically to herpetic lesions, or pre-lesion stage sites including prodomal stage skin sites. However, demonstrably improved clinical results have been achieved when applied electrokinetically, e.g., electrophoretically, to treatment sites. Combinations may also be used including but not limited to IUDR and DMSO. By a treatment site is meant a target tissue, e.g., a diseased tissue or diagnostic site for extraction of a substance, underlying or exposed through or on a human individual or lower animal's skin or mucocutaneous membrane including, the eye and also including, but not limited to body cavity and canal sites such as mouth, ear, nose, vagina, and rectum. Some embodiments would not be appropriate for human infants and lower animals and human application to the animal would obviously replace self-application.

In a first aspect of the present invention, an individual may privately self-administer the medicament by employing the self-powered hand-held device to electrokinetically drive the medicament from an applicator into the treatment site, e.g., through the skin or mucocutaneous membrane to a diseased tissue. Preferably, a low-cost throwaway single-use applicator is used to facilitate the flow of medicament into the skin under the influence of the electromotive force supplied to the medicament contained in the applicator by the self-powered hand-held wireless device. The hand-held device is preferably lightweight, compact, inexpensive and portable and comprises a housing configured for self-manipulation and containing a power source, for example, a battery, connected through first and second terminals and suitable electronics, including a current driver and voltage multiplier, with active and ground electrodes. The active electrode is preferably mounted on the end of the device to facilitate manipulation of the device so that the active electrode may engage the applicator against the skin or mucocutaneous membrane. The second terminal of the power source is connected with the ground electrode, i.e., a tactile electrode, on the surface of the device for electrical contact with a second skin site, i.e., a portion of the individual's hand engaging and manipulating the device. By self-manipulation is meant that the individual can engage the device in one hand or a portion thereof and freely orient the device to engage the active electrode of the device through the applicator or directly through medicament against the skin or mucocutaneous membrane generally wherever the treatment site is located and irrespective of whether an applicator is used and, if used, irrespective of whether the applicator is attached to the device or to the individual's skin or mucocutaneous membrane or interposed therebetween with the device subsequently applied to the applicator.

It will be appreciated that the metal portions of any electrode construction may be of any of a variety of metals or metallic films, foils, screens, deposits, mesh, paints including but not limited to aluminum, carbon, gold, platinum, silver, silver chloride, copper or steel, specifically surgical or similar fine grade steel, titanium, zinc or alloys of the aforementioned materials. These metal materials may also be used as a component of an electrode with a plastic base, form or foundation such as Mylar and the like. It is also possible that if the active and ground electrodes are of dissimilar metals or have different half cell reactions the device may generate part or all of its electrical power by this galvanic couple system of which numerous systems are well known in the art and require no further description. At times when hydration, ancillary or otherwise may be required, surfactants to facilitate the rate of hydration, i.e., wetting action, may be employed in, on or about the medicament applicator electrode with materials such as the surfactant Tween 20 or 85, made by ICI America, Neodol 91-6, from Shell Chemical Co., Terigol 15-S-7 from Union Carbide, Pluronic Poloxamer F68 or F127 from BASF or Duponol C or XL made by Dupont Chemical Corp or isopropyl myristate.

In a preferred embodiment employing an applicator, the applicator preferably comprises a substrate having a reservoir, e.g., an open-cellular structure, for containing a medicament. This preferred open cellular or porous portion forms a minimum barrier to movement of medicament molecules under the influence of the applied current to transport the medicament molecules into the skin or mucocutaneous membrane. The applicator thus forms an electrode for application to the treatment site, e.g., an individual's skin and is preferably applied to the device prior to application of the device and attached applicator to the site. It will be appreciated, however, that the applicator electrode can be applied directly to or adjacent to the treatment site, e.g., by using an adhesive, prior to applying the device to the applicator. To secure the applicator electrode to the device prior to application to the treatment site, an adhesive is preferably employed, although other types of securement may be used, such as complementary hook-and-loop fasteners, tabs, post and hole, magnets or the like. It will also be appreciated that an electrical circuit is completed through the active electrode of the device, the applicator electrode and the treatment site for return through the individual's skin in electrical contact with the ground electrode of the device upon application of the device and applicator electrode to the treatment site. Thus, by grasping the device with the individual's hand or finger in contact with the tactile electrode, an electrical circuit is completed from the device through the applicator electrode, the treatment site, the individual's torso, arm and hand and the tactile electrode. To facilitate completion of the electrical circuit, the applicator electrode may have a portion, which overlies the tactile electrode to facilitate the flow of electrical current, For example, the applicator portion overlying the tactile electrode may be open cellular or porous and may contain an electrically conductive material, e.g., hydrogel. When this applicator substrate portion is pressed against the tactile electrode, electrical contact between the tactile electrode and the individual's skin is facilitated. Auxiliary hydration, e.g., wetting the fingers, the material or the tactile electrode may be employed to further facilitate closure of the current loop in any or all applicator or device embodiments. The hydrogel may also have adhesive properties or may contain an adhesive and thereby serve or additionally serve as a mechanism for releasably securing the applicator to the device.

The medicament may be applied to the applicator by the user just prior to use. Alternatively, the medicament can be prepackaged as a unit dose in the applicator electrode. The medicament also may take many forms, for example, the medicament may be formulated as a liquid, a gel, an ointment, a dry powder, a lotion, a foam, a solution or a cream. Depending upon the nature of the medicament, it may also be electrically conductive per se, or require ancillary substances to transport the medicament, e.g., an electrically conductive substance such as water or very weak trace saline to provide the necessary electrical conductivity. The applicator preferably includes a porous or open multi-cellular pad to which medicament can be supplied by the user just prior to use or in which the medicament may be prepackaged. Where the medicament is not sufficiently electrically conductive per se, or is not part of a hydrophilic formulation, the user may hydrate the pad of the applicator to render the medicament transportable by the electromotive force of the electrical current flowing through the pad. Preferably, the applicator is releasably secured, e.g., by adhesive, to the device. Alternatively, the applicator can be applied directly to the skin or mucocutaneous membrane on or surrounding the treatment site, for example, by employing a releasable adhesive or the inherent tack of the substance included with the applicator electrode. In either mode of use, when the device, applicator pad and treatment site lie in series contact with one another and the circuit is completed through the individual's skin, electrical current flows through the pad and skin, driving the medicament into the treatment site, e.g., transdermally into an underlying site.

In another form of the invention and as noted above, the medicament can be prepackaged in the pad of the applicator. For example, one or more rupturable capsules containing the medicament can be located in or adjacent to the porous pad, the encapsulation of the medicament affording long shelf life. Alternatively, the medicament may be prepackaged in or adjacent to the cells of a porous pad with removable seals for preventing exposure of the medicament to ambient conditions thereby also affording long shelf life. Further, different applicators can be prepackaged with different medicaments as required for various treatments. With a prepackaged encapsulated, (including micro encapsulation) medicament, the capsule or capsules can be ruptured by the application of pressure to the applicator pad, thereby spreading the medicament in and among the interstices of the pad. Where seals are used in conjunction with a medicament contained in a porous applicator pad, the seals are preferably adhesively secured to the pad and removed. If necessary, the pad can then be hydrated by the user. This may be accomplished using a separate small sterile vial of fluid by which drops of solution are applied. The applicator is then applied by the user to the device or to the skin or mucocutaneous membrane overlying the treatment site or simply interposed between the device and the treatment site. In this manner, the device, applicator electrode and skin or membrane are serially connected with one another for electrokinetic self-administration of the medicament into the treatment site. As a third alternative, both the medicament and an electrical conductor such as water can be encapsulated within the pad. By applying pressure, for example, finger pressure, the medicament and hydrating capsules can be ruptured, intermingling the medicament and water within or adjacent to the porous multicellular applicator pad, rendering the medicament electrokinetically transportable under the influence of the current flow. A fourth alternative includes pre-hydrating the pad and sealing the pre-hydrated pad from the medicament. When the seals are broken, the hydrating material hydrates the medicament, enabling electrokinetic delivery of the medicament. Alternatively, the medicament may be encapsulated to isolate it from a pre-hydrated pad. A sixth alternative is to encapsulate the hydration material, e.g., water or water containing electrolytes to enhance conductivity and medicament transport. A seventh alternative is to package the medicament with a hydroscopic material which will allow it to pick up water from the air once it has been removed from its protective packaging.

It will be appreciated that the pad containing the electrically conductive medicament or medicament hydrated to afford electrical conductivity through the pad affords a minimum barrier to the movement of the medicament molecules into the treatment site under the electromotive force applied by the completion of the electrical current. Thus, at least a portion of the substrate or pad is preferably thin and highly porous. The pad should be comfortable to the user and if possible be somewhat flexible so as to conform to the treatment site, providing full contact coverage when in place, e.g., fabrics, absorbent gels, cotton or open celled foam. The pad should also have sufficient interstices or open cells, i.e., porosity, to hold quantities of the electrically conductive medicament or the medicament and hydrating material to afford efficacious treatment, e.g., of herpes treatment sites, over a period of time, for example, up to 15 minutes. For most treatments, the period of application is limited, for example, within a range of 1-30 minutes. The hydrating material is preferably water or a very weak trace saline solution lying within a range of 0.001-0.1%, As an additional example of hydrating material, polypropylene glycol, polyethylene glycol or polyvinyl glycol may be used.

Further, the applicator electrode must be void of any short-circuit paths. For example, where the applicator includes a hydrogel on an applicator portion overlying the tactile electrode of the device, the hydrogel must be electrically insulated from the active electrode and the conductive or hydrated medicament in the pad to ensure that the circuit is completed through the individual's skin rather than merely short-circuited through the device and applicator electrode. The distance between the medicament containing electrically conductive portion and the hydrogel serves as an electrical insulator, particularly where the substrate therebetween is non-wicking. Likewise distance between the active and ground electrodes of the device serve the same purpose. Additional physical barriers may be provided, e.g., spaces, openings, valleys and ridges of non-conductive material on either or both the device and the applicator electrode. When both are employed they may be of a complementary nature, e.g., a valley on the device and a ridge on the applicator electrode. A portion of the barrier may also be hydrophilic so as to absorb any of the small amounts of hydration material which may be employed.

In a further preferred embodiment of the present invention, the applicator may contain a magnet for activating and deactivating the power supply in the device. Consequently, when the applicator electrode is applied to the device or to the treatment site and the device is applied to the applicator, the magnet cooperates with the internal electronics of the device to activate the device. Conversely, upon removal of the applicator from the device or the device from the applicator, the magnet in the electrode deactivates the electrical circuit. Other conventional switching means may also be employed, e.g., toggle, twist or push types or the magnet may be separate from the applicator. The applicator may also contain a code carrying system, e.g., bar code or another state of the art system, which when attached to the hand-held device, programs the device to deliver the correct amount of medicament, This allows the hand held device to be used with a range of medicaments without having to reprogram the hand held unit. Also, indicators may be provided on the device to indicate that the device is actuated such that the user can be assured that the medicament is being electromotively driven into the treatment site. Thus, for example, one or more LEDs may be incorporated in the circuit to indicate activation of the circuit. Other indicators or the same indicator in a different mode, e.g., solid vs. flashing may be employed to indicate when the device and applicator electrode are operating satisfactorily to electrokinetically drive the medicament into the treatment site. An additional indicator can be employed to indicate low battery problems. Also, a variable timing device may be incorporated in the electrical circuit. The circuit may be activated for a selected predetermined length of time and automatically deactivated after that time period has lapsed. Alternately, a timer may offer an event signal or series of signals to the user without necessarily reprogramming the time period. For example, if the treatment is interrupted for a brief period of time, the timer may continue timing the treatment provided the interruption is only brief, e.g., a minute or two. If the interruption is prolonged, the timer is automatically reset to provide a period of treatment which is therapeutically effective. Also, a non-ultrasound generated vibration can be added or used in lieu of the LED to indicate working status of the device and that the device lies in a closed current loop via the individual's body surface.

In another form, the applicator may comprise a splint-like strip for releasable securement to an individual's finger with self-contained electronics, a power source and active and ground electrodes formed integrally with the strip. The applicator strip may have a rectilinear, square, circular or shaped pad as the active electrode adjacent the individual's fingertip. The applicator strip preferably includes a split ring for releasably securing the applicator strip to and along an inside surface of an individual's finger. The applicator pad, which may be integral with or form a disposable pad for the applicator strip, is in contact with the active electrode adjacent the individual's fingertip for application to the treatment site. On the opposite side of the strip from the active electrode and in contact with the user's finger is a ground electrode. The batteries within the applicator strip may be air-actuated by removal of a tab overlying battery terminals, After the applicator strip is secured to the user's finger, the user then places the one-time use disposable applicator pad adjacent the user's fingertip and against the treatment site. This completes the circuit through the site and the user's skin. With the applicator pad separate from the applicator strip, the strip may be reusable with other disposable pads. Alternately, the pad may be a built-in part of the strip with or without pre-packaged medicament and/or hydration means, thereby enabling the whole device disposable. The applicator may also be miniaturized to the extent that it may have a thimble-like configuration without a ring and may be frictionally retained on the tip of the individual's finger.

In another aspect of the present invention, the applicator may comprise a completely self-contained disposable unit having its own electronic circuitry and power source. In this aspect, the applicator may be provided (i) without the medicament and electrically conductive material (e.g., water), (ii) with the medicament in a prepackaged form within the applicator requiring only hydration upon use, if the medicament is not per se electrically conductive, or (iii) with both a medicament and hydration material. For example, the applicator in this form may comprise a flexible substrate having a medicament pad on a treatment site side thereof, an optional hydration material layer, overlaid by a first electrode, electronic circuitry including a power source, e.g., a battery, a second electrode and, optionally, a conductive material such as a hydrogel. By applying the medicament-containing pad to the treatment site and holding the applicator on the site by a finger or hand of the individual pressing on the applicator opposite the site, an electrical circuit is completed through the second electrode, the electronics, the medicament applicator electrode and the skin or mucocutaneous membrane between the site and the individual's finger or hand (i.e., along the finger or hand, the individual's arm, torso and site). Consequently, the medicament is electromotively driven by the electrical current into the site. The self-contained disposable unit may be removed from its package by the individual upon contact of the individual's finger with a tacky hydrogel exposed on the unit after the package is opened. This finger contact with slight finger pressure may cause contact between the hydration material and the medicament prior to removal from the package. Also, the finger contact and removal from the package further allows highly intuitive manipulation of the unit to the treatment site and ease of use given the lightweight and compact size of the unit. The unit may also be placed in a position where the finger contact is replaced by the contact of another grounding site such as would be the case if, by example the unit were placed in the mouth between the gum and inside mucosal tissue of the mouth or if the unit were placed inside the arm and contacted the upper rib cage or if the unit were designed and formed in a fashion similar to a contact lens for ocular treatments. It should be appreciated that the orientation of the active and ground electrodes and placement of the medicament could be reversed in these or other like uses.

The battery for the circuit, for example, a zinc oxide battery, may be of the type activated by exposure to oxygen. In that battery, a tab overlies battery terminals which, when the tab is removed, exposes the contacts to oxygen thereby activating the battery. Various other types of miniaturized power sources may be provided, e.g., film sheet stacked batteries. It will also be appreciated that the medicament may be applied to the applicator pad by the user after the applicator is unpackaged and, if not per se conductive, the pad may also be hydrated by the user prior to application to the treatment site. Alternatively, the medicament may be prepackaged within the pad, for example, in one or more rupturable capsules and if not electrically conductive per se, one or more additional capsules containing hydrating fluid, e.g., a conductive fluid, such as water or saline may be prepackaged in the applicator as well. By squeezing the applicator electrode to rupture the capsule or capsules, the encapsulated medicament and, if necessary, the hydrating fluid, intermingle with one another and provide the necessary electrical conductivity through the applicator pad to enable electromotive transport of the medicament through the skin. It will be appreciated that the grounding electrode lies on the opposite side of the applicator from the active electrode and a circuit is therefore completed through the individual's finger or hand holding the applicator over the treatment site and the individual's arm and torso. To ensure electrical contact with the individual's hand or finger and the ground electrode, the top or outer portion of the applicator remote from the medicament pad may contain a conductive hydrogel.

In a further alternative form hereof, the applicator comprises a self-contained disposable unit likewise having its own electronic circuitry and power source. In this form, the active electrode may form a portion of the applicator spaced from an electrically insulated ground electrode also forming part of the applicator. The applicator is configured such that the first or active electrode of the applicator lies in electrical contact with the applicator pad (electrode). The active applicator electrode is applied to the treatment site and the ground electrode on the applicator is placed in electrical contact with the user's skin. An electrical circuit is thereby completed through the applicator, the applicator electrode and the treatment site with the return circuit through the skin, and the ground electrode of the applicator. The spacing between the active electrode and the ground electrode in electrical contact with the treatment site and the skin, respectively, can be quite small, i.e., on the order of one-half inch.

As mentioned previously, the medicament may be formulated as a liquid, gel, ointment, dry powder, lotion, foam, solution or cream. Where a liquid constitutes the medicament, the applicator electrode for use with the device may include an electrically insulative housing, for example, a torus, for containing the liquid. On one side of and secured to the torus is a microporous film overlaid by a removable barrier, e.g., foil or inert material adhered to the insulated housing to prevent transfer of the liquid within the applicator electrode externally. The opposite side of the insulative housing may likewise be confined by a barrier overlying the housing. The insulative housing preferably has tabs for attaching the applicator electrode to the device similarly as previously described. A conductive plate may overlie the foil or the applicator electrode may be applied to the device directly with the active electrode of the device in electrical contact with the barrier. By removal of the adhesively secured barrier layer and application of the applicator electrode to the site, electrokinetic transfer of the medicament can be accomplished.

In a further form, the active and ground electrodes may be spaced one from the other in a self-contained unit and separated by a malleable or tensioned arm. For example, the ground electrode may be adhesively secured to the individual at a location adjacent the medicament delivery device and the active electrode placed in contact with the site. The springbiased or malleably tensioned arm holds the active electrode with an optional gimbal component in electrical contact with the treatment site in a fully flush or full contact manner, avoiding only partial contact and hence avoiding less than effective treatment. This permits hands' free electrokinetic delivery of the medicament to the treatment site.

In a still further form, a self-contained unit having its own electronic circuitry and power source for hands' free application to the treatment site is provided. In this form, a generally U-shaped clip having opposite ends which mount the ground and active electrodes, respectively, as well as the power source and electronic circuitry, may be applied in a gripping or clamping manner to clip the self-contained unit adjacent the treatment site such that the active electrode engages the treatment site for electrokinetic delivery of the medicament.

In a still further form of the present invention, electrokinetic medicament delivery may be applied in an ocular applicator similar to and worn like a contact lens. The mechanism of the electrokinetic delivery may be multi-channel, for example, as described and illustrated in U.S. Pat. No. 5,160,316, now U.S. Pat. No. Re. 36,626, incorporated herein by reference. Thus, a delivery device similar to a contact lens may be employed to therapeutically treat the conjunctiva for acute glaucoma using as an example, Xalatan or even to contour the eye by delivering agents that retain $H_2O$, such as hyaluronidase or hyaluronic acid, which would swell the conjunctiva in specific sites of the eye. Antiviral drugs foscarnet and ganciclovir either alone or in combination may be electrokinetically delivered for treating herpetic eye infections, e.g., cytomegalovirus (CMV) and CMV retinitis. Differential levels of power and agent delivery are possible with the multi-channel delivery. In this manner, the refraction of the light can be modified by changing or altering the shape of the eye/conjunctiva. The medicament delivery device may be worn or applied periodically for various time periods, for example, within a range of 1 to 60 minutes.

In the above aspects of the present invention, the circuitry limits the maximum current available to the applicator electrode to preferably less than about 1 milliampere per two square centimeters of the skin-contacting surface area of the electrode. Depending upon the working electrode's skin-contacting surface configuration, the current level can vary from about 0.1 to about 1.2 milliamps. While higher currents have been used, user discomfort can be experienced. Buffers could be employed to overcome this milliamp range ceiling. It is also another feature hereof that the electrical current can be ramped up and ramped down, respectively, at the beginning and end of the treatment. See, for example, prior U.S. Pat. No. 5,160,316, now U.S. Pat. No. Re. 36,626, the disclosure of which is incorporated herein by reference. Ramping contours of different configurations can be used, for example, linear, non-linear, exponential, pulsed, or otherwise shaped. Also, while direct current is preferred, alternating current can be used.

In all of the foregoing embodiments, facilitators may be employed to minimize or eliminate the barrier to the transfer of the medicament molecules through the skin. For example, acetic acid or dimethylsulfoxide (DMSO), alcohols, such as ethanol and isoproanol, ethyalactate, sulphoxides, fatty acids, such as oleic acid, lauric acid, capric acid and caprylic acid, sodium lauryl sulfate, acyl lactylates (except in their salt form), e.g., caprol lactyic acid and lauroyl lactylic acid, esters, (1-dedecylazacycheptan-2-one) (Azone), pyrrolidones, such as dodecyl pyrrolidone, dimethyl lauramide, linear dialiphatic or aliphathic, sulfoxides, unsubstituted or mono or di-substituted amides and di-substituted amines among others, urea, cis-urocanic acid or polyoles may be used. It may also be useful in electrokinetic transport of some medicaments to use a second facilitator or skin permeation enhancer which may be a monoglyceride or mixture of monoglyerides of fatty acids such as glycerol monolaurate (GML) or glycerol monooleate (GMO), lauramide diethanolamine (LDEA), or esters of fatty acids having from 10 to 20 carbon atoms. By using these substances, the skin can be disrupted, enhancing the exposure of the dermis to electrokinetic forces. Another type of facilitator is a component which may encase a given molecule within a lipid barrier but makes it less polar and thereby facilitates penetration of the skin by the medicament. An example is gylcesol or phospholipids such as phosphaticylcholine.

It will be appreciated from the foregoing that usage of the device and applicator requires minimal instruction. Where the medicament is prepackaged with the applicator, there are no concerns regarding the dosage as a single unit dosage which is therapeutically effective over the period of application is provided. Moreover, the device and applicator do not require any calibration or settings as the supply of current is fixed by the device electronics. Further, there is no second or ground electrode separate from the device whereby the device is easily used without a separate ground electrode. The power source may be limited to providing only single use longevity. Thus, the power supply may be replaced when a device is reused or the device itself may be discarded. Numerous components may be constructed and linked for short life cycle upon use without negating a prior long shelf life. The applicator and even the device per se are readily disposable.

In a preferred embodiment according to the present invention, there is provided an applicator for use in an electrokinetic device to deliver substance to a treatment site for an individual, comprising a substrate including a substance-dispensing portion having a first face for electrical contact with an electrode carried by the electrokinetic device and a second face for electrical contact with the treatment site, a reservoir carried by the substrate for containing the substance and including a rupturable barrier for maintaining the substance apart from the substance-dispensing portion, the substance-dispensing portion providing an electrically conductive path through the substrate including at least in part the first and second faces of the substrate for electrokinetically driving the substance into the treatment site upon rupture of the bather releasing the substance into the substance-dispensing portion and application of the device to the first face and passage of an electrical current through the applicator.

In a further preferred embodiment according to the present invention, there is provided an applicator electrode for use with an electrokinetic device to deliver a substance to a treatment site for an individual, comprising a substrate having a first surface and a second surface opposite the first surface, the substrate including a substance-dispensing portion comprising a cell or a plurality of cells forming an aperture or a plurality of apertures between the first surface and the second surface, a reservoir carried by the substrate for containing the substance and including a rupturable barrier for maintaining the substance segregated from the substance-dispensing portion, an adhesive layer covering at least a portion of the second surface of the substrate opposite the first surface for releasably attaching the substrate to an electrokinetic device containing an electrical power source for electrokinetically driving the substance through the first surface and into the treatment site upon rupture of the barrier releasing the substance into the substance-dispensing portion and application of an electrical current to effect delivery of the substance in the cell or plurality of cells to the treatment site.

In a still further preferred embodiment according to the present invention, there is provided an electrokinetic delivery device for personal use in self-administration of a substance to a treatment site on an individual comprising a substrate shaped for underlying the undersurface of an individual's finger from a tip thereof to a location past the first finger joint, a self-contained power source within the substrate, a first electrode carried by the substrate and exposed adjacent the tip of the individual's finger, the first electrode being in electrical contact with the power source, a second electrode carried by the substrate and exposed for contact with the individual's finger, the second electrode being in electrical contact with the power source whereby, upon application of the first electrode over a treatment site with the substance disposed between the first electrode and the treatment site, the device applies current for electrokinetically driving the substance into the treatment site.

In a still further preferred embodiment according to the present invention, there is provided a delivery device for self-administration of a substance to a treatment site on an individual, comprising a self-contained disposable applicator including a pad for containing the substance, a power supply, a first electrode overlying the pad and electrically connected to the power supply and a second electrode having a tactile surface in electrical contact with the power supply and lying on a side of the applicator remote from the pad, whereby, upon the individual's hand or a portion thereof in contact with the tactile surface of the second electrode holding the applicator pad against the treatment site, an electrical circuit is completed between the first electrode through the treatment site and the second electrode via the tactile surface and the individual's hand and body for electrokinetically driving the substance into the treatment site.

In a still further preferred embodiment according to the present invention, there is provided a delivery device for self-administration of a substance to a treatment site on an individual, comprising a self-contained disposable applicator including a pad for containing the substance and lying on a first side of the applicator, a power supply, a first electrode overlying the pad and electrically connected to the power supply and a second electrode in electrical contact with the power supply and lying on the first side of the applicator whereby, upon application of the applicator pad against the treatment site, an electrical circuit is completed between the first electrode through the treatment site and the second electrode via a portion of the individual's body for electrokinetically driving the substance into the treatment site.

In a still further preferred embodiment according to the present invention, there is provided a medicament-dispensing electrokinetic device for delivery of a medicament to an individual's treatment site, comprising a housing having a portion thereof shaped for manual manipulation by the individual's hand and an electrical circuit including a normally open switch and a first electrode formed of electrically conductive material and exposed for contact with the medicament, the first electrode being mounted for movement relative to the housing between first and second positions, the first electrode closing the normally open switch and completing the circuit in response to movement of the first electrode from the first position toward the second position, a power source forming part of the circuit and contained within the housing, the power source having first and second terminals, the first terminal being in electrical contact with the first electrode, a tactile electrode forming part of the circuit in electrical contact with the second terminal of the power source and having a surface for contact with the individual's skin, the device being operable to electrokinetically drive medicament disposed between the first electrode and the individual's treatment site to effect delivery of the medicament into the treatment site in response to pressing the first electrode toward the treatment site causing closing of the switch and completion of the electrical circuit through the closed switch between the first terminal through the first electrode and the treatment site and the second terminal via the tactile electrode and a portion of the individual's skin.

Referring now to the drawing figures, particularly to FIG. 1, there is illustrated a portable, self-contained, lightweight, compact, hand-held electrokinetic medicament delivery device, generally indicated 10, adapted for use with an applicator, described in detail below. The device 10 includes an outer housing 12 containing a power source, for example, a battery 14, and electronic circuitry including a voltage multiplier 16 and a current driver 18. As illustrated, battery 14 includes a first terminal 20 and a second terminal 22. The first terminal 20 is coupled to the voltage multiplier 16 which steps up the voltage supplied by the battery 14 and applies the stepped-up voltage to the current driver 18. Current driver 18 is in contact with a first or active electrode 24 exposed through housing 12, preferably at an end thereof. The second terminal 22 is in contact via a spring 26 and a conductor 28, with a ground or tactile electrode 30 also exposed through housing 12, preferably along a side wall thereof. It will be appreciated that housing 12 is sized and configured to be held within an individual's hand for orientation such that the first or active electrode 24 can be in electrical contact with a treatment site through a conductive medicament-containing pad of an applicator, described below. Thus, in a preferred embodiment, the housing 12 may be of a cylindrical form, with the first or active electrode 24 at one end of the cylinder. It will be appreciated, however, that housing 12 can assume other shapes to facilitate the purposes of device 10, namely to provide a portable, self-contained device having an integral power source which, in conjunction with the applicator, may electrokinetically drive medicament through an individual's skin or mucocutaneous membrane into a treatment site when the applicator and device are applied to and overlie the treatment site. For example, and referring to FIG. 2A, the housing 12a may have a bend intermediate its opposite ends forming a handle 32 at one end having a tactile ground electrode 30a exposed through the handle. The opposite end terminates in an active or first electrode 24a similarly as in FIG. 1. Thus, the handle 32 forms a grip for orienting and manipulating the device 10a relative to the treatment site.

The circuitry limits the maximum current available to the applicator to preferably less than about 1 milliampere per two square centimeters of the treatment site-contacting surface area of the applicator. However, depending upon the working surface of the applicator pad in contact with the site, the current level can vary from about 0.1 to about 1.2 milliamps per two square centimeters to avoid minor discomfort and deleterious side effects. These limitations also apply to each channel of a multi-channel device as discussed herein with reference to U.S. Pat. No. 5,160,316, now U.S. Pat. No. Re. 36,626.

The hand-held device 10 and 10a may be modified to include a piezoelectric element 19 for imparting ultrasonic vibrational motion to the active electrode 24 to further facilitate transdermal or transmucocutaneous delivery of electrokinetically transportable substances, e.g., medicaments. The piezoelectric element 19 is located on the active electrode 24. Power is supplied to energize the piezoelectric element 19 by a conductor 21 connected with the tactile electrode 30, the piezoelectric element 19 being in electrical contact with the active electrode 24. An optional switching element may be used to energize the piezoelectric element or not, as desired, depending upon the particular treatment mode. The combination of an electrokinetically delivered substance into a tissue, together with inducing an ultrasonic vibration in the tissue, enables an opening of pores further facilitating penetration of the medicament. It also facilitates removal of coloration, such as a blemish, freckle or tattoo within the skin by delivery of a suitable bleaching agent, provided as the medicament in the applicator, which will now be described.

Figure 4:
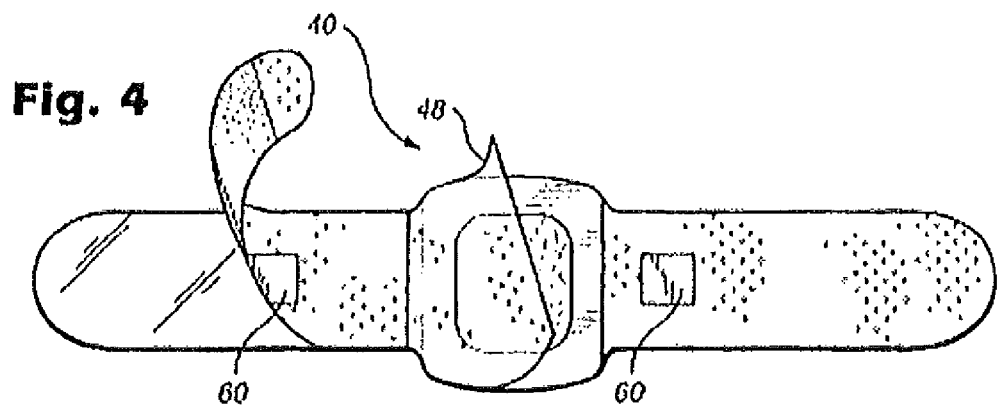
FIG. 4 is a plan view of an applicator from the skin side.
Figure 5:
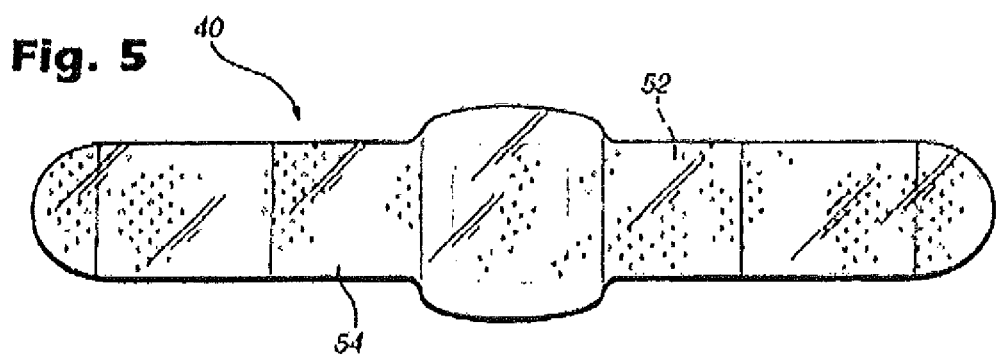
FIG. 5 is a plan view of the applicator from the device side.
Figure 6:
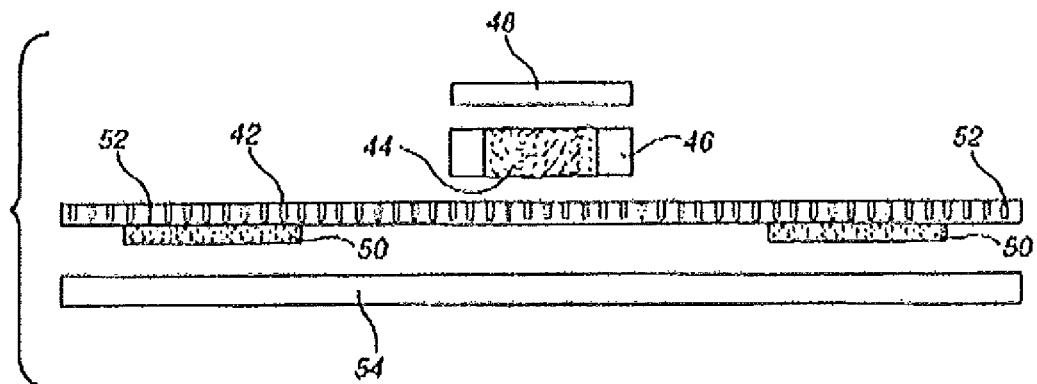
FIG. 6 is an exploded side elevational view illustrating the various parts of the applicator.

Referring to FIGS. 4-6, there is illustrated an applicator, generally designated 40, having a treatment site-contacting side and a device-contacting side as illustrated, respectively, in FIGS. 4 and 5. As best illustrated in FIG. 6, applicator 40 includes a substrate 42 formed of a porous open cellular material. A suitable substrate material may comprise a fabric manufactured by Cerex of Pensacola, Fla., identified as Type DN, Group DN07&DN15. Other suitable types of materials may also be used, provided those materials, at least in the portion of the substrate through which the medicament will be transported to the treatment site, constitute a minimum barrier to the transfer of the medicament molecules from the applicator to the site. On the skin or mucocutaneous side of the applicator 40 as illustrated in FIGS. 4 and 6, there is provided a pad 44 surrounded by a containment barrier 46. The pad may likewise comprise a porous open-cellular material similar to the substrate but preferably comprises a more dense material such as cotton for retaining the medicament. Cotton is sufficiently porous and open-cellular to enable the medicament to be electromotively driven from the cotton pad into the site. It will be appreciated that the pad 44 should be inert to the medicament, as well as non-corrosive and stable when in contact with the medicament. While cotton is preferred, other suitable materials may include plastic pads such as polyethylene, paper, porous ceramics, open-celled porous polytetrafluoroethylene, polyurethane or other plastics, as well as open-celled silicone rubber and vinyl.

The containment barrier 46 is formed of a non-electrically conductive material, which prevents the medicament from weeping or wicking onto portions of the substrate adjacent the medicament pad. Preferably, however, barrier 46 comprises a closed-cell foam, for example, a foam manufactured by Avery Dennison of Pasadena, Calif., identified as Avery Foam Med 5637. While not shown, the foam is preferably adhesively secured to the substrate 42 with margins of the pad 44 frictionally or adhesively retained within the peripheral confines of the barrier 46. A flap 48 overlies the exposed side of the pad and is preferably adhesively secured along one side to one side of the barrier 46 such that the pad 44 can be exposed by lifting or removing the flap. It will also be appreciated that the pad 44 may be incorporated or embedded in the substrate 42. For example, the pad 44 may reside in a cutout portion in the substrate.

Figure 2:
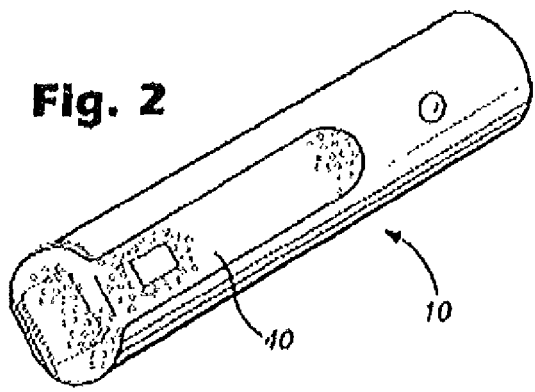
FIG. 2 is a perspective view of the device with the applicator applied thereto.

On the device side of the applicator and on opposite sides of the pad 44, the substrate extends to form wings 52 for releasably securing the applicator to the device. Preferably, a releasable contact adhesive 50 is applied to the applicator wings 52 for releasably securing the applicator to the device 10. For example, as illustrated in FIG. 2, the applicator 40 illustrated in the form of a strip has a central portion of the strip, i.e., the pad 44, overlying the active electrode 24 at the end of housing 10 with the applicator wings 52 folded along opposite sides of the housing 10 and releasably secured thereto by the adhesive 50. A release liner 54 is provided on the device side of the applicator overlying adhesive 50 and which liner 54 is removed by the user upon application of the applicator to the device, It will be appreciated that other methods of releasably securing the applicator to the device may be employed. For example, hook-and-loop type fasteners may be used with the hooks or loops on the device and the loops or hooks on the applicator. Magnets or spring clips or other mechanical-type fasteners may be employed. The applicator as illustrated in FIGS. 4-6 is also illustrated in the form of a strip similar to a Band-Aid. It will be appreciated, however, that other configurations and shapes of the applicator may be employed, depending upon the configuration of the device. For example, an applicator 40a having a pad formed of similar material as pad 44 may be employed for use with device 10a of FIG. 2A, Applicator 40a may be formed in a circular configuration without wings and may be adhesively or otherwise secured to the active electrode 24a of housing 12a. For example, the peripheral margin of the applicator 40a may have a releasable adhesive for releasable securement to the active electrode 24a on the end of device 10a. In this form, the applicator need not have conductive portions overlying the ground electrode 30a. It will also be appreciated that the applicator is formed of a flexible material generally conformable to the treatment site surfaces to the extent possible given the shape of the active electrode 24, 24a on the device 10, 10a.

The applicator 40 is intended for a single use. That is, once the medicament has been electrokinetically driven from pad 44 into the site, the applicator may be removed from the device or the site and discarded. Where the medicament is prepackaged with the applicator, a coloring agent can be employed, such as iodine, which turns color upon contact with the starch in the open-celled material to visibly indicate that unit dose medicament has been used. Other types of coloring agents can be used to indicate usage of the applicator, e.g., pH indicators, wet saturation indicators or oxidizable pigments.

Figure 7:
FIGS. 7 and 8 are views of the applicator pad, respectively, illustrating an encapsulated medicament and a combination of encapsulated medicament and hydration fluid within the applicator pad.
Figure 8:
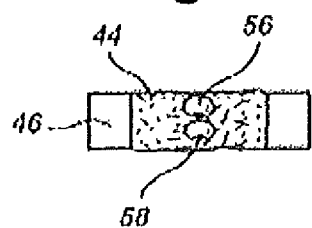

The applicator may be provided to the user without medicament within the applicator pad 44. Thus, when using the applicator, the user may apply the medicament to the applicator pad 44 such that the medicament lies within the interstices of the material of the pad 44. If the applied medicament is not per se conductive, the pad containing the medicament may be hydrated by the application of water, for example, by using an eyedropper. In a preferred form, however, the medicament is supplied and prepackaged with the applicator. For example, the medicament may be contained within a rupturable polymer reservoir or capsule 56, as illustrated in FIG. 7. By encapsulating the medicament, a long shelf-life is assured. To use the applicator with the encapsulated medicament, the capsule 56 can be ruptured by applying pressure to the pad 44, for example, by pressing the pad between the individual's fingers or against the active electrode when the applicator is applied to device 10, or against a surface of packaging in which one or more of the applicators are provided. By rupturing the capsule, the medicament permeates the interstices of the pad 44. If the medicament requires hydration to afford electromotive transport into the treatment site, e.g., a lesion upon application of the electric current, the user may hydrate the pad similarly as previously described. Alternatively, an additional one or more capsules containing hydrating material, e.g., water or saline, may be prepackaged with the applicator. A very weak trace saline solution within a range of 0.001-0.1% and preferably less than 0.05% may be used. As illustrated in FIG. 8, the pad 44 includes one or more medicament capsules 56 and one or more hydration capsules 58. By applying pressure to the two or more capsules, the capsules may be ruptured and the medicament and hydration material intermingled with one another within the interstices of the pad 44, rendering the applicator pad susceptible to conducting current for the electrokinetic delivery of the medicament to the lesion.

Referring back to FIGS. 4-6, a magnet 60 is preferably incorporated into the substrate 42 on one or opposite sides of the pad 44. The electrical circuit in the device may therefore include a magnetic field responsive switch for actuating and deactuating the electrical circuit. Thus, when the applicator is applied to the device, the circuit is activated and when removed, the circuit is deactivated.

Instead of or in addition to the adhesive 50, a conductive gel may be provided within the wings 52 of the porous substrate 42. It will be appreciated that as the applicator electrode is applied to the device 10 (FIG. 2), the wings 52 of the substrate overlie the tactile electrode 30 of the housing 10. The conductive gel thus facilitates electrical conductivity between the individual's fingers or hand overlying the wing portions of the applicator and the tactile electrode 30 to complete the circuit. Thus, the cells of the substrate on one or both wings 52 may be provided with a conductive substance, e.g., a hydrogel. These wings with hydrogel are electrically insulated from the pad 44 and the medicament. Thus, electrical insulating barriers may be provided between the pad 44 and the conductive wing or wings. Such barriers may comprise substantial spacing between the pad and wing with non-conductive material therebetween or physical barriers such as openings, ridges or valleys in the substrate portions interconnecting the pad 44 and the one or more wings of conductive material.

To use the combination device and applicator illustrated in FIGS. 1-8, the applicator 40 is preferably applied to the device by aligning the pad 44 with the active electrode 24 on the end of housing 12. The wings of the applicator are folded along opposite sides of the device and adhered or held to the device overlying the ground electrode 30. With the substrate being at least partially open celled, porous, or cutout, e.g., to contain medicament in gel, solution, cream, foam, ointment or liquid form, the individual's fingers pressing against the substrate and/or the tactile electrode 30 complete an electric circuit path between the device and the individual. Where hydrogel is applied to the wings 52 of the applicator 40, the hydrogel facilitates the completion of the circuit between the individual's hand or finger and the tactile electrode. Whether hydrogel is employed or not the individual may add water to his/her fingers or hand, thus facilitating electrical conductivity. With the applicator 40 applied to the device, the device is actuated, for example, by locating the magnet 60 in a position to close the magnetic switch within the electrical circuit. A conventional on/off switch may be used in lieu of the magnetic switch. The active electrode 24 is also in electrical contact with the medicament containing pad 44 by contact therewith. By manipulating the device, the pad 44 of the applicator is brought into the contact with the treatment site on the individual's skin. Upon contact, electrical current flows between the active electrode 24 in the handpiece, through the medicament-containing pad 44 into the treatment site, through the patient's skin, along the torso and arm for return through the finger or hand to the ground electrode 30. Consequently, the medicament is electromotively transported through the individual's skin or mucocutaneous membrane, thus enhancing local delivery of the medicament to the treatment site.

Figure 2A:
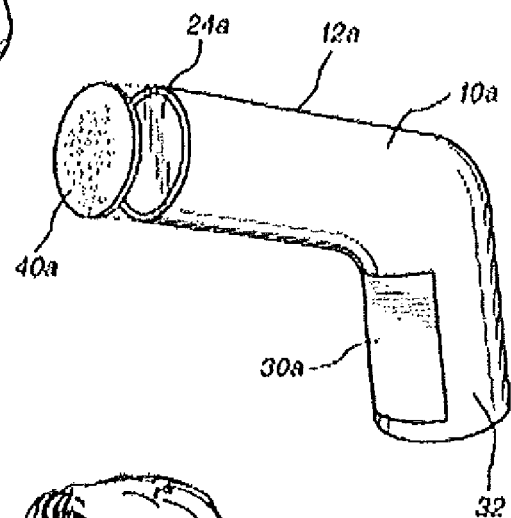
FIG. 2A is a view similar to FIG. 2 of a modified form of the device and applicator.
Figure 3:
FIG. 3 is a perspective view illustrating the device and applicator in use by an individual and being applied to a lesion on the individual's chin.

When using the device 10a of FIG. 2A, the applicator 40a may be secured to the end of housing 12a overlying the active electrode 24a or applied to the treatment site. The individual holding the device 10a makes electrical contact with the ground electrode 30a of the handle 32 by grasping the handle. To ensure good electrical contact, the individual may also add water to his/her fingers or hand. The device 10a is then manipulated to contact the active electrode 24a through the applicator 40a with the treatment site thereby completing the electrical circuit similarly as in the embodiment of FIG. 2.

The device per se may also be applied to a treatment site without a medicament, e.g., without use of the applicator 40 or 40a. The current delivered to the treatment site by the device alone or with or without ultrasonic application or enhancement has beneficial and healing effects in the treatment of the various maladies noted previously.

Figure 9:
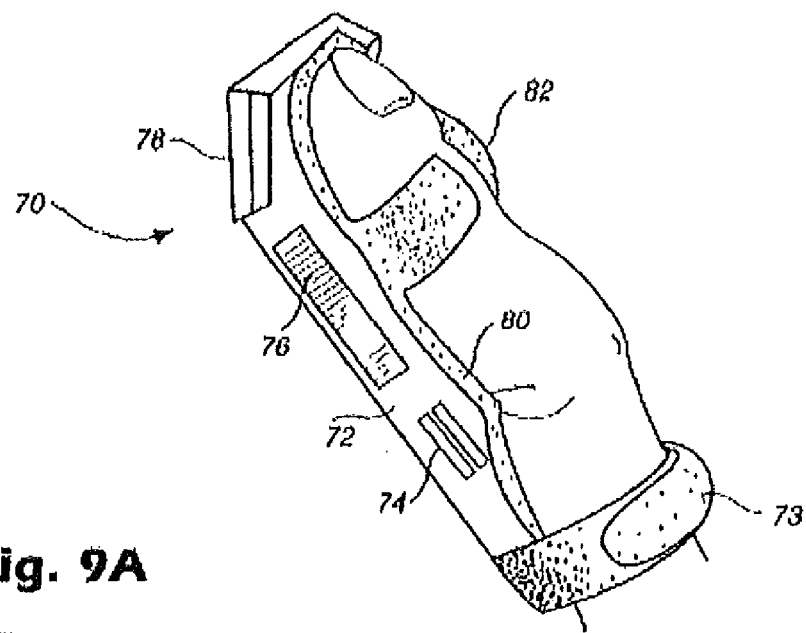
FIG. 9 is a perspective view of a splint-like strip forming a self-contained applicator electrode in accordance with a further embodiment of the present invention.
Figure 10:
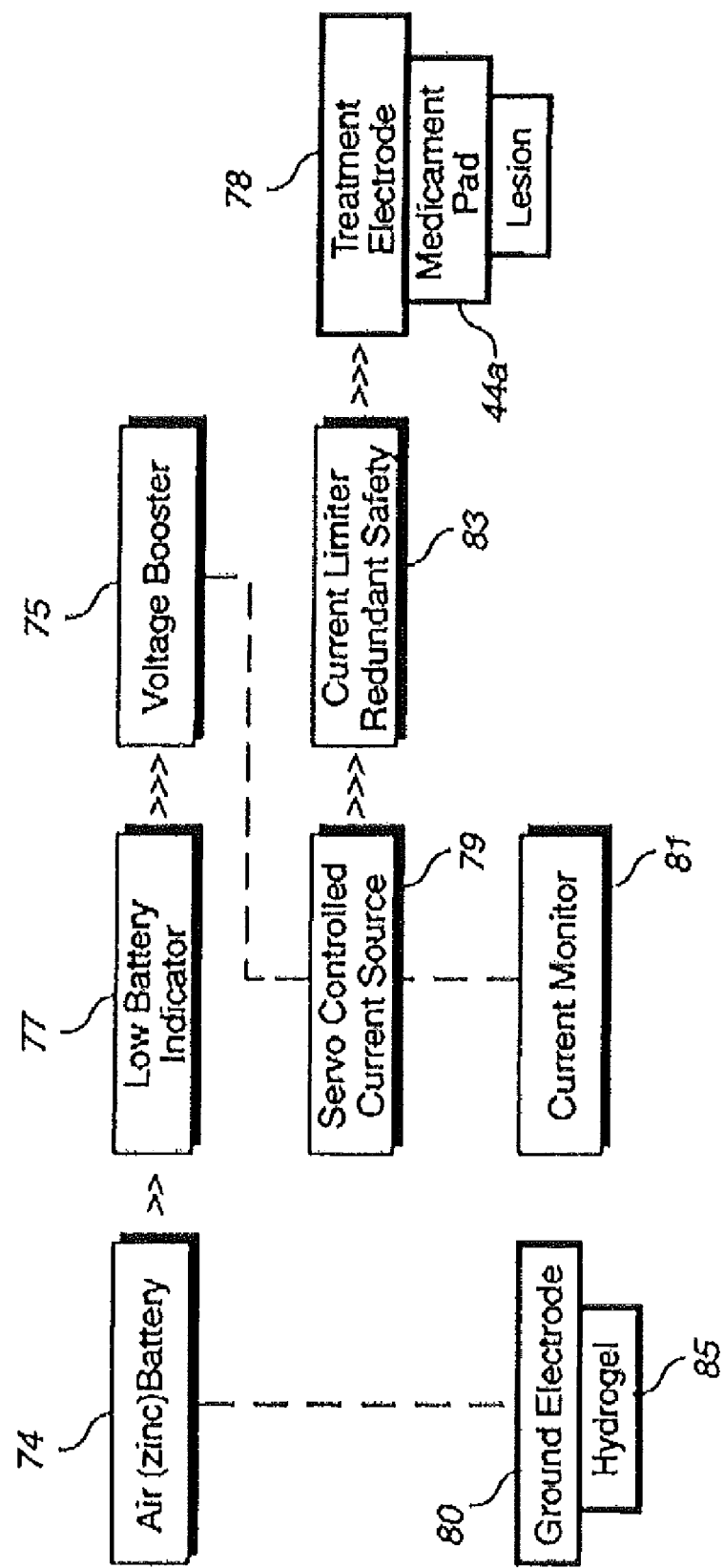
FIG. 10 is a schematic view of an electrical circuit for use with the applicator electrode of FIG. 9.

Referring now to the embodiments hereof illustrated in FIGS. 9 and 10, there is illustrated a completely self-contained disposable unit containing electronic circuitry and a power source for electrokinetically delivering medicament to a treatment site. As illustrated, the self-contained unit, generally designated 70, includes a semi-flexible substrate 72, for example, formed of a plastic material, for underlying an individual's finger and shaped according to the inside surface of an individual's finger. The substrate 72 passes along one or more of the finger joints. The substrate 72 includes batteries 74, for example, conventional zinc oxide batteries which may be actuated by removal of a tab exposing battery contacts to the atmosphere. Additionally, the substrate 72 includes electronics 76 for supplying a flow of current to an active electrode 78 carried at the fingertip end of the substrate 72 and angled relative to the linear extent of substrate 72. It will be appreciated that the active electrode 78 is electrically coupled to the electronics 76 and batteries 74. Additionally, a ground electrode is electrically coupled to the other terminal of batteries 74 and is electrically insulated from the active electrode 78. The ground electrode 80 may comprise a flexible material, portions of which may be in the form of a split ring 82. Thus, the full length of the individual's finger may be in contact with the ground electrode, affording a good electrically conductive contact therewith. Additionally, a retainer, for example, a retaining strap 73, is provided adjacent the inner end of the substrate 72 to, in addition to the split ring 82, releasably secure the applicator electrode to the individual's finger. The retaining strap 73 may include semi-rigid arcuate split ring portions, a full ring integral with substrate 72 or a flexible strap with fasteners to secure the strap ends to one another, for example, hook-and-loop type fasteners.

Figure 9A:
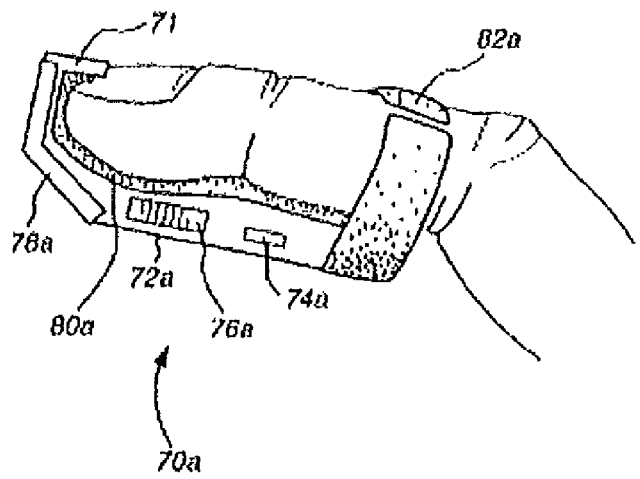
FIG. 9A is a view similar to FIG. 9 illustrating a further form of the strip of FIG. 9.

A similar self-contained unit 70a is illustrated in FIG. 9A wherein like parts are designated by like reference numerals followed by the suffix "a." The substrate 72a extends along the underside of an individual's finger but only along the finger from its tip, past the first joint and terminating short of the second joint. As in the embodiment of FIG. 9, substrate 72a includes batteries 74a, electronics 76a, an active electrode 78a at the fingertip, and a ground electrode 80a including split ring 82a. Additionally, the tip 71 of the substrate 72a may curve back over the fingertip to assist in securing the substrate to the fingertip.

The electronic circuitry for the applicator electrodes 70 and 70a of FIGS. 9 and 9A is illustrated in FIG. 10 and which circuitry is applicable to all embodiments hereof. The power supply for the device 70 includes an air-activated battery 74, coupled through a voltage booster 75 by way of an optional low battery indicator 77. The air-activated batteries may be replaceable and other types of small batteries, such as lithium disks, could be used. The voltage booster 75 is connected to a servo controlled current source 79 and, optionally, to a current monitor 81. The current source 79 is electrically coupled to a current limiter 83 for limiting the current applied to the active electrode within the limits previously discussed. The current limiter 83 is coupled to the treatment electrode 78. In FIG. 10, the treatment electrode is illustrated as applied to the treatment site, e.g., a lesion, through a medicament pad 44a. The ground electrode is also illustrated as applied to the skin by way of an optional electrically conductive hydrogel 85. The medicament pad 44a may be releasably or permanently secured to the device 70, preferably in overlying relation to the active electrode 78. Thus, the device 70 may be a one-time-use disposable or, if the pad is separate, the device 70 may be reused with additional pads. The overlying pad 44a may contain a prepackaged medicament M or any of the alternative combinations of pad, medicaments and hydration disclosed in this application. Alternatively, the pad 44a may be provided in a separate package with the medicament in capsulated form as previously described, In either case, the medicament pad is applied between the active electrode 78 and the treatment site. By removing the tab overlying the battery terminals, the power supply is activated. This may be accomplished when opening the packaging or upon removal of the device from the packaging. When the active electrode 78 is placed in contact overlying the treatment site surface, the circuit is completed through the individual's body, including the finger in contact with the ground electrode.

The applicator 70 is preferably a single-use applicator which may be discarded after use. In an alternate form, the substrate 72 may be shaped in the form of a thimble for overlying the entirety of the fingertip of the individual. The electronics 76 and batteries 74 may be formed on the back side of the thimble opposite the side containing the active electrode, with the ground electrode lying along the inside surface of the thimble and electrically insulated from the active electrode.

Figure 11C:
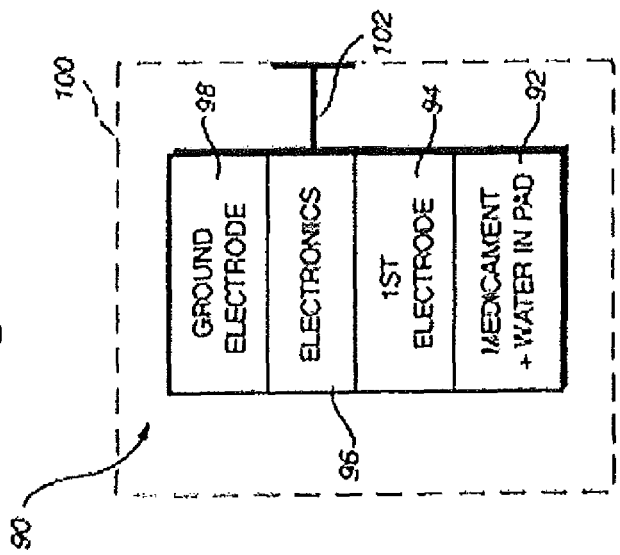
FIGS. 11A, 11B and 11C are schematic representations of a self-contained applicator illustrating the layers of the applicator within a packaging material.
Figure 11B:
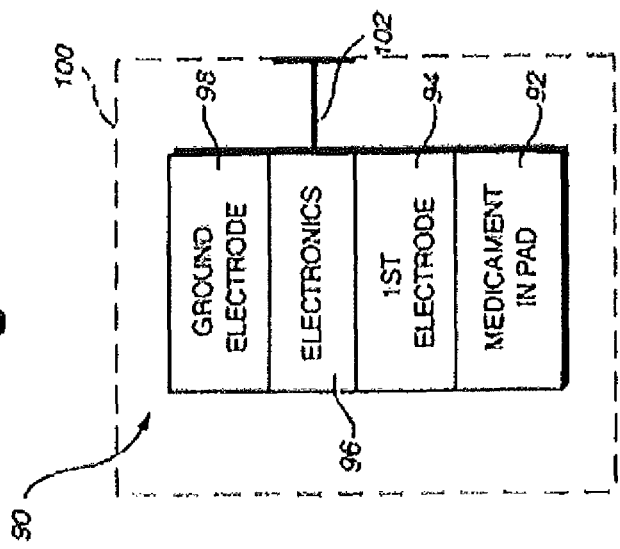
Figure 11A:
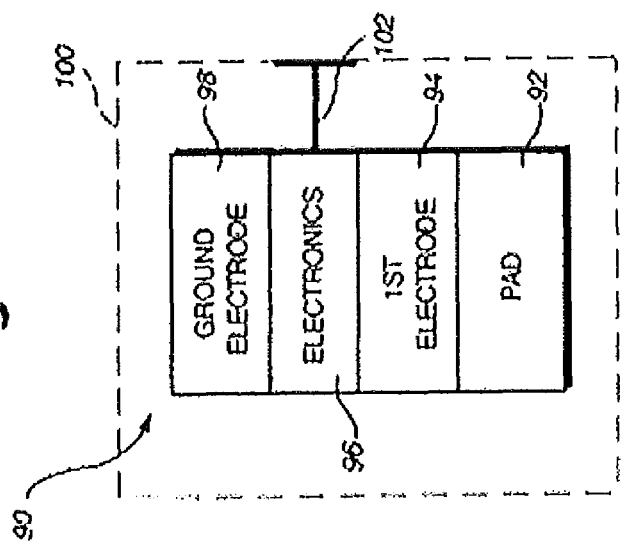

Referring now to FIGS. 11A-11C, there is provided a further form of the applicator hereof comprised of a completely self-contained disposable unit or applicator 90 integrally containing the electronic circuitry and a power source. In this form, the applicator is prepackaged for one-time usage. For example, as illustrated in FIG. 11A, the applicator 90 comprises a pad 92 for containing the medicament and, if necessary, a hydrating fluid. Overlying the pad 92 is the first active electrode 94 electrically connected to electronics 96 within the applicator and which electronics 96 includes a power supply, for example, a battery, and the necessary electronics for flowing a current of a magnitude previously discussed through the pad to electrokinetically drive the medicament into the treatment site. Overlying the electronics is a ground electrode 98, the surface of which remote from pad 92 comprises a tactile surface. Illustrated by the dashed lines is a packaging material 100, for example, plastic packaging typically employed for sterilized packages whereby the applicator 90 may be sealed within the material 100. With the medicament prepackaged within the pad 92, the user opens the package 90. In a preferred form, the applicator 90 is connected with the packaging 100 via a tab 102. By removing the applicator 90 from or opening the packaging material 100, the tab 102 uncovers the battery terminals whereby the power supply is activated, In FIG. 11A, the applicator is provided without the medicament. The user applies the medicament to the pad, hydrates the pad if necessary, and applies the applicator to the treatment site. By applying the pad directly over the treatment site and pressing a finger on the tactile surface of the ground electrode, i.e., on the opposite side of the applicator from the pad, an electrical circuit is completed through the individual's finger and body and through the first electrode, the pad and treatment site whereby the medicament within the pad is electromotively transported to the site. To facilitate good electrical connection, the ground electrode may have an electrical conducting fluid, e.g., hydrogel, overlying its tactile surface.

In FIG. 11B, the medicament is prepackaged in the pad 92. In FIG. 11C, both the medicament and the hydrating fluid is self-contained in the pad. For example, the medicament and the hydrating fluid can be provided in capsules rupturable by pressure applied between the opposite surfaces of the pad before, during or after removal of the applicator from the package 100. Further, a very weak, e.g., less than 0.05% saline solution encapsulated and integrated between the active foil electrode 94 and the medicament with or without a porous matrix reservoir interposed between the encapsulated hydration fluid and the medicament may be employed. Alternatively, adhesively attached or otherwise releasably attached seals for sealing the medicament and the hydration fluid, if necessary, to the applicator to ensure long shelf life and integrity of the foil electrode can be provided.

Additionally, the unit of FIGS. 11A-11C may have a tacky substance, e.g., hydrogel, not shown, overlying the ground electrode 98 within the package 100. Upon opening the package, the individual may contact his/her finger on the tacky substance, facilitating removal of the unit from the package 100. This finger contact on the ground electrode side of the unit also facilitates ready, direct and intuitive manipulation and application of the unit to the treatment site by the individual.

Figure 12:
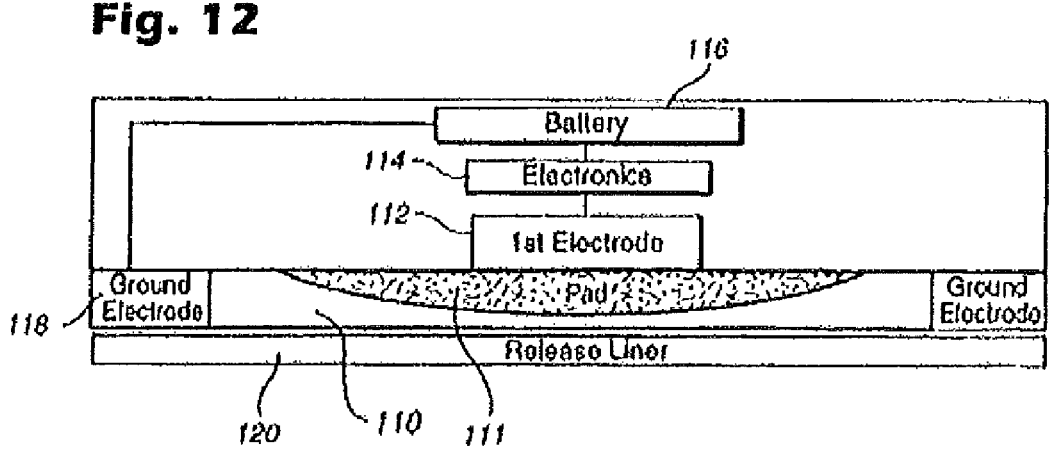
FIG. 12 is a schematic representation of an applicator in accordance with a further embodiment of the present invention.
Figure 13:
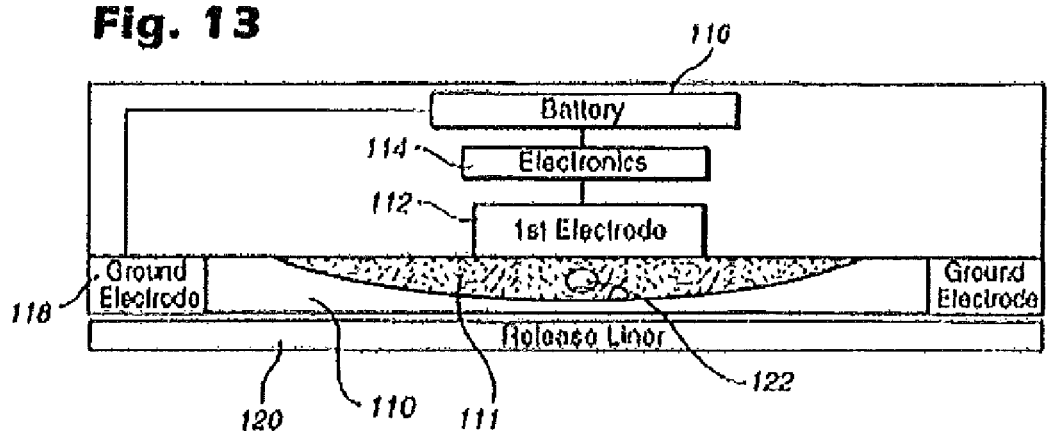
FIGS. 13 and 14 are preferred forms of the applicator of FIG. 12 with an encapsulated medicament illustrated in FIG. 13 and encapsulated medicament and hydrating fluid illustrated in FIG. 14.
Figure 14:
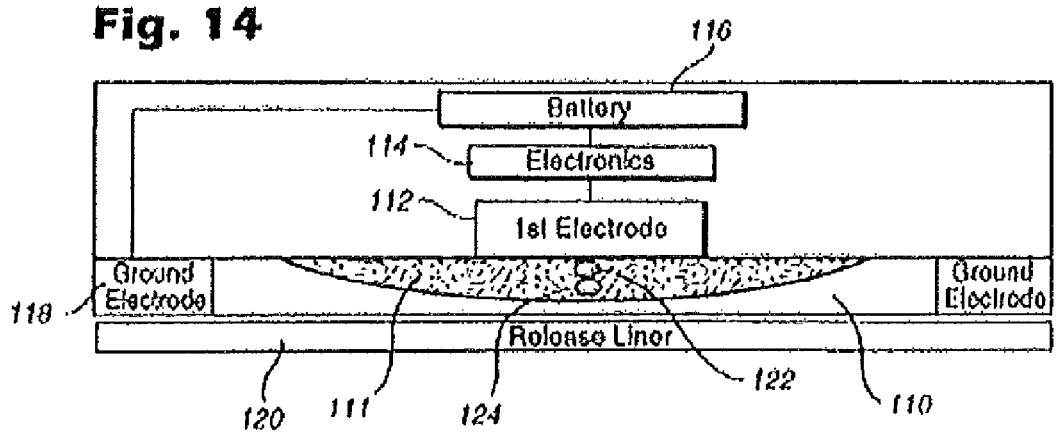

Referring now to the embodiment hereof illustrated in FIGS. 12-14, there is illustrated a further form of applicator body or substrate 110 which comprises a self-contained disposable unit having integral miniaturized electronic circuitry and a power source. In this form, the applicator may comprise a rectilinear or circular article having a centrally located pad 111 and electronic circuitry superposed over the pad. Thus, a first or active electrode 112 overlies the pad and the electronics previously described may overlie the first electrode. The battery 116 may overlie the electronics. The first terminal of the battery is connected through the electronics with the first electrode which, in turn, is in electrical contact with the pad 111. The second terminal of the battery is in contact with a ground electrode 118, The ground electrode may be provided around the margin of the applicator surrounding the pad. For example, if the applicator is shaped in the form of a circle, the ground electrode may comprise an annulus surrounding and electrically insulated from the pad 111. Alternatively, if the applicator is rectilinear, the ground electrode may comprise the margin of the rectilinear applicator or lie at one end of the applicator. In this form, the electrical circuit is completed between the ground electrode and the pad. The distance between the ground electrode and the pad may be on the order of one-half inch or more. The ground electrode need not surround the pad but may be located to one side of the pad a suitable distance from the pad for completing the return circuit path through the skin between the treatment site and the ground electrode.

In the applicator illustrated in FIG. 12, the pad may be provided without the medicament and the user may apply the medicament to the pad upon removal of release liner 120. The battery may be of the air-actuated type previously discussed. Thus, the user, upon applying the medicament to the pad and removing the tab from the battery, may apply the applicator over the lesion, holding both the ground electrode about or spaced from the treatment site and the pad in contact with the treatment site. This completes the electrical circuit through the applicator and the individual's skin between the ground contacting surface and pad contacting surface. If desired, adhesive may be provided on the underside of the applicator body 110 and overlaid by the release liner 120 to releasably adhere the applicator including the pad 111 and ground electrode 118 to the individual's skin and overlying the treatment site. Upon completion of the treatment, the applicator may be discarded.

Alternatively, as illustrated in FIG. 13, the applicator may be prepackaged with the medicament encapsulated within the pad. The capsule is indicated at 122. If the medicament is itself electrically conductive, the individual may apply pressure to the pad to rupture the capsule, spreading the medicament into the interstices of the pad. This can be accomplished while the applicator remains in its packaging. By applying the applicator to the treatment site similarly as previously described in connection with FIG. 12, the circuit is completed whereby the medicament is electrokinetically driven into the site.

In FIG. 14, both the medicament and a hydrating fluid are encapsulated in the pad. The medicament and hydration fluid capsules are indicated at 122 and 124, respectively. The applicator of FIG. 14 is employed similarly as described with respect to FIGS. 12 and 13 after the user ruptures the capsules to intermingle the electrically conductive water and the medicament.

Figure 15:
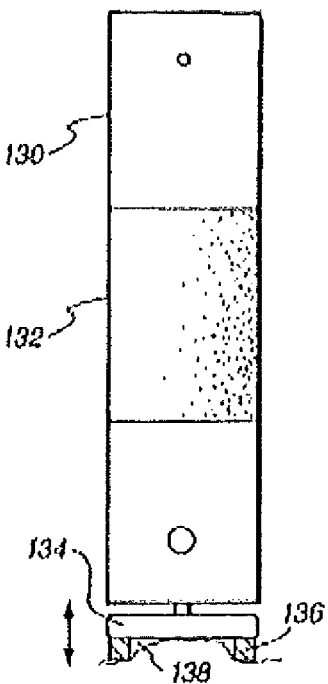
FIG. 15 is a side elevational view of a further form of the present invention.

Referring now to FIG. 15, there is illustrated a device 130 similar to the device of FIG. 1 and containing a power source, electronic circuitry including a voltage multiplier and a current driver and a tactile electrode 132 exposed through an outer surface of the device 130. Instead of having the active or first electrode fixed to the end of the device 130, the active electrode 134 is mounted on the device 130 for movement in an axial direction. The movement is designed to open or close a pressure actuated switch in the electronic circuitry to activate the device. Thus, the active electrode 134 in an outermost position maintains the electronic circuitry in an off condition. Pressure applied to the first or active electrode 134 tending to displace it toward the device housing closes the switch, activating the electronic circuitry for electrokinetic delivery of the medicament.

In this form of the invention and instead of an applicator releasably secured to an electrokinetic device, the distal face of the first electrode 134 may be provided with an electrical insulator ring 136 defining and surrounding a reservoir 138. It will be appreciated that the medicament can be supplied from an ancillary tube, jar or the like in the form of a gel, cream, foam or the like and disposed by the user into the reservoir 138 within the insulating ring 136 prior to use. With the reservoir filled with medicament, the device can be applied to the treatment site similarly as the device of FIG. 2 is applied to the treatment site. By applying a slight pressure on the device toward the treatment site, the electrical circuit is closed. Thus, the medicament within the reservoir is electrokinetically motivated into the treatment site, the electrical circuit being completed through the treatment site, with the medicament, the first electrode 134, the electronics, the tactile electrode 132 and the individual's hand and skin between the tactile electrode and the treatment site.

Figure 16:
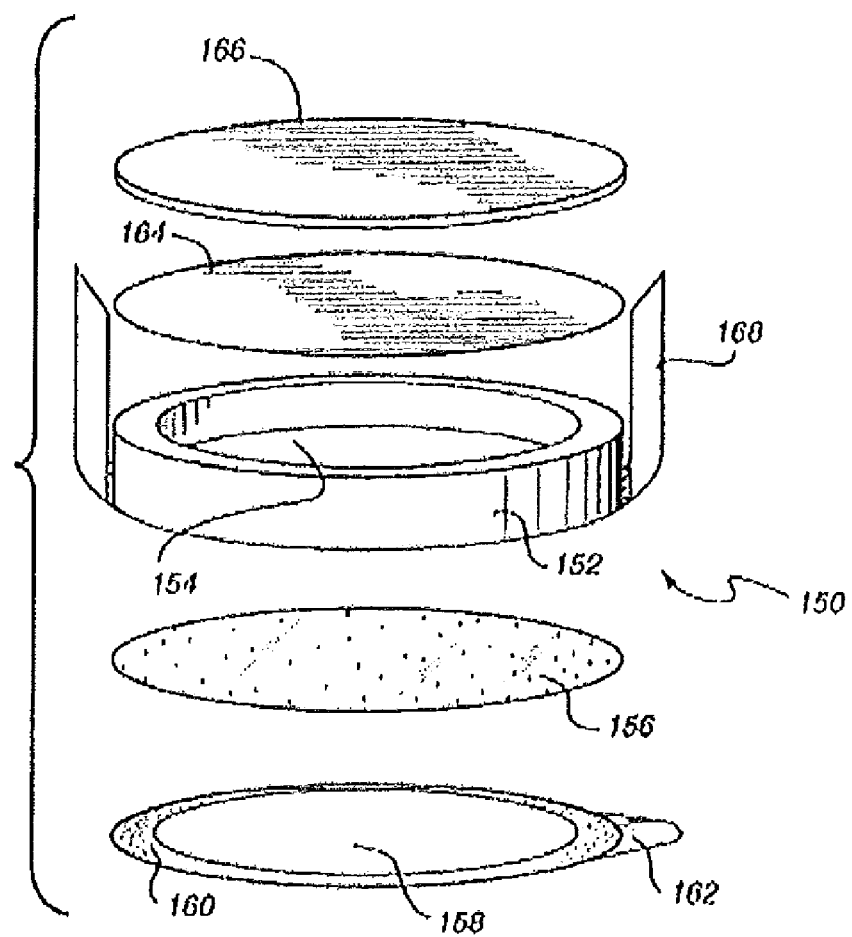
FIG. 16 is an exploded schematic view of a still further form of applicator electrode in accordance with the present invention.
Figure 17:
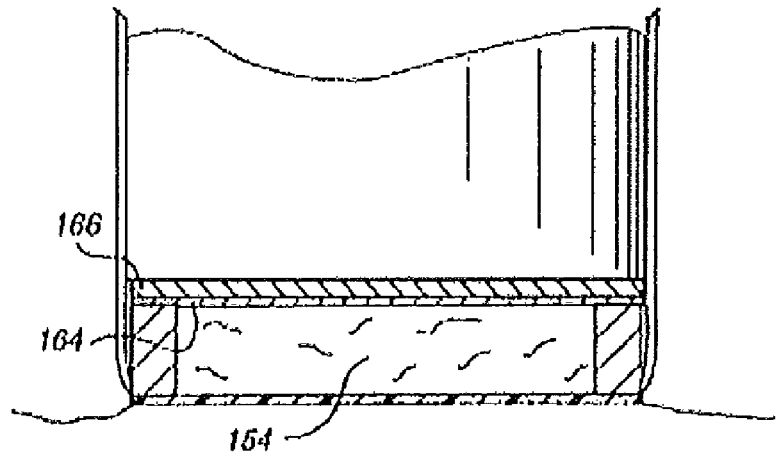
FIG. 17 is a fragmentary view of the applicator of FIG. 16 applied to the end of a device.

Referring now to FIGS. 16 and 17, there is illustrated a further form of applicator in accordance with the present invention. In this form, an applicator, generally designated 150, may be used in conjunction with the device illustrated in FIG. 1 and which applicator is particularly useful for electrokinetically delivering a liquid medicament. The applicator 150 may comprise an insulated annular housing 152 in the form of a torus having a central reservoir 154 for confining the liquid. One side of the housing 152 comprises a microporous film 156 overlaid by a barrier, e.g., foil or inert tab 158. The margin of the tab 158 has releasable adhesive 160 such that the barrier can be releasably attached to one side of the housing 152. The barrier tab includes a finger tab 162 for ready removal of the barrier 158 from the applicator. The opposite end of the reservoir 154 is closed by a similar barrier layer 164 or by an optional conductive plate 166. Additionally, tabs 168 are secured along opposite sides of the housing 152 for releasably securing the housing 152 to the device, e.g., illustrated in FIG. 1.

As illustrated in FIG. 17, the active electrode of the device bears against the optional conductive plate 166 which conducts electricity through the barrier layer 164 into the liquid medicament in the reservoir 154. Upon removal of the tab 158, the liquid medicament when applied to the treatment site can be electrokinetically driven into the treatment site through the microporous film 156. As noted previously, the liquid within the reservoir may be per se conductive or, if not conductive, may be provided with a carrier whereby the medicament can be driven through the porous membrane 156 into the treatment site.

Figure 18:
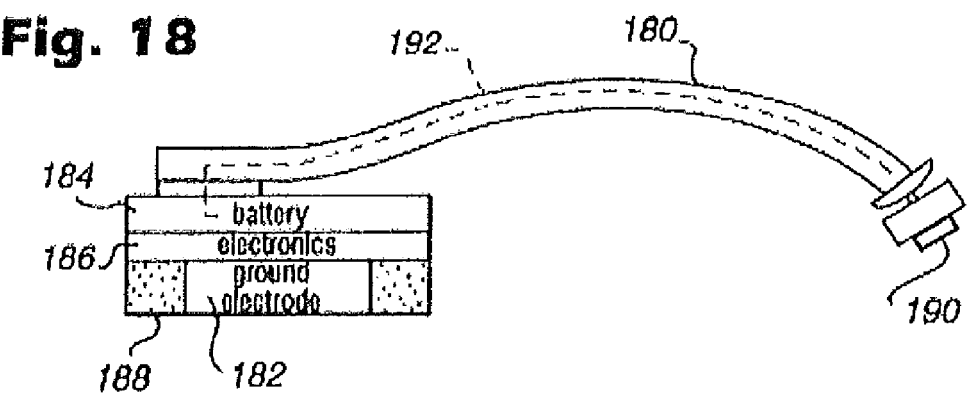
FIG. 18 is an illustration of a hands' free electrokinetic medicament delivery device.

Referring now to FIG. 18, there is illustrated a self-contained electrokinetic medicament delivery device. In this form, however, the ground electrode and the active electrode are separated one from the other by a malleable or tensionable arm 180. For example, the ground electrode 182 may be provided in a housing also containing the battery 184 and electronics 186. The ground electrode 182 may be surrounded by an adhesive 188 for adhering the ground electrode to a site on an individual directly adjacent a treatment site. The active electrode 190 is connected to the battery and electronics via an electrical conductor indicated by the dashed lines 192 through an arm 180. The arm may be flexed resiliently and retained in its flexed position. In utilizing the device of FIG. 18, the ground electrode is adhered to the individual's skin adjacent a treatment site by the adhesive 188. The arm 180 is then flexed resiliently to engage the active electrode 190 with the treatment site. By proper manipulation of the arm 180, the entire surface of the active electrode 190 may contact the treatment site thereby avoiding less than effective treatment. A biased gimbal or pivotal connection between the arm 180 and the ground electrode 182 may also be employed rather than a resilient flexible arm 180. Thus, the user may apply the device and have it operate hands' free, the electronics being activated by activation of the battery as previously described.

Figure 19:
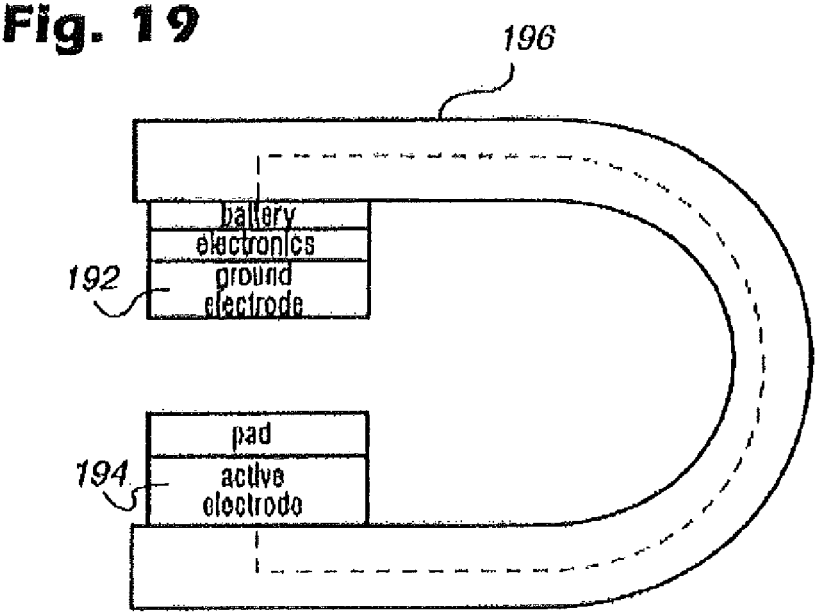
FIG. 19 is a schematic illustration of a still further hands' free electrokinetic delivery device according to the present invention.

Referring now to FIG. 19, a similar type of hands' free electrokinetic medicament delivery device is illustrated in the form of an U-shaped clip. The ground and active electrodes 192, 194 are placed at opposite distal ends of a clip 196, preferably a spring clip. By placing the electrodes on the inside of the clip, the clip may be applied to gently grip the treatment site, employing the tension of the clip to retain the clip on the treatment site whereby hands' free delivery of the medicament can be accomplished. The fully disposable U-shaped clip may have a built in unit dose applicator or may be reusable if fitted out for use with disposable applicators.

Figure 20:
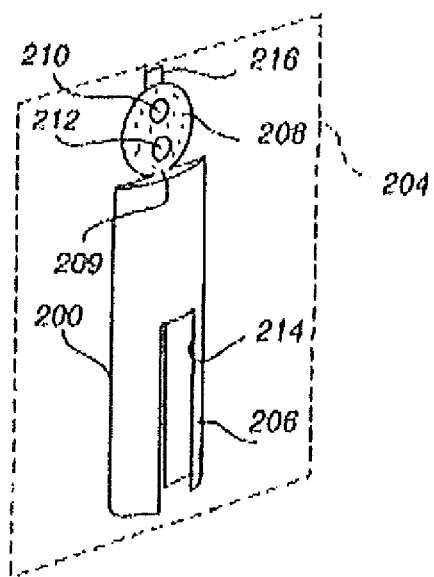
FIG. 20 is a perspective view of a further form of an applicator, illustrated with its packaging, for use with an electrokinetic delivery device.
Figure 22:
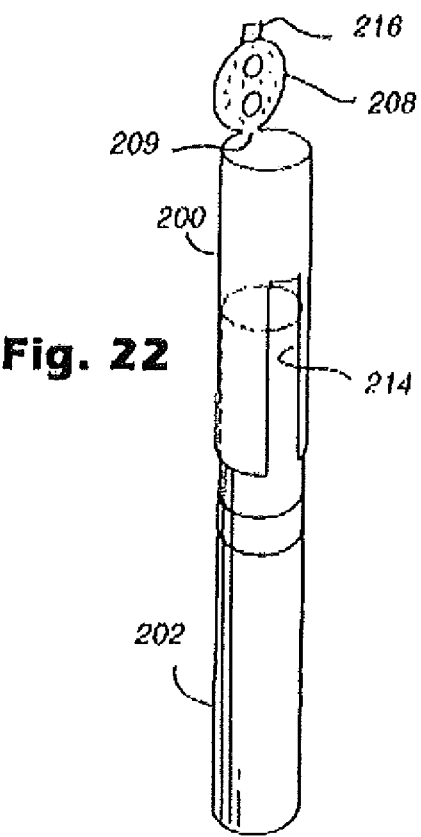
FIG. 22 is a schematic illustration of the applicator of FIGS. 20 and 21 applied to the electrokinetic device.
Figure 23:
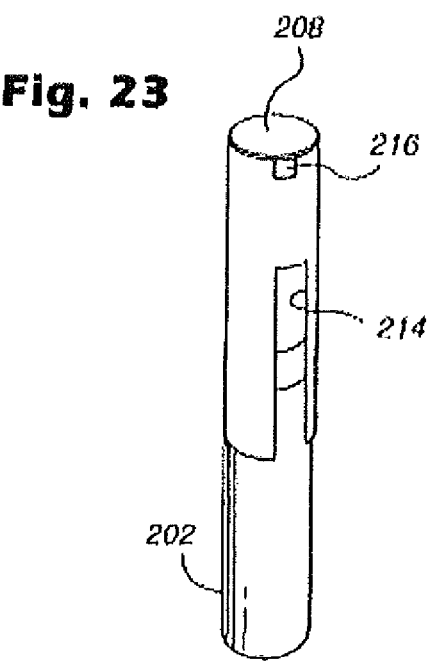
FIG. 23 is a perspective view of the device with the applicator applied ready for use.

Referring now to FIG. 20, there is illustrated a further form of an applicator 200 for use with an electrokinetic delivery device 202 (FIGS. 22 and 23) illustrated in a flat configuration and within packaging 204, for example, a plastic sealed package. Applicator 200 includes a flattened sleeve 206 open at its opposite ends and having an applicator pad 208 forming part of the sleeve and projecting from one end of the sleeve and along an edge thereof. Preferably, the applicator pad 208 is circular in form, for reasons which will become apparent and is hinged to sleeve 200 along a hinge line 209. The pad 208 is preferably a porous open cellular material through which the medicament may be transported to the treatment site. As in prior embodiments, the pad 208 may contain the medicament within the pad within the interstices of the open cellular material or the medicament may be encapsulated within rupturable capsules 210, similarly as illustrated with respect to FIGS. 7 and 8. A further alternative provides a pad without medicament, the medicament, and hydration material, if necessary, being applied to the pad by the user at the time the user employs the device to electrokinetically deliver the medicament to the treatment site. The pad 208 may additionally contain hydration material in a hydration capsule 212 similarly as illustrated in FIG. 8 in the event the medicament is not per se electrokinetically transportable.

As illustrated, the sleeve 206 is preferably formed of a fabric material similarly as the material of substrate 42. Other suitable materials may be employed forming all or part of the sleeve, i.e., the substrate of any of the applicators disclosed herein may include, polyethylene, paper, cotton, ceramic, silicone rubber, polyurethane, vinyl, polytetrafluoroethylene and other plastics. A suitable barrier may be disposed between the pad 208 and the sleeve 206 to prevent migration of the medicament onto the sleeve or migration of any electrically conductive material such as hydrogel as noted below from the sleeve 206 onto the pad 208. Opposite sides of the sleeve 200 may have cutouts 214 which open through the end of sleeve 206 opposite the pad 208 or which may be completely enclosed cutouts. Particularly, the cutouts 214 lie at circumferential positions about the sleeve 206 corresponding to the axial and circumferential positions of the tactile electrode, for example, electrode 30 as illustrated in FIG. 1. Additionally, a tab 216, preferably having a pressure sensitive adhesive on one face, projects from the pad 208 opposite from its connection with the sleeve 206.

To use the applicator 200 in conjunction with the electrokinetic delivery device 202, the packaging 204 is removed from the applicator 200. Where the medicament is encapsulated, the pad may be compressed between the individual's fingers to rupture the capsule 210 and hence spread the medicament into the interstices of the pad. Where the medicament is not per se capable of electrokinetic transport, the hydration capsule 212 is likewise ruptured to mix the medicament and hydration material such that upon application of electric current, the medicament may be transported to the treatment site. If, of course, the medicament has previously been applied to the pad, the user need not compress the pad. Alternatively, if the pad contains no medicament, the user may apply the medicament to the pad and hydration material, e.g., water or a trace saline solution, if necessary.

Figure 21:
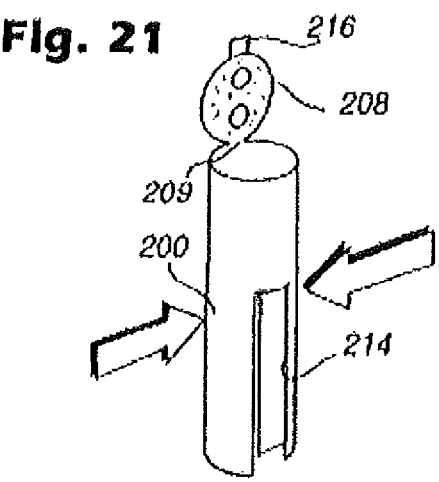
FIG. 21 is a view of the applicator of FIG. 20 without its packaging.

As illustrated in FIG. 21, pressure applied in the direction of the illustrated arrows will form the flat applicator sleeve 206 into a cylinder for reception about the end of the electrokinetic delivery device mounting the active electrode, for example, the device illustrated in FIG. 1. Upon application of sleeve 206 to the device 202, the cutouts 214 are aligned with the tactile electrode along the sides of the device 202. Additionally, the pad 208 is folded over the active electrode at the end of the device 202 and the adhesive tab secures the pad 208 in contact with the active electrode. The user may then grasp the device 202 with the user's fingers pressed against the tactile electrode of the device 202 to complete the electrical circuit, as previously described. It will be appreciated that the sleeve 206 may have, instead of cutouts 214, areas impregnated with hydrogel to facilitate electrical contact between the individual's fingers and the tactile electrode of the electrokinetic delivery device. In any embodiment, auxiliary hydration material, e.g., water may be employed. The sleeve may also contain magnetic switch activation material. After application of the device illustrated in FIG. 23 to the treatment site, the user removes the applicator 200 from the end of the device 202 and discards the applicator. The device 202 remains for subsequent use with a similar applicator or other applicators disclosed herein.

The above mechanisms may be monopolar or multi-channel (as in U.S. Pat. No. 5,160,316, now U.S. Pat. No. Re. 36,626, incorporated herein by reference), or hybrid multi-channel in nature. By hybrid multi-channel it is meant that only one current driver is employed while more than one current limiter is employed to a corresponding number of two or more current distributive channels. A potential problem which may possibly be encountered with hand-held, electrokinetic devices, e.g., iontophoretic devices, is non-uniformity in contact pressure between the treatment surface and the active electrode surface. For a self-medicating patient using a probe-type iontophoretic device, if the probe is accidentally held at an oblique angle, non-uniform contact pressure occurs. In the small area where the contact pressure is high, the local electric resistance is low and therefore more current flows in this small area. The resulting current concentration not only prevents a uniform delivery of medicament but also can cause discomfort and even burns due to a high local current density. This detrimental occurrence can be prevented (for example, by using a multi-channel design (segmented electrode). As the contact pressure becomes uneven, the resistance of each channel or segment varies. For small changes in contact pressure and resistance, the current flowing in each channel remains constant due to servo control. However, the bias potential or voltage of each channel will change. For an area with higher contact pressure, and therefore lower resistance, the bias potential will decrease. Based on this decrease in bias potential, an early warning signal for uneven probe placement can be generated and transmitted to the patient for readjustment. If this warning is ignored, and the pressure concentration deteriorates further, some channel will reach its maximum bias potential limit and the current and the concomitant medicament delivery will decrease from the pre-set level. For the channels where the contact pressure is high and resistance is low, the current remains constant (due to servo control of the current) in spite of the reduction in resistance. This is one of the benefits of a multi-channel system where current density remains unchanged under each segmented electrode. The non-uniform contact pressure can still cause global non-uniform medicament delivery but not burns.

Figure 24:
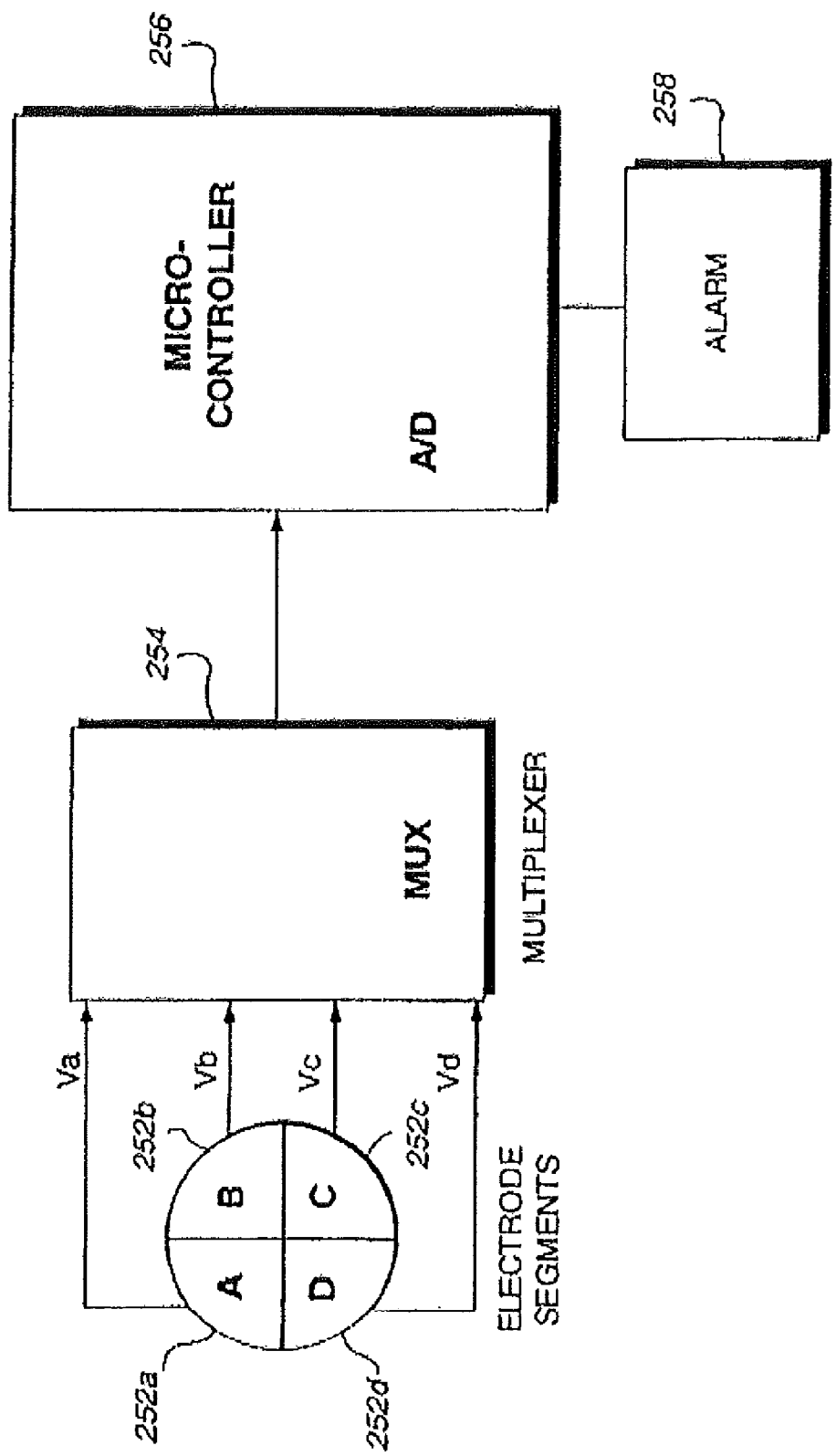
FIG. 24 is a schematic representation of an alarm system for misplacement of the probe.

An example of how the presence of non-uniform contact pressure can be detected is illustrated in FIG. 24. For ease of explanation, assume that the treatment electrode is divided into four segments 25a-d as shown in FIG. 24. Treatment currents in equal amounts, flow to electrode segments 252a-d, respectively. The current components are maintained by separate servo control loops to remain constant, irrespective of the skin and medicament conductivity, by varying the bias potential of each electrode segment. Under normal conditions in which the contact pressure is uniform, the bias potentials, Va, Vb, Vc and Vd for respective segments are substantially equal.

As shown in FIG. 24, the bias potential of each segment is connected to an analog multiplexer 254, the output of which is, in turn, connected to an analog-to-digital (A-to-D) channel of a micro-controller 256. Micro-controller 256 is an IC including a microprocessor core with digital inputs, outputs, A-to-D converter, timer, and other functional elements. The microprocessor can be programmed to conduct many diverse tasks. It can also be programmed, for example, to periodically measure and compare the bias potential of each electrode segment. If, for example, Va and Vb are found to be greater than Vc and Vd by a predetermined margin, the electrokinetic probe may be determined to be tilted downward by the patient such that the contact pressure is higher under segments C and D, and lower under segments A and B. The micro-controller can cause an alarm 258 to output an aural and/or visual alarm when the non-uniformity in contact pressure (as determined from the bias potentials) exceeds some predetermined value. Instead of using a micro-controller, the non-uniform pressure detection can also be accomplished by using discrete analog circuitry with operational amplifiers, comparators etc.

Fungal infestations of skin and its appendages are also quite common and multiple therapies are available. The infections afflict age groups from childhood to late adulthood and the aged and immune suppressed population. The infections may include, for example, diaper rash, athlete's foot or jock itch and, in children, ringworm and other dermatophytosis. The current treatment of such infections involve anti-fungal agents applied topically. In healthy patients, the topical treatment works, although sometimes frustrating in its response time and chances for recurrence.

Fungal infections of the nail bed are more refractory to standard management. These frequently distort the nails both on the feet and hand and commonly occur in people working in gardens. These infections create deformity of the nails and patients frequently ask for treatment. Unfortunately, the current treatment involves systemic drugs that have significant liver toxicity as well as side effects. Many patients fail to undergo the typical eight weeks of treatment required to control such infections.

As described herein, the present invention offers a more rapid resolution of topical infections and more effective non-systemic treatment of the more refractory nail infections. As in the prior embodiments, the treatment method and apparatus for fungal infestation employs an electrokinetic, e.g., iontophoretic transport mechanism including electronics to drive the medicament into the infected (treatment) site to ultimately prevent the fungus from replicating. There are numerous medicaments available on the market for this purpose. In addition, there are several non-pharmaceutical level agents that may have a significant benefit to the treatment of fungal infections.

Figure 25:
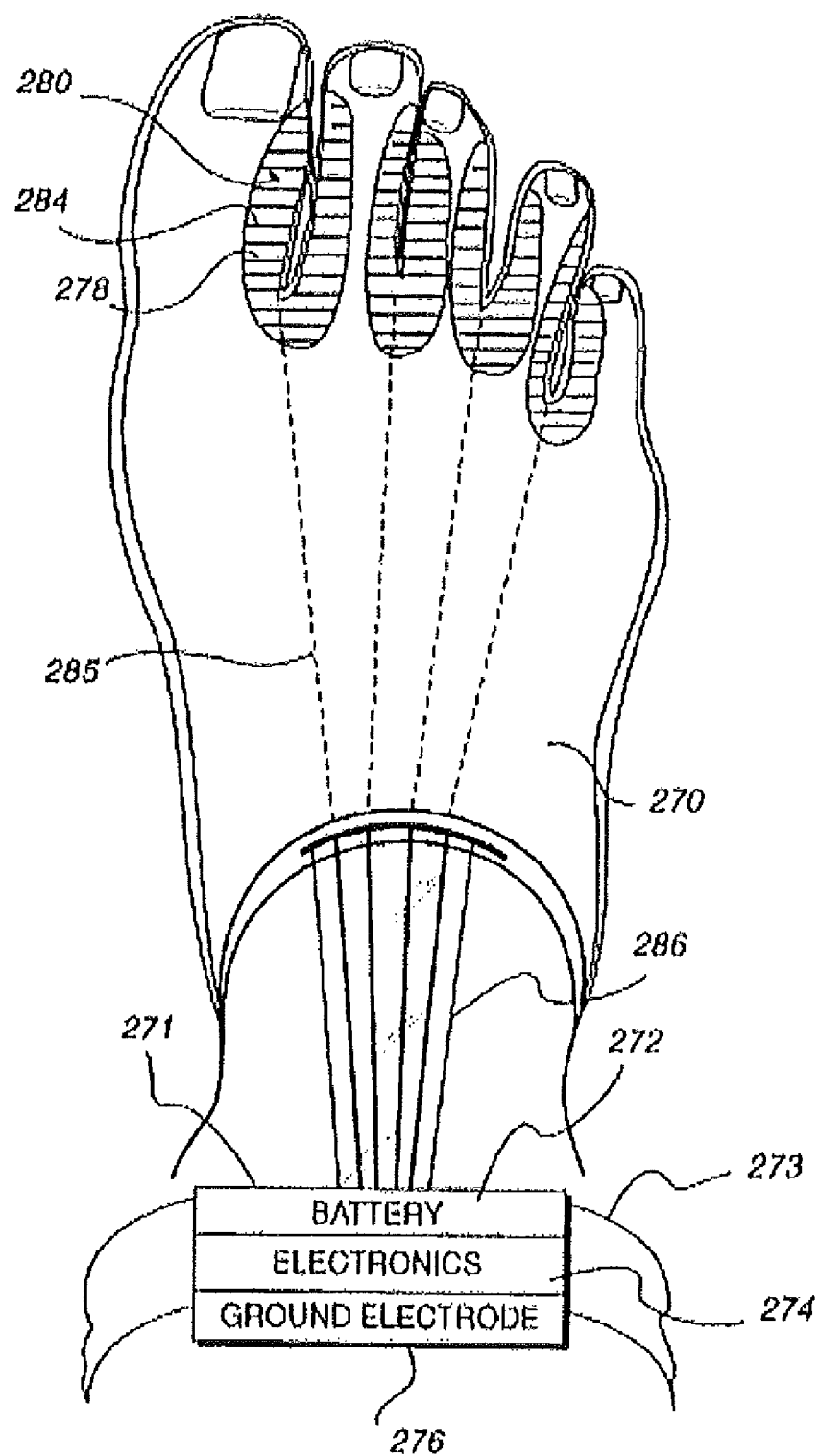
FIG. 25 is a schematic illustration of an electrokinetic applicator in the form of a sock for treatment of fungal infestations between the toes.

Referring to FIG. 25, there is illustrated an applicator 270 for the treatment of athlete's foot, e.g., where fungal infestation occurs between the toes. The applicator 270 is in the form of a flexible elastic sock electrode with an electronics package 271 containing a battery 272, electronics 274, ground electrode 276 and active electrodes 278 in registration with fungal infested areas between the individual's toes. The package 271 is strapped about the individual's ankle by a strap 273. Discrete medicament-carrying pads 280 are shaped to extend between the toes along the interior portion of the toe region of the sock. Individual branch wires 284 overlying the pads 280 and with an electrically insulative covering, not shown, are coupled to the electronics package by conductive wire leads 285 disposed in an insulative protective ribbon 286. By wearing the sock, e.g., one to two hours, and completing the circuit between each active electrode 284 and the ground electrode 276 through the individual's ankle, a single treatment is sufficient to drive the anti-fungal medication carried by the pads 280 into the infected area between the toes to completely resolve the fungal infestation. It will be appreciated that the pads may form an integral part of the elastic sock 270 preferably along the inside portion of the toe region. The medicament is preferably pre-supplied within the pads, e.g., encapsulated and with or without hydration material as in prior embodiments hereof, The sock 270 may also be disposable with the electronics package 271 or the electronic package may be disconnected and reconnected to one or more additional socks as needed for applying additional medicament at the appropriate treatment intervals.

Figure 26:
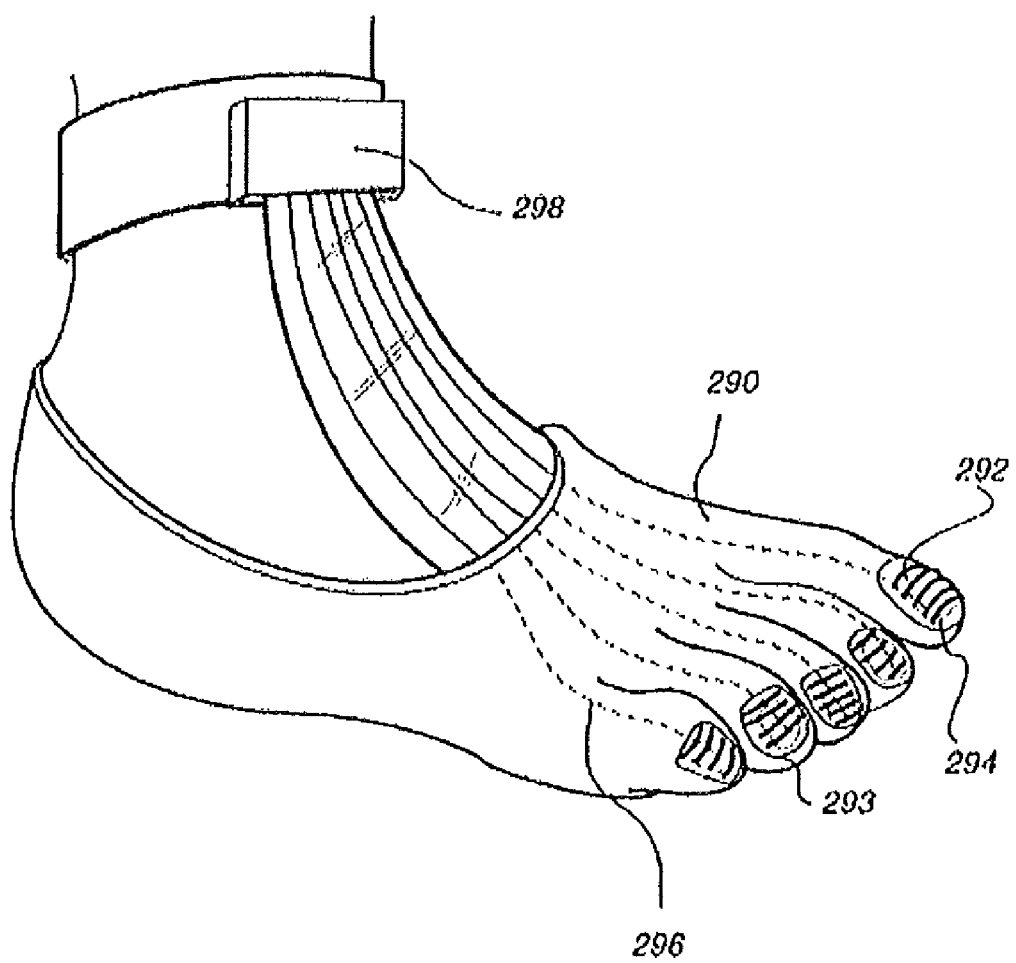
FIG. 26 is a view similar to FIG. 25 illustrating an electrokinetic applicator for treatment of a nail bed fungal infestation.

A similar arrangement is illustrated in FIG. 26 for electrokinetic application of medicaments to toenail fungal beds. In this form, the elastic sock 290 includes active electrode portions 292 overlying a pad 293 containing the anti-fungal agent in the region of the sock overlying the individual toenails. Each active electrode portion 292 may comprise short individual lead wires 294 coupled via individual leads 296 to an electronics package 298 similar to the package described and illustrated with respect to FIG. 25. Thus, electrokinetic delivery of the medicament to the nail beds of the toes is provided upon completion of the circuit through the active electrodes 294 and ground electrode in the electronics package 298 through the ankle of the individual. This treatment requires prolonged and overnight wear of the sock electrode and may involve a plurality of treatments, for example, three treatments with a spacing of about two or three days.

Referring now to FIGS. 27 and 28, there is illustrated an applicator for the treatment of fingernail fungal beds. In this form, an applicator body 300 may be generally hemispherical in shape and is preferably formed of a resiliently elastic material. In the arcuate surface of the hemispherically-shaped body 300, there is provided one or more fingerholes 302 into which the individual's fingernails may be received, e.g., up to about the first finger joint. Thus, five fingerholes 302 can be provided at various positions about the body 300 consistent with the anatomical orientation of an individual's bent fingers when his/her hand rests on the arcuate upper surface of the body 300 enabling the fingertips to be received in the openings 302.

As best illustrated in FIG. 28, the body 300 includes an active electrode 304 in each of the openings 302 at a location in registration with, i.e., opposite, the fingernail of the individual's finger when received in the hole. A medicament-containing porous pad, for example, in the form of a thimble 306, preferably pre-supplied with medicament or having encapsulated medicament along a forward edge thereof is provided. Alternatively, the individual user may apply the medicament to the thimble pad portion upon use. The thimble 306 may also contain a resilient elastic material 308, for example, sponge material, such that upon placing the thimble about the individual's fingertip and the fingertip including thimble 306 in the hole 302, the sponge material 308 biases the individual's nail forwardly into contact with the forward-most pad portion of the thimble to make electrical contact with the active electrode 304. As in the prior embodiments, hydrating material may also be supplied integrally with the thimble, for example, in the form of encapsulated hydration material or the individual may hydrate the medicament in the thimble pad portion upon use.

As illustrated in FIG. 28, the ground electrode 310 is provided along an arcuate surface of the body 300 such that when the individual lays his/her hand over the arcuate portion of the body 300, the palm of the hand rests against ground electrode 310 with the finger or fingers in the holes 302 bearing against the pad 306 and active electrodes 304. It will be appreciated that each hole 302 has an active electrode 304 associated with that hole. The active and ground electrodes are coupled to the electronics 312 which, in turn, is coupled to a power source 314 integral with body 300. It will be appreciated that the body 300 may have other shapes, for example, an elastic spherical shape, such that the individual can carry the electrokinetic delivery device in his/her hand for the duration of the treatment period. Alternatively, as illustrated, the body 300 may have a flat undersurface enabling the individual to rest his/her hand on the upper arcuate surface of the body 300 with body 300 supported, for example, on a desk or table.

As will be appreciated from the above description, a variety of active electrodes can be designed for size and contour for application to various parts of the human body. For example, electrodes can be woven into undergarments to alleviate refractory infestation in the inguinal area, commonly described as jock itch. Moreover, applicators such as the sock electrodes described, are disposable items with prescribed medication pre-supplied for specific application.

Figure 29:
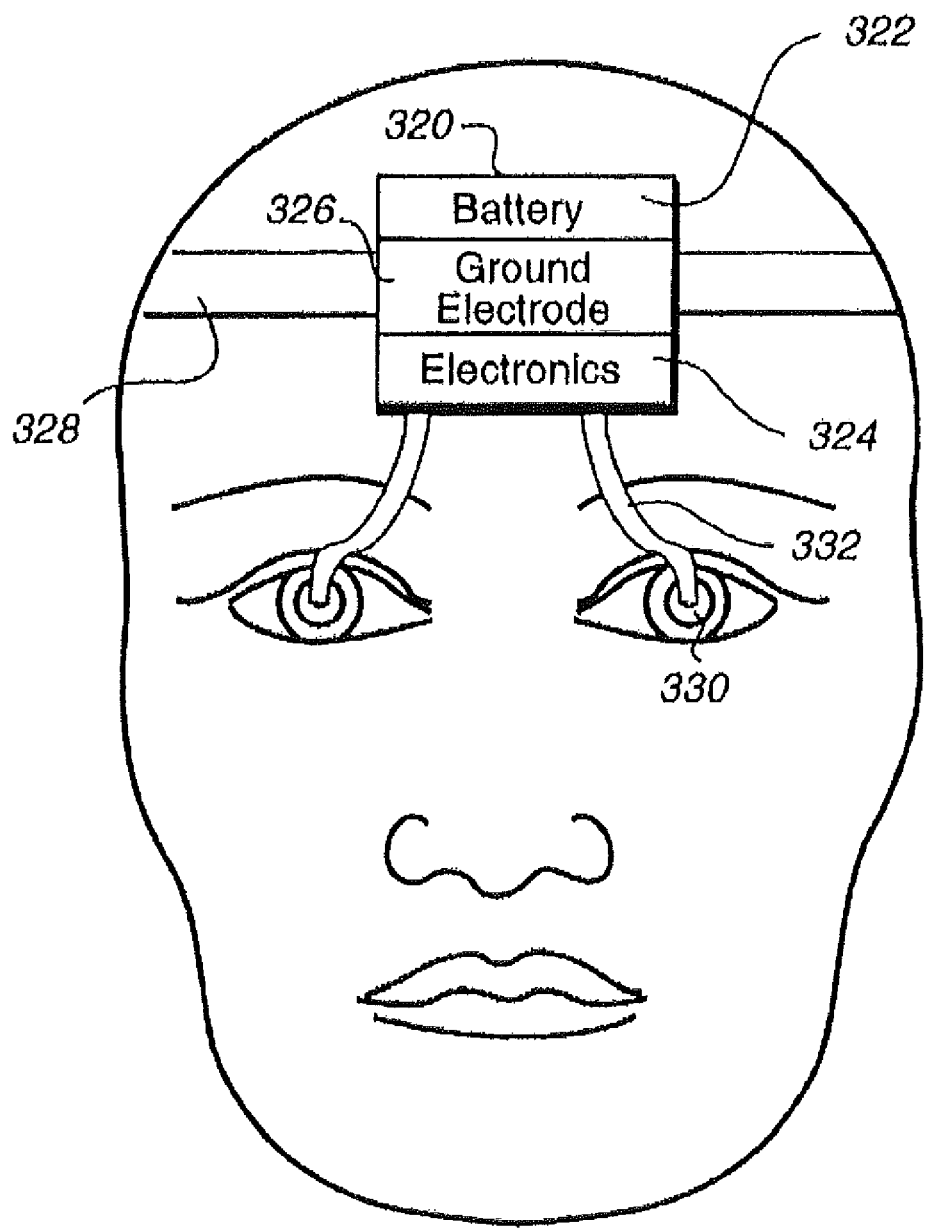
FIG. 29 is a schematic representation of a device for electrokinetic ocular treatment.
Figure 30:
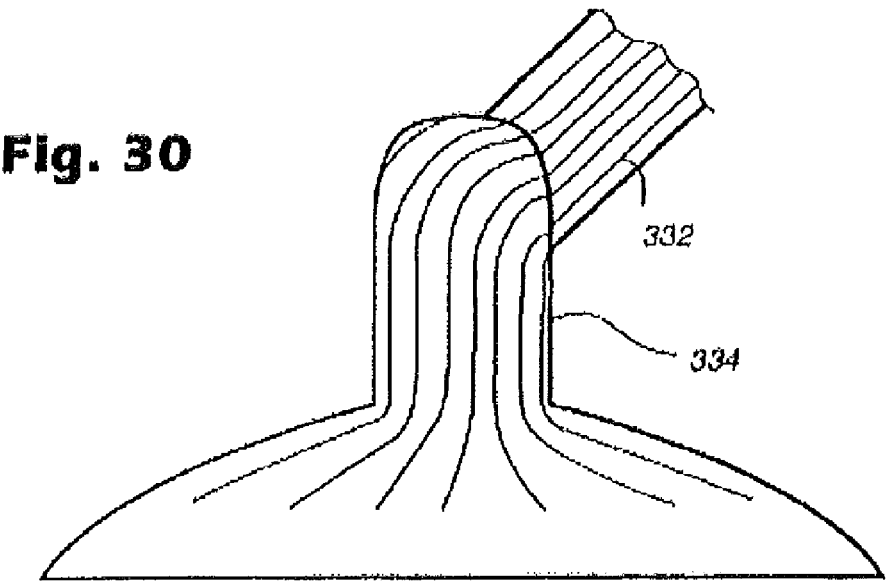
FIG. 30 is a side elevational view of an ocular applicator according to this aspect of the invention.
Figure 31:
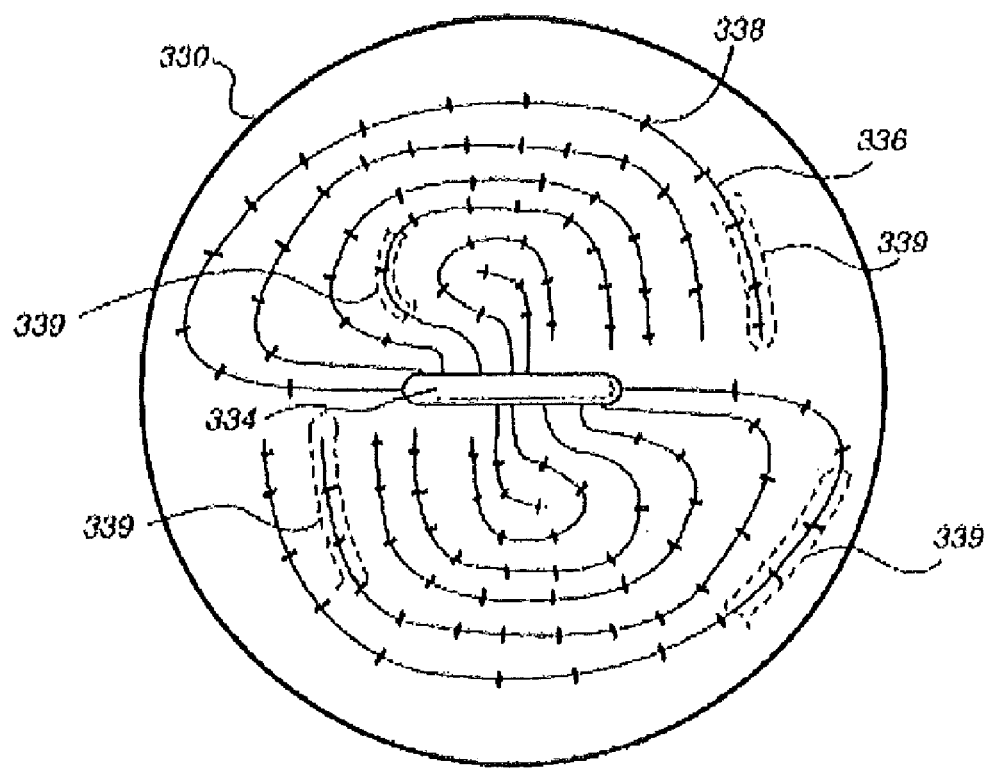
FIG. 31 is a planar view of the ocular applicator illustrating the multi-channel conductors.

Referring now to the embodiment hereof illustrated in FIGS. 29-31, various medicaments may be electrokinetically applied in an ocular application similar to and worn like a contact lens. For example, as illustrated in FIG. 29, there is provided an electronics package 320 comprised of a battery 322, electronics 324 and a ground electrode 326 carried by a strap 328 designed to envelope the individual's head releasably securing the electronics package 320 on the forehead with the ground electrode engaging the individual's forehead, Contrary to the preceding embodiment, the mechanism of the electrokinetic delivery may be a multi-channel electrode as described in U.S. Pat. No. 5,160,316, now U.S. Pat. No. Re. 36,626, incorporated herein by reference. While delivery of medicament is illustrated as being applied to both eyes simultaneously, it will be appreciated that the electrokinetic delivery system hereof can be applied to only one eye.

As illustrated, the electronics of the package 320 are coupled to an applicator electrode 330 for each eye via a ribbon cable connector 332. The applicator electrodes 330 are each in the form of a concave-convex matrix formed of electrodispersive material sufficiently flexible to fit and overlie the various contours of individual eyes. Each matrix is similar to a contact lens. Applicator electrode 330 includes a combined handle and connector 334 which projects from the convex side of the applicator electrode 330, facilitating a finger grip for the contact electrode 330 and an electrical connection for the ribbon connector 332. The individual lead wires in the ribbon connector 332 are continued through the combined handle and connector 334 into the electrode 330. As illustrated in FIG. 31, these individual conductors or lead wires 336 extend from the combined handle and connector 334, preferably in semi-circular patterns along opposite halves of the contact electrode 330. Each of the conductors 336 has a plurality of short lead wires or supplemental conductors 338 at spaced positions along each connector 336 to provide increased contact area, i.e., to further distribute the electrical current flow along the surface of the eye. Each of the lead wires or connectors 336 has a discrete pad 339 associated with it for carrying the medicament and which medicament is electrokinetically driven into the eye upon completion of the electrical circuit between the applicator electrode 330, the eye, the individual's skin between the active and ground electrodes, and the ground electrode 326.

As noted in the aforementioned patent, the lead wires 336 in each contact electrode 330 may be electrically driven simultaneously or in sequential multiplex fashion. With the current in each connector 336 being limited, for example, within the range previously discussed, current tunneling or current flow along the path of least resistance is substantially eliminated. For delivering medicaments, the ocular electrokinetic delivery system described herein is preferably worn by an individual over a period of time, for example, up to an hour, with the multi-channel driver electrokinetically delivering the medicament into the cornea. Further, the contour of the eye can be reshaped by delivering agents that retain water which would swell the conjunctiva in specific sites of the eye. By applying differential levels of power and agent delivery through use of a multi-channel system, the refraction of light can be modified by altering the shape of the eye.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

B. Method and System for Electrokinetic Delivery of a Substance

The present invention is described in the context of exemplary embodiments. However, the scope of the invention is not limited to the particular examples and embodiments described in this specification. Rather the specification merely reflects certain embodiments and serves to illustrate the principles and characteristics of the present invention. Those skilled in the art will recognize that various modifications and refinements may be made without departing from the spirit and scope of the invention. A method and system for the safe application of an electrokinetic delivery system, such as iontopheresis, is described with reference to FIGS. 32 through 35. The method and system are based on the use of a high frequency rectified current in conjunction with three electrodes, referred to herein as a treatment electrode, a counter electrode and an auxiliary electrode. For purposes of illustration, transdermal delivery of morphine is used as an example. It will of course be appreciated that the method and system described herein are usable in connection with substances generally including natural or homeopathic products that may be outside the definition of medicaments as well as medicaments (e.g., lidocaine for transdermal anesthetization, anti-viral agents for herpes infections, and anti-fungal medicine for athlete's foot) and in connection with barriers other than skin (e.g., cell membranes, mucosal membranes, etc.).

By medicament is meant any chemical or biologic that may be used on or administered to humans or animals as an aid in the diagnosis, treatments or prevention of disease or other abnormal or cosmetic condition or for the relief of pain or to control or improve any physiologic or pathologic condition.

Figure 32:
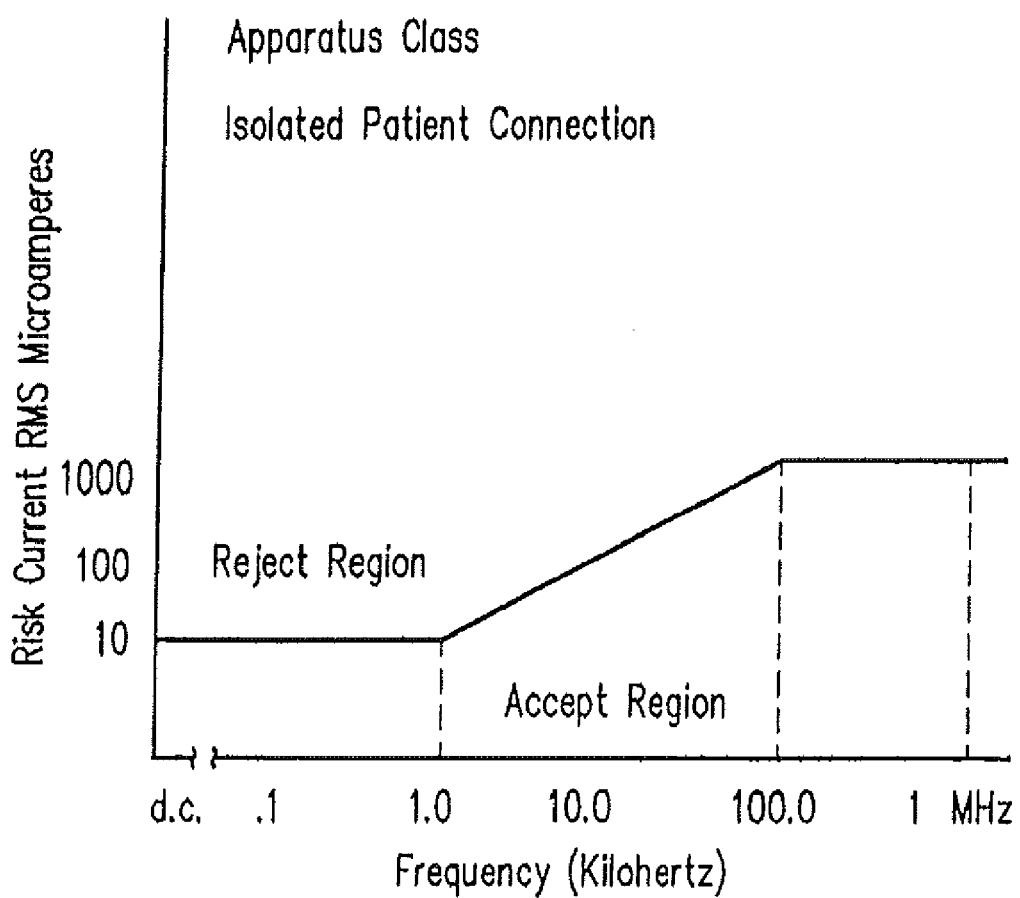
FIG. 32 is a graph of risk current (RMS) in microamperes versus frequency showing the risk current limits based on fibrillatory thresholds.

As described above, iontophoresis involves the use a current to deliver a substance to tissue. In conventional systems, there is a potential hazard associated with ventricular fibrillation and cardiac arrest if the current generated during iontophoresis accidentally passes through the patient's heart. The standard current threshold for ventricular fibrillation risk increases with frequency. FIG. 32 is a graph of risk current (RMS) in microamperes versus frequency showing the risk current limits based on fibrillatory thresholds. For direct current (DC), the limit is 10 microamperes. For frequencies from 1 kilohertz to 100 kilohertz, the risk current limit varies from 10 microamperes to 1 milliampere. For frequencies above 100 kilohertz, but below 1 megahertz, the risk current limit remains at 1 milliampere. See, for example, AAMI (Association for the Advancement of Medical Instrumentation) Standard, "Safe Current Limits Standard."

Figure 33:
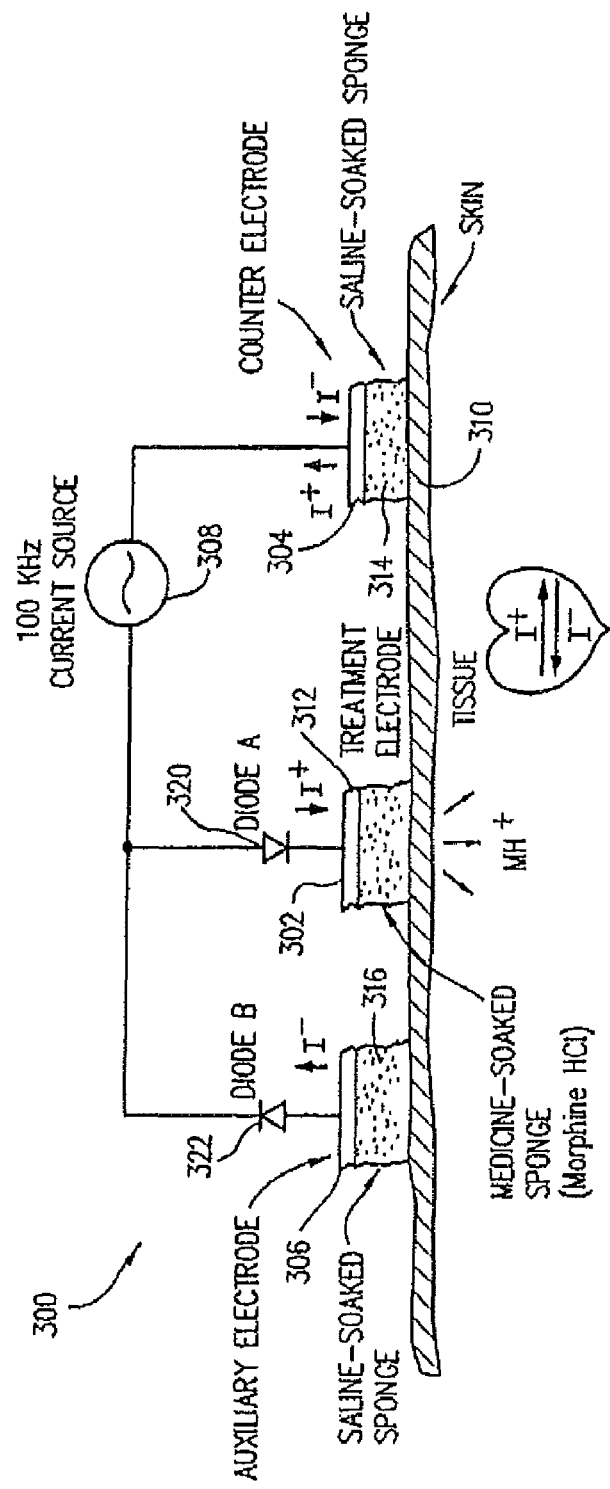
FIG. 33 shows an iontophoretic delivery system 300 in accordance with an embodiment of the present invention.

FIG. 33 shows an iontophoretic delivery system 300 in accordance with an embodiment of the present invention. System 300 includes a treatment electrode 302, a counter electrode 304 and an auxiliary electrode 306 connected to a 100 kilohertz alternating current source 308. Electrodes 302, 304 and 306 are in electrical contact with the patient's skin via conductive layers 312, 314 and 316, respectively. Such layers may, for example, be part of a medicament-carrying substrate or pad. The medicament-carrying substrates or pads are generally disposable and non-reusable and may be releasably adherable to the patient's skin and/or to electrodes 302, 304 and 306. Conductive layer 312 is shown in FIG. 33 as comprising a medicament-soaked sponge or other porous open cellular material, such as cotton, and conductive layers 314 and 316 are shown in FIG. 33 as each comprising a saline-soaked sponge or other such material.

For example, conductive layer 312 may be of a mesh-like construction having vertical cells dimensioned to accommodate a viscous fluid within the confines of the cellular structures. The viscous fluid contained within the plurality of cells includes a medicament that is in a form suitable for transport under the influence of an electric current. Conductive layers 314 and 316 may be mesh-like tactile conductive portions that contain an electrically conductive gel or fluid therewithin. Each of the conductive layers has a lower skin-facing surface and an upper electrode-facing surface. The cells form apertures between the lower skin-facing surface and the upper electrode-facing surface. The device-facing surfaces of the electrodes may further include an adhesive layer applied thereto for suitably releasably adhering the electrodes to the iontophoresis device.

Auxiliary electrode 306 is located lateral to, behind or near treatment electrode 302. Auxiliary electrode 306 and treatment electrode 302 can be in close proximity to each other and the area of auxiliary electrode 306 can be very small compared to the area of treatment electrode 302. These features permit design of a compact hand-held unit in spite of the addition of an auxiliary electrode. In one particular implementation, the total area can be reduced to a minimum by placing auxiliary electrode 306, in the form of a metal mesh, in front of treatment electrode 302. The open mesh allows free passage of medicament and ions to and from treatment electrode 302. Of course, auxiliary electrode 306 may be positioned elsewhere and the present invention is not limited in this respect.

Treatment electrode 302 is connected to AC source 308 via a current path including a first rectifying element 320 for passing current flowing from AC source 308 to skin (and tissue) 310 and blocking current flowing from skin (and tissue) 310 to AC source 308. In the illustrative FIG. 33 embodiment, first rectifying element 320 is a diode having its anode connected to AC source 308 and its cathode connected to treatment electrode 302. Auxiliary electrode 306 is connected to AC source 308 via a current path including a second rectifying element 322 for passing current flowing from skin (and tissue) 310 to AC source 308 and blocking current flowing from AC source 308 to skin (and tissue) 310. In the illustrative FIG. 33 embodiment, second rectifying element 322 is a diode having its anode connected to auxiliary electrode 306 and its cathode connected to AC source 308. Counter electrode 304 is connected to AC source 308 via a bi-directional current path over which current can flow from AC source 308 to skin (and tissue) 310 and from skin (and tissue) 310 to AC source 308.

In use, treatment electrode 302, counter electrode 304, auxiliary electrode 306 are placed in electrical contact with skin 310 via conductive layers 312, 314 and 316, respectively. Conductive layers 312, 314 and 316 may be releasably attached to the electrodes and/or to skin 310 using, for example, a releasable adhesive. Iontophoretic system 300 is then turned on using, for example, a switch (not shown in FIG. 33). During the positive cycle portions of AC source 308, a component current Lsup.+ flows from treatment electrode 302 to the patient's skin and tissue and from the patient's skin and tissue to counter electrode 304. In this way, for example, morphine HCL ions (MH+) are delivered to the tissue covered by the patient's skin. During the negative cycle portions of AC source 308, a component current I.sup.+ flows from counter electrode 304 to the patient's skin and tissue and from the patient's skin and tissue to auxiliary electrode 306.

Figure 34:
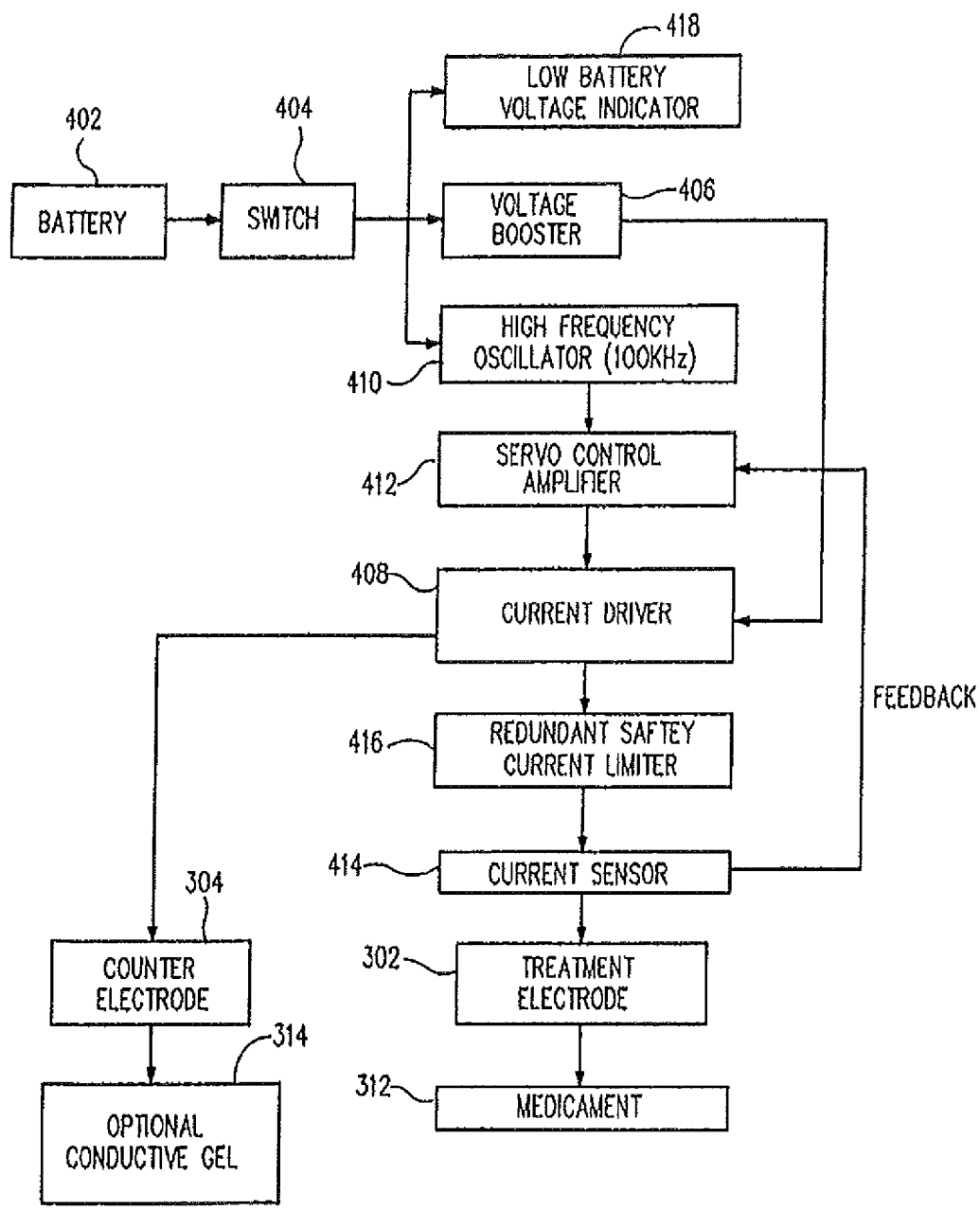
FIG. 34 shows a block diagram of electrical circuit elements of an embodiment of the present invention.

FIG. 34 is a block diagram showing electronic circuit design elements used in an illustrative implementation of a high frequency unidirectional iontophoretic medicator in accordance with an embodiment of the present invention. In this example, power source 402 is a battery comprising one or more AAA-sized primary cells connected either in series or in parallel. Counter electrode 304 is connected to an output of current driver 408 (see FIGS. 34 and 35). An optional conductive layer 314 (such as a conductive gel or a saline-soaked sponge) is used to facilitate current flow to and from the patient's skin. An internal mechanical or electronic switch 404, activated externally by a magnet or magnetic material 520 (see FIG. 35), controls the on and off status of the device. A voltage booster circuit 406 converts the low battery voltage (e.g., 1.5 to 3 VDC) to a high voltage around 30 VDC. The high voltage or high potential is preferred to allow a current driver 408 to overcome any tissue resistance. An oscillator circuit 410 generates a square-wave or sinusoidal AC signal with the selected operating frequency (e.g., 100 kilohertz). A servo-controlled amplifier 412, in synchronization with the oscillator signal, controls the current magnitude based on current feedback signals from a current sensor 414. A current driver stage 408 controls the bias voltage and maintains the desired current to treatment electrode 302. A redundant current limiter 416 is used to provide a safe upper limit for the treatment current. A low battery voltage indicator 418 (e.g., an LED) signals when the battery capacity is low.

Figure 35:
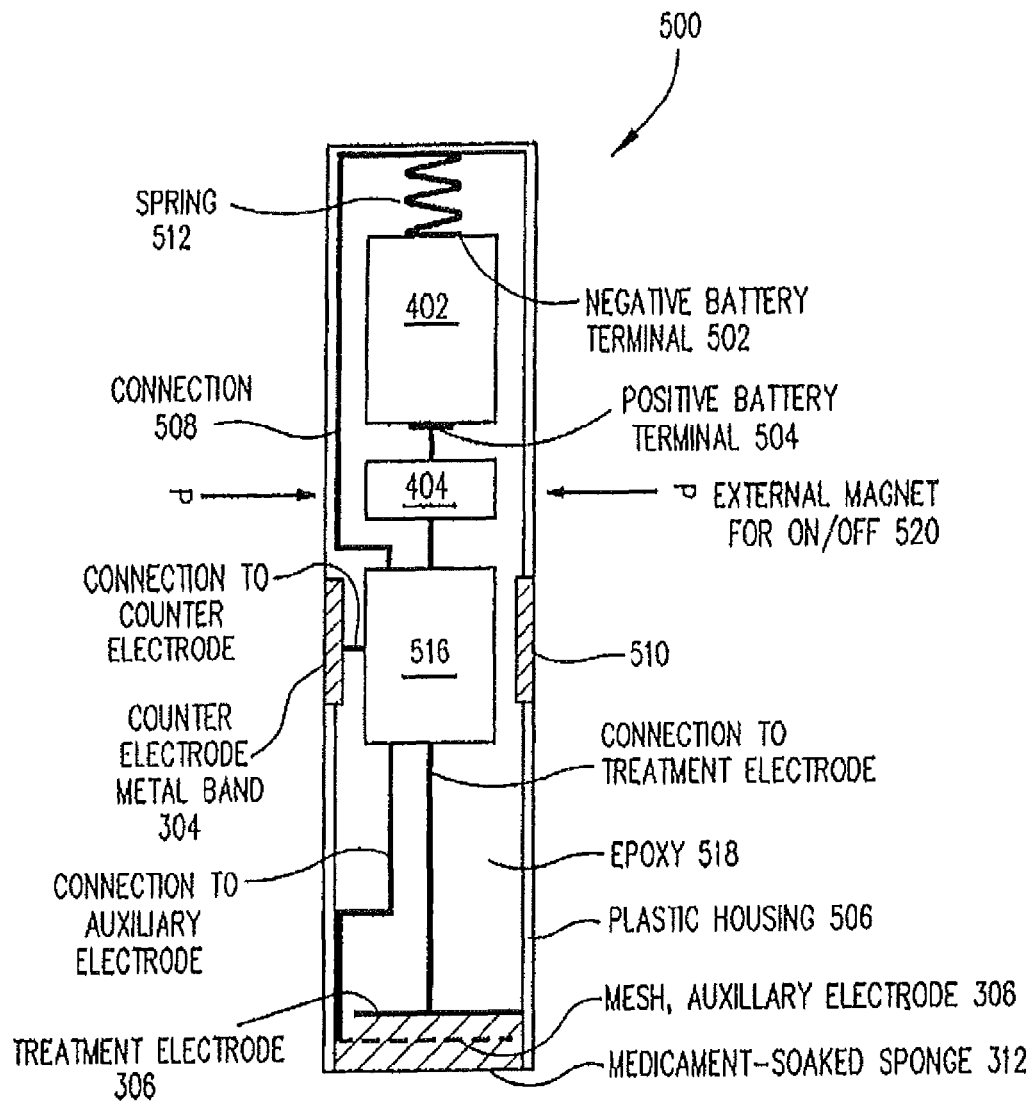
FIG. 35 shows a hand-held device with internal layout of electric and electronic elements.

FIG. 35 illustrates a hand-held device 500 into which the various circuit elements of FIG. 34 may be incorporated. Of course, it will be apparent that the circuit elements of FIG. 34 may be incorporated in a wide variety of devices and the device of FIG. 35 is provided by way of illustration, not limitation. The hand-held device shown in FIG. 35 is configured along the lines of the hand-held devices shown in U.S. Pat. Nos. 5,676,648, 5,879,323 and 5,908,401, the contents of each of which are incorporated herein by reference. For ease of illustration, not all of the elements shown in FIG. 34 are shown in FIG. 35. Housing 506 of the handheld device is preferably formed of plastic and is shaped to comfortably fit within a user's hand. Medicament-soaked sponge 312 is in electrical contact with treatment electrode 306. A mesh or gridded auxiliary electrode 306 is, as an example, interposed between treatment electrode 306 and the patient. Negative battery terminal 502 is connected via an electrical connection 508 to an electronic package 516, and an output of a current drive circuit within electronic package 516 connects to counter electrode 304 provided as a metal band 510 circumferentially (either continuously or discontinuously) formed around housing 506. For the self-administration of medicament, a user touches counter electrode 304 with his/her skin (e.g., fingers). Electrical connection 508 includes a spring portion 512 for holding power source (battery) 402 in place. Positive battery terminal 504 is connected to switch 404 (e.g., a mechanical reed switch or an electronic switch activated by an external magnet denoted at 520). Element 516 in FIG. 35 designates an electronic package at least containing oscillator 410, amplifier 412, current driver 408, redundant safety current limiter 416, current sensor 414 and rectifying elements 320 and 322. Some or all of the components within housing 506 may be contained in epoxy 518.

As described above, in cases in which iontophoresis treatments are administered by a patient without the supervision of medical professionals (e.g., at home), current may accidentally pass through the patient's heart. With conventional equipment, the portion of the current directly traversing the patient's heart could reach a level resulting in ventricular fibrillation. In accordance with the above-described embodiment of the present invention, the frequency of the electrical driving circuit is increased from 0 (DC) to 100 kilohertz. As can be seen with reference to FIG. 32, in this case, the current can be safely increased up to 1 milliampere (RMS). This results in effective delivery of the medicament to the patient. Thus, the use of rectified high-frequency iontophoresis as described above satisfies the established risk-current limit requirements and eliminates the hazard of ventricular fibrillation. In addition, the goal of unidirectional iontophoresis like that of the DC approach can be obtained. Therefore, although the AC current is rectified at the treatment site to obtain DC-like, unidirectional iontophoresis, any current passing through the heart remains strictly bi-directional and alternating with a frequency high enough to meet the risk current requirement.

In rare cases in which AC iontophoresis is applicable, the hazard associated with ventricular fibrillation can also be eliminated by using a high frequency current source around 100 kilohertz. In this special case, rectifying elements and auxiliary electrode 102 are not required because AC iontophoresis is desired. The same circuit design used for unidirectional AC electrophoresis (FIG. 34) is directly applicable.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

C. Electrokinetic Delivery System for Self-Administration of Medicaments and Methods Therefor Referring now to the drawing figures, particularly to FIG. 36, there is illustrated a portable, self-contained, lightweight, compact, finger-mounted, electrokinetic medicament-delivery device or medicator, generally indicated 10 applied to a treatment site on an individual. The device 10 includes a housing 12 mountable to an individual's finger, for example, by straps 14, with a tip 16 of the device 10 mounting an active electrode for driving, i.e., electrokinetically transporting, medicament interposed between the active electrode and the individual's treatment site into the treatment site upon completion of an electrical circuit through the device, the active electrode, the medicament or hydration material carrying the medicament, the individual's body and a counter electrode, i.e., tactile electrode carried by the device. As illustrated, the tip 16 of device 10 housing the active electrode lies adjacent to and underlies the fingerprint portion of the tip of a digit, preferably an index finger, of an individual's hand, enabling the device to be easily manipulated by the individual's arm, hand and finger such that the active electrode at the tip of device 10 may be disposed in overlaying relation to a treatment site with the medicament or medicament-carrying substrate interposed therebetween.

Figure 37:
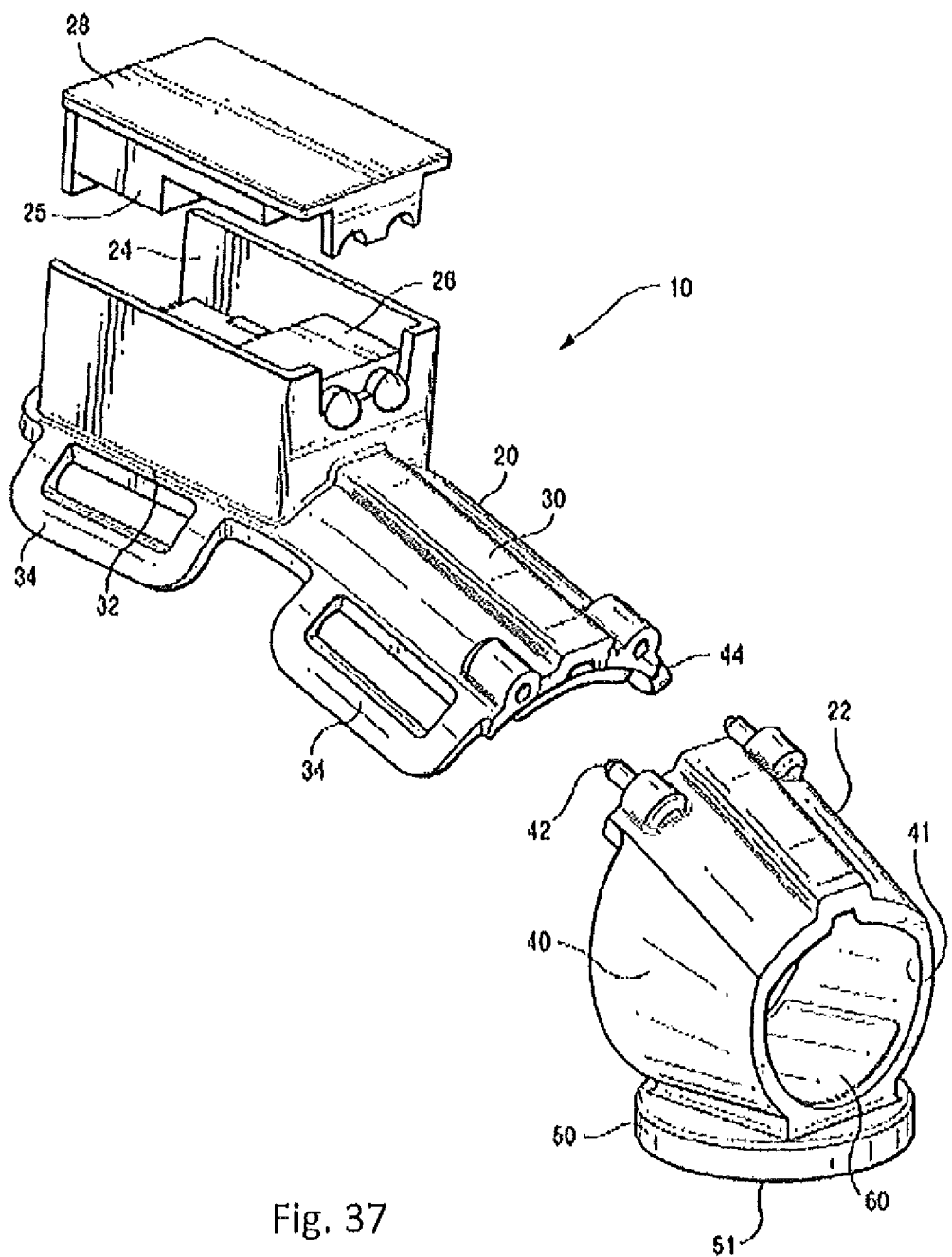
FIG. 37 is an enlarged fragmentary exploded perspective view illustrating the device hereof.

Referring to FIG. 37, the device 10 is preferably provided in two parts: a first part or proximal portion 20 and a second part or distal portion 22. It will be appreciated that the device 10 is substantially rigid in construction, is preferably formed of a plastic material, although other materials may be utilized, and, while a two-part device is preferred, a unitary device or a device formed of more than two parts may be provided. Additionally, while the two parts, when assembled, provide a substantially rigid device, the parts may be interconnected by flexible portions, enabling the device to flex with the flexing of the individual's finger. As explained below, the proximal and distal portions 20 and 22 are connected together to form part of an electrical circuit between an active electrode carried by the distal portion 22, and a power source, tactile electrode and other electronics carried by the proximal portion 20.

The proximal portion 20 includes a compartment 24 for receiving a power source 25, e.g., a 1.5 volt silver oxide battery, as well as an electronics pod 26 for carrying the electronics described below. The compartment 24 may include a removable cover 28 affording access within the compartment. Preferably, however, the compartment is sealed.

Figure 36:
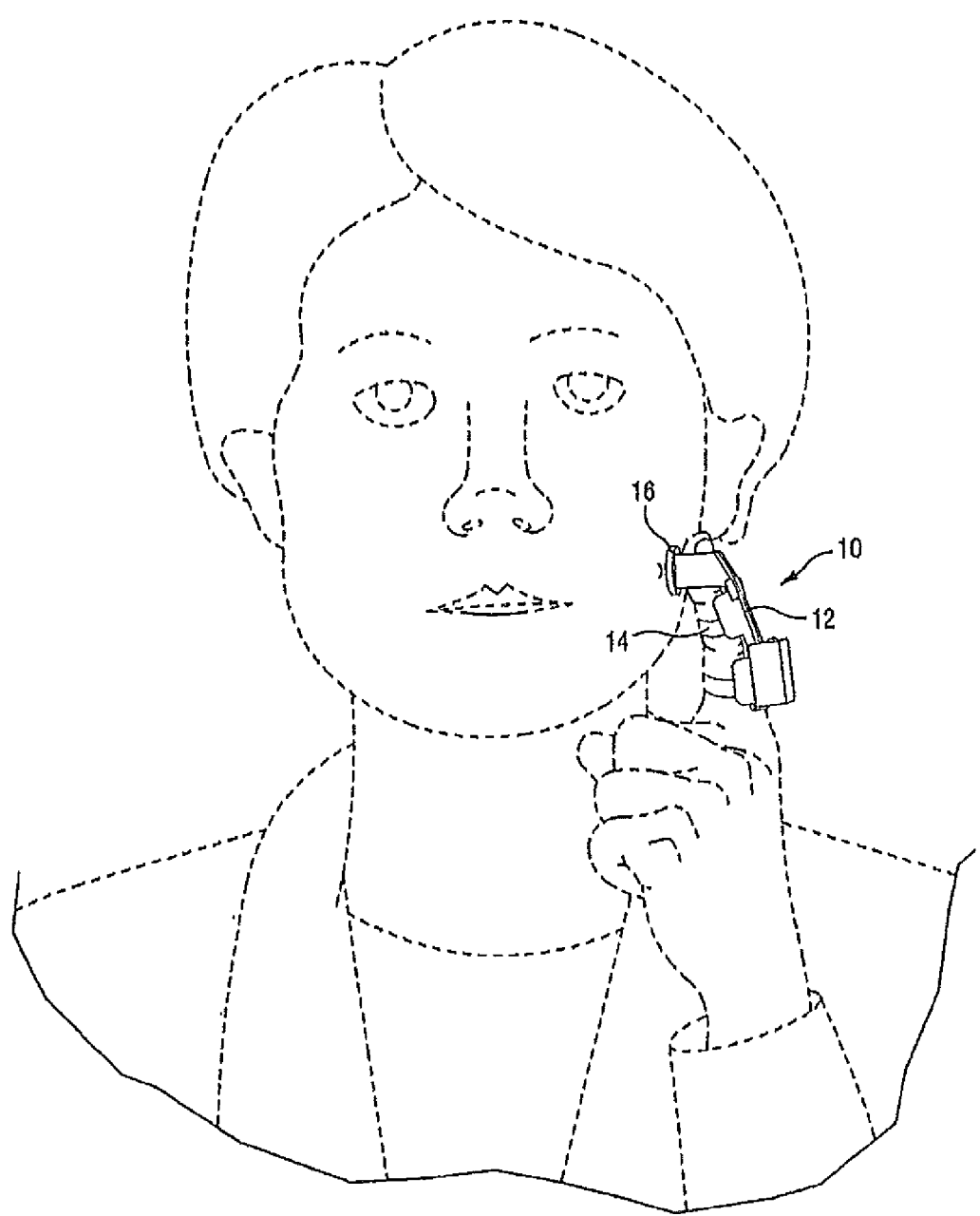
FIG. 36 is a schematic representation of a manner of applying an electrokinetic delivery device according to a preferred embodiment of the present invention to a treatment site.
Figure 38:
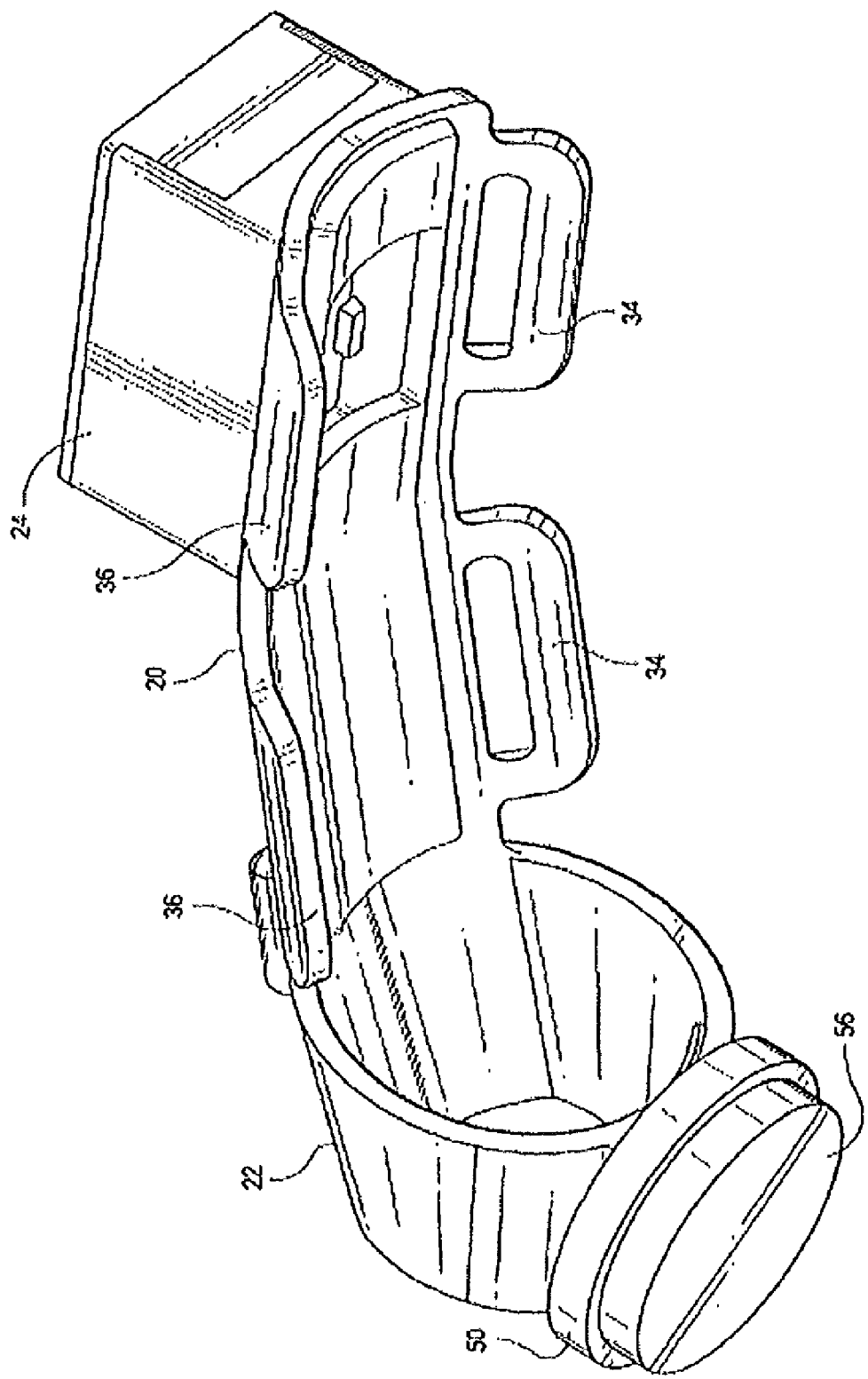
FIG. 38 is a perspective view of a preferred embodiment of the device as viewed from its underside.
Figure 39:
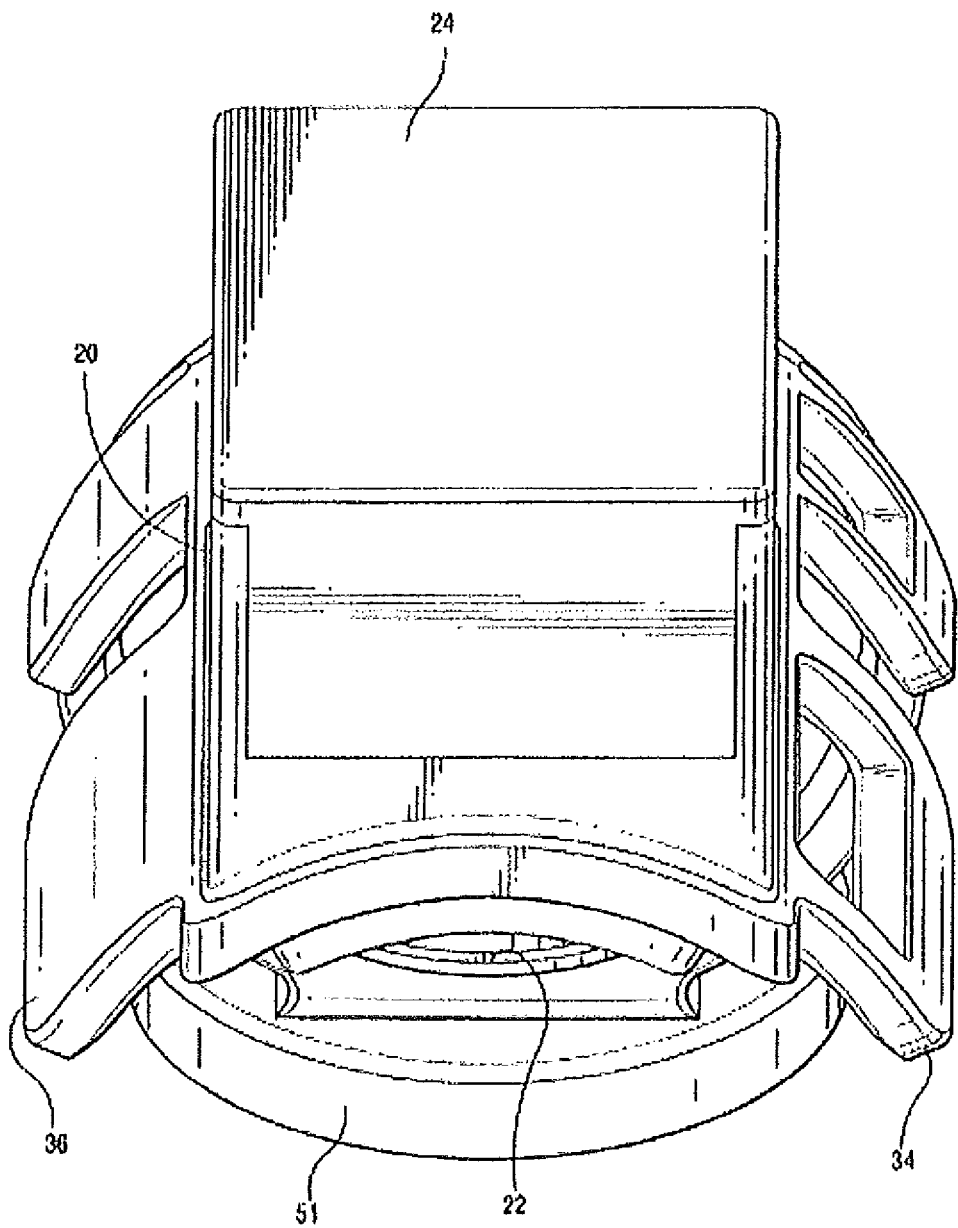
FIG. 39 is an elevational view of the device at a proximal end thereof.
Figure 40:
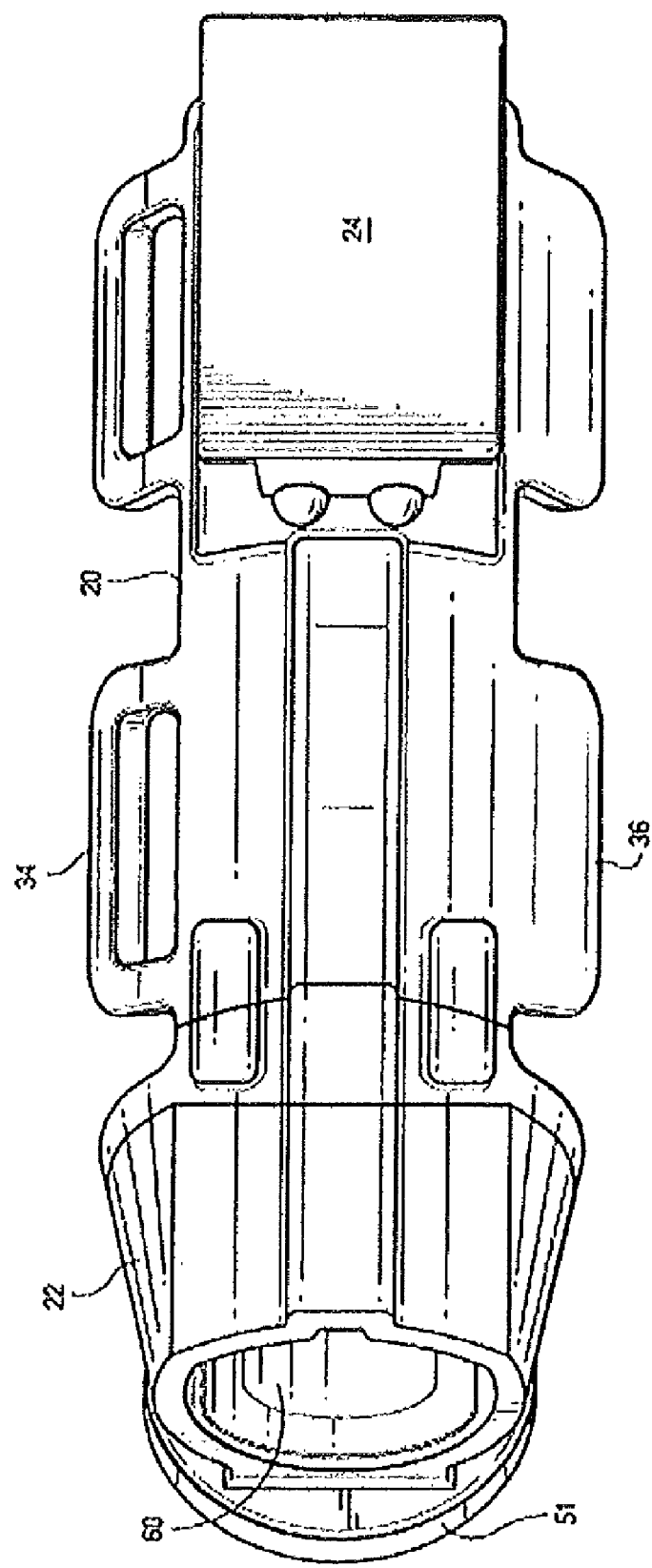
FIG. 40 is a top plan view of the device.

Proximal portion 20 is elongated and shaped and configured to overlie a portion of an individual's finger, preferably an index finger, along opposite sides of the first finger joint, as best illustrated in FIG. 36. That is, forward and rear portions 30 and 32, respectively, of the proximal portion 20 are slightly angled relative to one another to straddle the first finger joint (the joint between the first and second phalanges of a digit) at the apex of the forward and rear portions 30 and 32. Also, the proximal portion 20 has a concave surface along its underside, as best illustrated in FIG. 38, to comfortably overlie and substantially conform to the outer convex portions of the individual's finger on opposite sides of the first finger joint. Adjacent one side and along a margin of proximal portion 20, there are provided a pair of laterally projecting loops 34. Along the opposite margin of proximal portion 20, there are provided a pair of tabs 36. Straps 14 (FIG. 36) are secured in the loops 34. The opposite ends of the straps have one of hook-and-loop fasteners, while the outer surfaces of the tabs 36 carry the other of hook-and-loop fasteners (Velcro®), thereby enabling the device 10 to be releasably secured to an individual's finger. Other means for releasably securing the proximal portion 20 to the individual's finger may be provided. For example, one or more rings or sleeves may be mounted directly to the proximal portion 30 for receiving the individual's finger. Arcuate sections may project from opposite sides of the proximal portion 30 to form one or more resilient split rings for engaging along opposite sides of the individual's finger, their distal ends being spaced from one another along the inside surface of the individual's finger. Elastic straps, buckle-type fasteners, and snap fasteners on elastic or flexible straps may also be utilized. Other types of releasable securements will be apparent to those of skill in this art.

The distal portion 22 of device 10 includes a generally frustoconical section 40 (FIG. 37) sized and configured to receive the tip of an individuals finger, the smaller diameter end of section 40 forming an opening 41 and comprising the outer end of the device. The distal portion 22 may include a closed annular ring as illustrated or a split ring. However, an open-ended frustoconical section having a frustoconical interior surface is preferred because it affords greater control and stability to the active electrode when the medicator is manipulated by the individual to engage the treatment site. Also, the smaller end 41 of the frustoconical section 40 is open to enable the individual's fingertip, including the tip of the individual's nail, to project from the device. It will be appreciated, however, that distal portion 22 may be extended and closed if desired. As illustrated in FIG. 37, a pair of electrical contacts 42 project from the distal portion 22 for engagement in mating electrical sockets 44 formed on the distal end of the proximal portion 20. Thus, when the distal and proximal portions are secured to one another, the power source and electronics of the proximal portion are electrically connected with the active electrode and a counter electrode 60 carried by the distal portion 22. Note also that the juncture of the proximal and distal portions 20 and 22, respectively, lies adjacent the second joint between the second and third phalanges of the digit leaving the third phalange of the digit for reception within the frustoconical interior of the distal portion 22.

Figure 41:
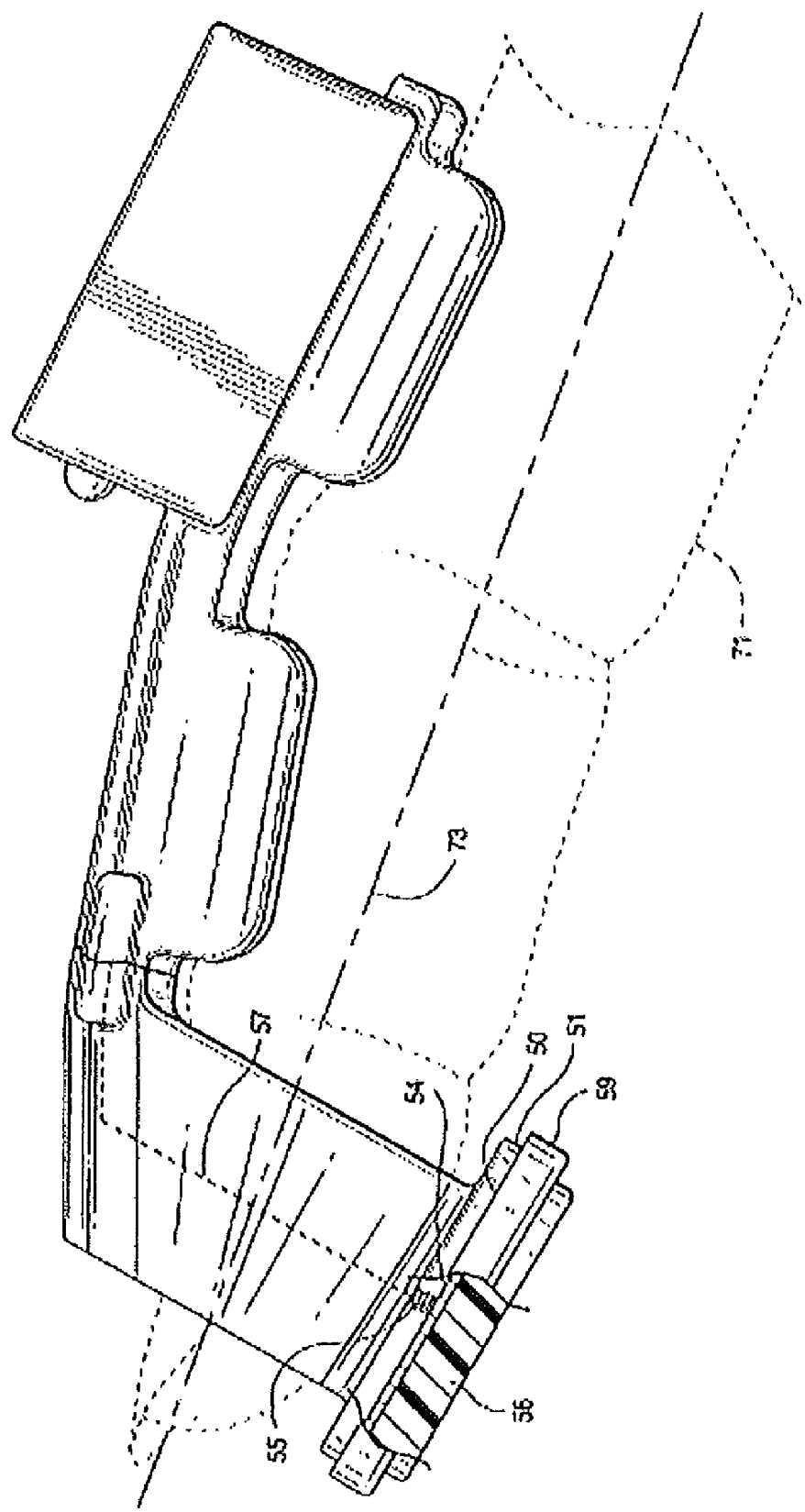
FIG. 41 is a side elevational view thereof.

Referring to FIGS. 38-41, preferably a circular annular housing 50 is provided along the underside of the distal portion 22 and forms part of an applicator head 51 of the distal portion 22. Housing 50 includes an active electrode 54, preferably in the form of a metal disk, mounted at the base of a circular recess 52 (FIG. 41) in housing 50. The active electrode 54 is in electrical contact with the power supply and electronics in the proximal portion 20 when the portions 20 and 22 are connected one with the other. Particularly, a spring 55 in housing 50 interconnects the active electrode 54 and electrical connections 57 within the distal portion 22 in electrical contact with contacts 42 (FIG. 37). As illustrated in FIG. 41, a substrate 56 is disposed in the recess 52, and is preferably formed of a porous, open-cellular, inert material. The substrate material may comprise a non-woven fabric manufactured by Cerex of Pensacola, Fla., identified as Type DN, Group DN07 & DN15. Other suitable types of materials may also be used, provided those materials, at least in the portion of the substrate through which the medicament will be transported to the treatment site, constitute a minimum barrier to the electrokinetic transfer of medicament molecules from the substrate to the treatment site. The substrate 56 preferably conforms to the shape of recess 52, e.g., substantially circular, and may be frictionally maintained within the housing and bearing against active electrode 54. Alternatively, other means may be provided to secure the medicament containing substrate to the housing 50. For example, the recess 52 may include an inwardly directed flange or lip for retaining a substrate within the recess. A preferred embodiment for releasably securing the substrate in the recess 52 in electrical contact with the active electrode 54 is described below with reference to FIG. 42.

Figure 42:
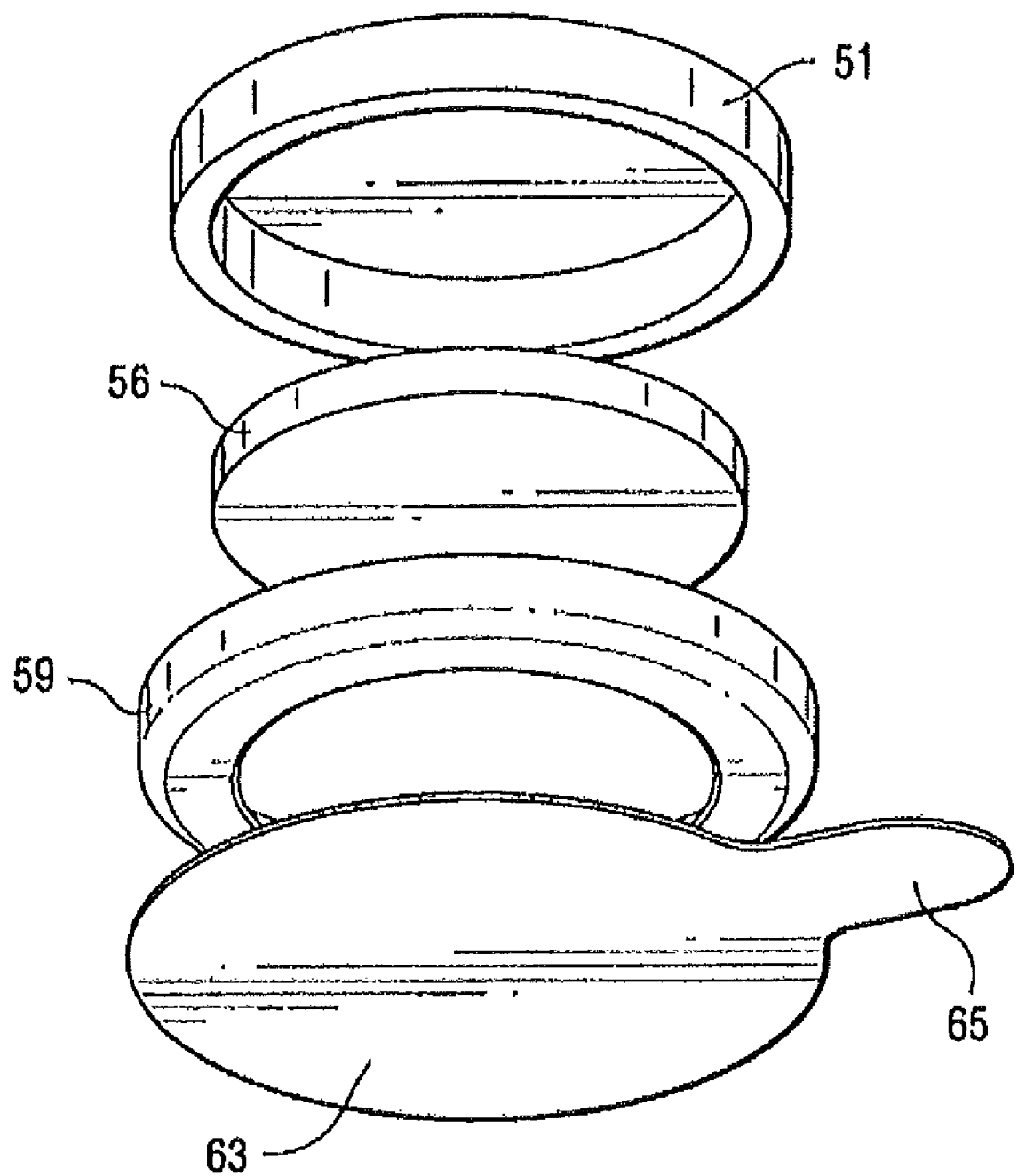
FIG. 42 is an exploded perspective view of a medicated cartridge and the application head to which the cartridge is applied.

It will be appreciated that the substrate 56 may be provided to the user with or without medicament. Thus, when using the finger splint medicator hereof, the user may apply the medicament to the substrate such that the medicament lies within or wicks into the interstices of the material of the substrate. If the applied medicament is not per se conductive, the substrate may also be hydrated by the application of water, for example, by using an eyedropper. In the preferred form, however, a unit dose of the medicament is supplied with and prepackaged in the substrate 56. The medicament permeates the interstices of the porous substrate 56 and the substrate with the medicament is disposed within the recess 52 of the distal portion 22 of the device 10 and factory-sealed. For example, as illustrated in FIG. 42, a retainer ring 59 may overlie the substrate 56 and a release film, e.g., a foil lid 63 having a finger pull or tab 65, may overlie the substrate 56 exposed through the end of the retainer ring 59. By removing the lid 63 prior to use, the medicament permeated in the substrate is exposed for electrokinetic transport into the treatment site.

Alternatively, a unit dose of the medicament may be pre-filled and contained within a rupturable polymer reservoir or capsule within the substrate 56 as in U.S. Pat. No. 5,676,648, issued Oct. 14, 1997, the disclosure of which is incorporated herein by reference. By encapsulating the medicament in a rupturable reservoir or sealing a medicament-permeated substrate, whether within device 10 or separate therefrom, a long shelf-life is assured for medicaments. A non-pre-filled substrate may also be provided the user with the medicament provided separately. In that instance, the user may apply the substrate to the distal portion 22 (if not already contained within housing 50) and either apply the medicament to the substrate before application of the device to the treatment site or interpose the medicament between a suitably hydrated substrate (if auxiliary hydration is required) and the treatment site whereby electrokinetic transport of the medicament into the treatment site can be accomplished. To use the substrate with the encapsulated medicament, the capsule(s) can be opened, for example by peel-away means, such as peeling away a release film, or ruptured by applying pressure to the substrate, for example, by pressing the substrate toward the active electrode 54 after the substrate has been located within the recess 52 of the applicator head either upon manufacture or by the user. By rupturing the capsules, the medicament permeates the interstices of the substrate. If the medicament requires hydration to afford electromotive transport into the treatment site upon application of the electric current, the user may hydrate the pad similarly as previously described. Alternatively, an additional one or more capsules containing hydrating or conductive material, e.g., water or saline, and/or another formulation excipient(s) such as sodium lauryl sulfate with or without cetostearyl alcohol may be prepackaged within the medicament and or substrate.

The substrate 56 is intended for single use only. That is, once the medicament has been electrokinetically driven from the substrate into the treatment site, the distal portion 22 is disconnected from the proximal portion 20 and discarded without the consumer/patient touching the medicament or substrate. It is important to prevent reuse of the distal portion and its used substrate and to render it disposable. For example, active disease particles or other biologic material on the substrate could cause cross-contamination if reused. Insufficient dosage, dehydration or degradation of the medicament could occur if reused. Physical separation of the substrate from the active electrode could occur, rendering dosage or even operability problematical upon reuse. Alternatively, the substrate 56 may be removed from the applicator head 51 and discarded and a new substrate applied to the applicator head. Where the medicament is prepackaged with the substrate either by permeation within the substrate with a release film or foil seal or within a releasable or rupturable capsule within or near the substrate, a coloring agent can be employed, such as iodine, which turns color upon contact with starch in the open-cell material to visibly indicate that a unit dose of medicament has been used, Other types of coloring agents can be used to indicate usage of the applicator, e.g., pH indicators, wet saturation indicators or oxidizable pigments.

Referring to FIG. 41, it will be appreciated that the device 10 is generally elongated and extends generally parallel to the individual's finger 71 when in an extended position as illustrated. The housing 50 extends at an angle relative to the direction of elongation represented by a centerline 73 in FIG. 41 of the device which generally parallels central portions of the individual's finger when extended, Thus, the outer planar face of the active electrode 54 extends at the same angle as the housing relative to the elongated device and faces outwardly and away from the device and the individual's finger. The angle at an intersection between the direction of elongation (centerline 73) and a line through the planar surface of the active electrode 54 is an obtuse angle of approximately 160.degree. but may lie within a range of about 100.degree.-185.degree. The angular direction of the active electrode relative to the device 10 facilitates application of the device to treatment sites variously located about an individual's body.

Reverting to FIG. 37 and in a preferred embodiment, the counter electrode 60 is located in the distal portion 22 on the bottom of the interior frustoconical surface. Counter electrode 60 may be covered with a conductive material, e.g., water or hydrogel, to facilitate electrical contact with the underside of the individual's fingertip. The counter electrode 60 is electrically insulated from the active electrode. The counter electrode 60 is electrically coupled to the terminal of the battery opposite the battery terminal to which the active electrode 54 is coupled when the distal and proximal portions are electrically interconnected with one another. It will be appreciated that by locating the counter electrode 60 along the inside surface of the distal portion, the act of inserting the individual's fingertip into the opening in the distal portion ensures good electrical contact between the counter electrode and the individuals finger. Alternatively, the counter electrode may be exposed along the underside of the proximal portion 20 for engagement with the individual's finger upon the individual donning the finger splint medicator. In a further alternative, the counter electrode may be located along the underside of both the proximal and distal portions 20 and 22, respectively, Thus, a full-length portion of the individual's finger on opposite sides of the first finger joint and including the fingertip may be in contact with the counter electrode, in either case, affording a good electro conductive contact therewith.

Figure 43:
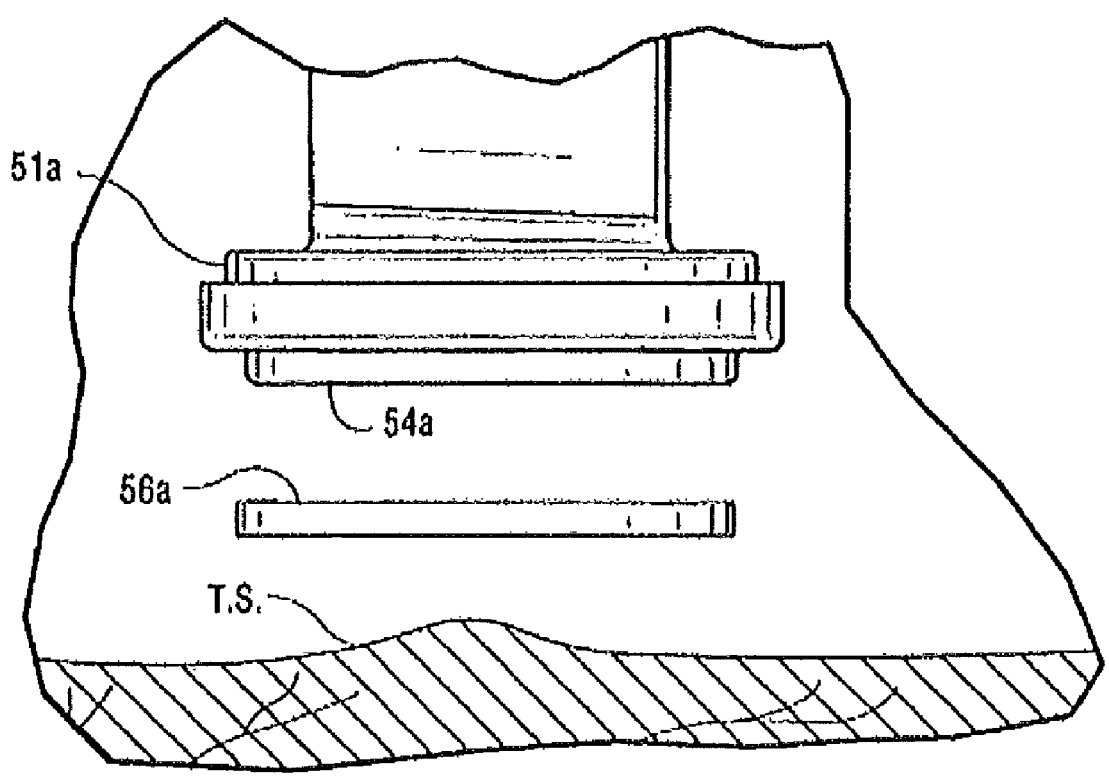
FIG. 43 is a side elevational view of a portion of an applicator head and substrate in accordance with another embodiment hereof.

Referring to FIG. 43, there is illustrated a portion of an applicator head 51a in conjunction with a substrate 56a separate and apart from the device per se. The applicator head 51a is similar to the applicator head 51, except that the active electrode 54a forms a circular projection from the applicator head 51a. Also illustrated in FIG. 43 is a substrate 56a which has been removed from a package, not shown, and which substrate contains the medicament. With the substrate 56a containing the medicament interposed between the active electrode 54a and the treatment site T.S., it will be appreciated that upon completing the electrical circuit by coupling the distal and proximal portions to one another, the medicament in the substrate may be electrokinetically motivated into the treatment site. As a further alternative, the medicament can be applied by a user directly to the treatment site or to a non-prefilled substrate, together with any necessary hydration material, and the circuit completed by applying the active electrode 54a to the medicament or medicament-containing substrate.

The first three stages of Herpes I and II are prodromal, erythema and papule/edema. The preferred treatment with Acyclovir® is to identify and treat the infection in its prodromal stage (no visible signs or symptoms, but individuals feel a tingle or burning or some sensation in the area that breaks out later), i.e., treat optimally with least amount of medicament and shortest application time. Erythema is second (still quite early, with some redness and/or swelling) and is the preferred stage to start treatment if prodromal stage is missed. Papule or edema stage still responds to treatment but not as quickly (skin damage has started to occur with small sores which may be barely visible).

In a preferred form of the present invention, particularly for the treatment of Herpes I and II-type infections, Acyclovir® is the medicament of choice. Acyclovir® may be provided in a cream formulation with approximately 5% comprising the drug Acyclovir®. For example, a 250 milligram formulation of topical cream containing 12.5 milligrams of Acyclovir®, i.e., a 5% formulation, may be utilized. Significantly, this relatively small amount of medicament in the formulation, when applied electrokinetically over a predetermined time duration, affords a therapeutically effective dose. The dosage and time of application may be varied. For example, an approximate 2% formulation of about 4 to 5 milligrams of the active medicament (e.g., Acyclovir®) in a 250 milligram cream formulation applied electrokinetically over a period of no greater than fifteen minutes or an approximate 14-15% formulation, e.g., 37 milligrams in a 250 milligram cream and Acyclovir® formulation, applied electrokinetically for approximately three minutes is believed therapeutically effective. Percentage formulations between 2%-15% over time durations between fifteen minutes and three minutes are believed also to be therapeutically effective. For example, 8%-10% formulations over 5-6 minutes' time duration are also believed therapeutically effective. Thus, using the present device and a small amount of the active medicament applied electrokinetically and locally via the present delivery system has been found effective. While a cream formulation is preferred, it will be appreciated that the topical base may also be a liquid, gel, ointment or lotion.

The formulation for the medicament may also comprise an oil, water, or a combination oil and water, to facilitate penetration of the skin as the excipient(s). For example, oil facilitates penetration of the stratum corneum layer of the skin, while water facilitates penetration of the basal epidermal layer. Thus, a combination of the drug with oil and water included in the formulation is preferred to facilitate penetration of the drug to the treatment site. In a further formulation of Acyclovir®, solvents such as methylene chloride or beta-cyclodextrin may be included to improve water solubility and stability.

The foregoing treatment is also effective for treating Herpes Zoster, Cytomegalovirus (CMV) and additional medicaments of choice may include foscarnet and gancilovir. The device and methods hereof may also be used to provide electrokinetic transport, with or without ultrasound, for tamoxifen citrate, i.e., an antiestrogen, to inhibit Trans Growth Factor .beta.-1 (TGF.beta.-1) to suppress estrogen receptors to aid in wound healing and treatment of keloid scar tissue.

Also, treatment of eczema with tacrolimus or pimecrolimus as a stand-alone therapy or with steroids is effective. Still further, while Acyclovir® acts on the polymerase enzyme, drug formulations which act on the helicase-primase enzyme are also effective for treating Herpes I and II.

Figure 44:
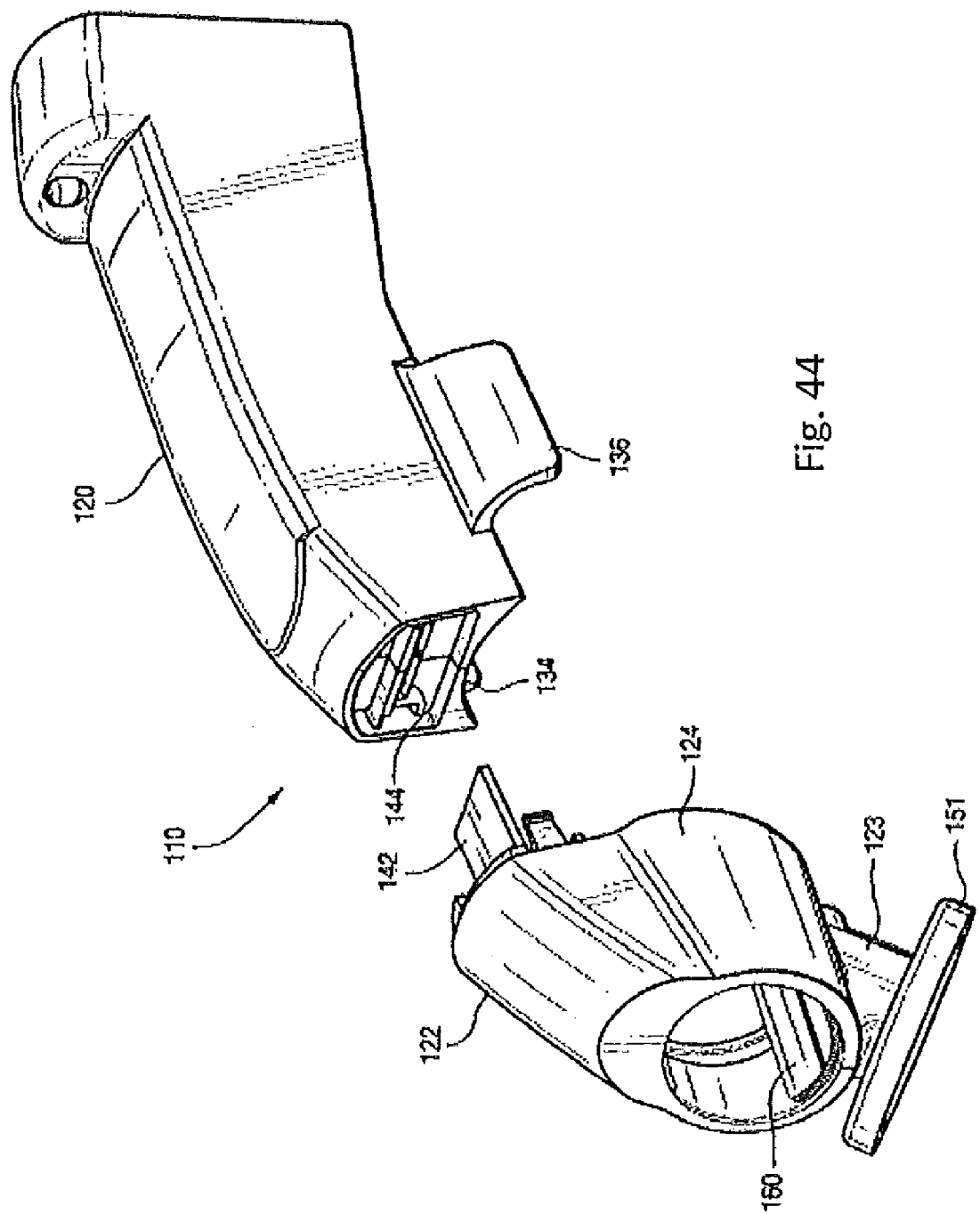
FIGS. 44 and 45 are disassembled and assembled perspective views of an electrokinetic delivery device according to another embodiment hereof.
Figure 45:
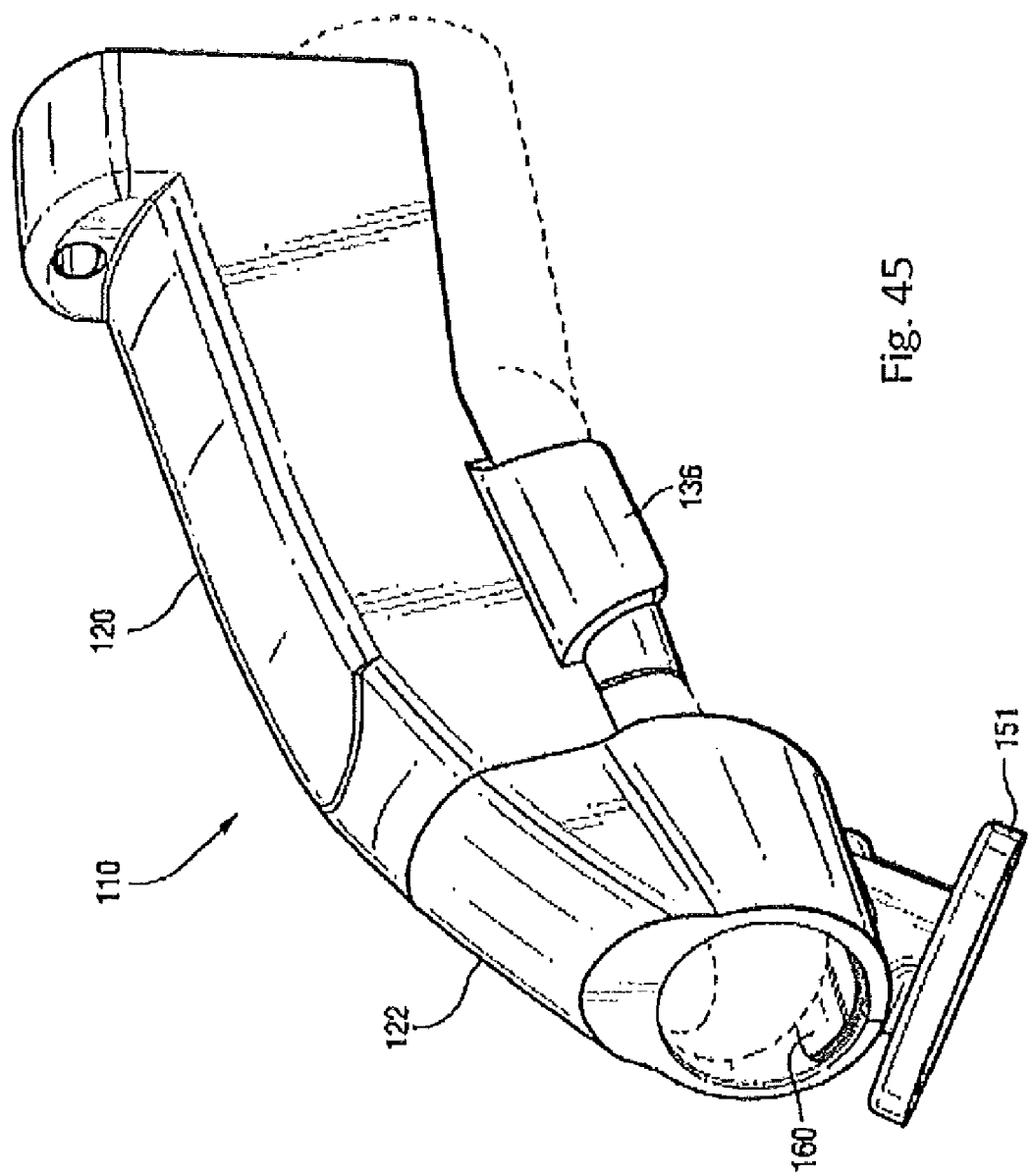

Referring now to FIGS. 44 and 45, there is illustrated a further form of an electrokinetic delivery device according to a preferred embodiment of the present invention wherein like reference numerals are applied to like parts, preceded by the numeral 1. In this form, the device 110 includes proximal and distal portions 120 and 122, respectively, and contacts 142 and 144 in the distal and proximal portions, respectively, for completing the electrical circuit as described herein. The proximal portion 120 includes loops 134 and tabs 136 on opposite sides for securing a strap to the proximal portion and securement of the device to the individual's finger. The proximal portion 120 houses the electronics and power source similarly as the proximal portion 20.

The distal portion 122 is generally frustoconically shaped, as is the distal portion 22 of the prior embodiment, and mounts a pylon or a pair of pylons 123 interconnecting the frustoconical section 124 and the applicator head 151 housing the substrate. The distal portion 122 also carries the counter electrode 160 which, upon interconnection of the proximal and distal portions is electrically connected to the power source and electronics of the proximal portion 120. It will be appreciated that the undersurface of the proximal portion 120 is concave and angled to accommodate the first finger joint and opposite sides thereof for mounting the proximal portion on the individual's finger. Similarly, the distal portion 122 has a frustoconical interior surface for receiving the fingertip of the individual upon electrical and mechanical connection of the proximal and distal portions to one another. In FIG. 45, the device is illustrated in an operable condition applied to an individual's finger, with the individual's fingertip projecting into the distal portion and in electrical contact with the counter electrode 160.

Figure 46:
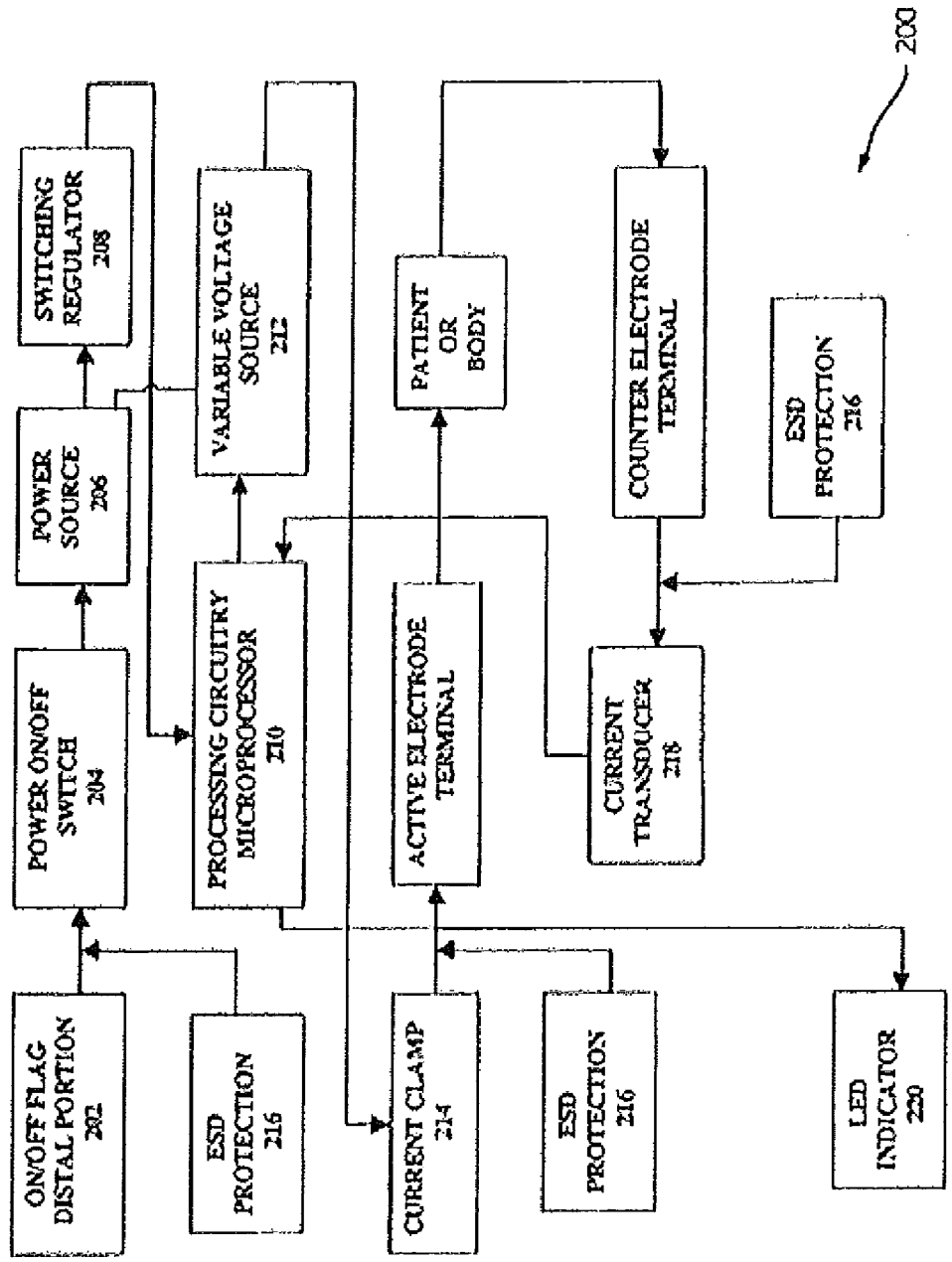
FIG. 46 is a block diagram of an example electrical circuit for the device hereof.

FIG. 46 illustrates a block diagram of representative electrical circuitry 200 for use in the finger splint medicator. Electrical circuitry 200 includes an on/off flag 202, a power on/off switch 204, a power source 206, a switching regulator 208, processing circuitry (microprocessor) 210, a variable voltage source 212, a current clamp 214, electrostatic discharge (ESD) protection circuits 216, a current transducer 218, and light emitting diode or diodes (LED's) 220. The on/off flag 202 is built into the distal portion and may simply include a conducting "flag" surface which completes a circuit of the power on/off switch 204 upon engaging to the proximal portion of the finger splint medicator. The flag surface may, for example, be a thin (e.g., 0.032" thick), copper-clad G10 board with copper on one side thereof. The power on/off switch may simply include two contacts connecting to the power source 206 and to the remaining parts of electrical circuitry 200.

Power source 206 is a battery such as a silver oxide battery having an open-circuit voltage, for example, of 1.55V. The useful life of the battery terminal voltage ranging from 1 to 1.55 V is insufficient to operate circuit elements and components such as processing circuitry 210 and LED's 220. The low battery voltage is tolerated due to the compensation by switching regulator 208, which converts the unsteady and decaying battery voltage to a constant value of, for example, 2.7V.

Skin and tissue resistance largely controls the bias potential required to sustain the treatment current. Other factors include the conductivity of medicament and the resistance between the skin and counter electrode interfaces. A typical range of overall resistance to be encountered is from 5 kohm to 80 kohm. In the most extreme case, a potential of over 30V may be necessary. Variable voltage source 212 converts the low battery voltage to a suitable high output value controlled by a signal from processing circuitry 210. Measurements of the treatment current from current transducer 218 are compared with a desired treatment current for the particular application to obtain an error signal. Processing circuitry 210 increases or decreases the control signal to the variable voltage source 212 with an appropriate digital output signal to reduce and eliminate the measured error signal so as to obtain the minimal necessary instantaneous bias potential for maintenance of the desired treatment current. Current clamp 214 is a redundant safety device used to limit the treatment current to a safe, maximum value (e.g., 450 microamps) under any circumstances.

Electro Static Discharge (ESD) protection circuits 216 (such as one or more diodes) are installed at the entry points of the flag terminal and the positive and negative treatment electrodes, respectively, to protect the internal circuitry from electrostatic damage. The ESD protection circuit for the flag terminal is disposed on the proximal side.

Current transducer 218 converts the instantaneous treatment current to an analog voltage. This voltage is read by the processing circuitry 210 through an internal analog-to-digital (A/D) converter. This digital signal is compared with the selected treatment current value scalable to the reference input voltage of the A/D converter. A digital servo loop is maintained by the processing circuitry 210 to minimize and/or eliminate the error signal between the instantaneous treatment current signal and the current reference. The output of the servo loop is a digital signal converted by an R/C (Resistor/Capacitor) circuit to an analog voltage, which is then used to control the variable voltage source 212.

Processing circuitry 210 performs various tasks including, but not limited to, timing control, current measurement, digital servo of treatment current through feedback control of the bias potential, and illumination of LED or LED's, Processing circuitry 210 may be implemented, for example, as a microprocessor, microcontroller, an application specific integrated circuit (ASIC), a programmable logic array or some combination thereof.

Processing circuitry 210 includes read-only and/or read/write memory. In one example implementation, processing circuitry 210 includes a read/write memory such as an EEPROM. The operations of processing circuitry 210 may be implemented in hardware, software and/or firmware. It is desirable, although not necessary, to reduce and replace hardware elements to the extent possible by using a firmware implementation. Data and instructions for controlling the overall operation of the finger-splint device may be written respectively, to an EEPROM data memory and a flash program memory, and processing circuitry 210 may execute the instructions in response to various signals supplied thereto, These instructions may include instructions for:

monitoring the treatment current and the battery terminal voltage, providing timing control for various treatment phases including the initial standby period (for example, indicated by a flashing green LED), soft-start period, main treatment period (indicated by a constant green LED) and the final soft stop period (indicated by the red LED). The treatment phases need not be the same for all treatments and these phases may vary in some way depending on what is being treated. All the variables, voltage, current, time, electrode size and shape, and the like must be reconsidered and possibly adjusted, illuminating the LED(s) to provide information to the user,
exciting a crystal oscillator for accurate timing reference,
resetting a watchdog timer to ensure normal software execution,
performing a self-consistency check on the accuracy of analog-to-digital converter by measuring the predictable voltage drop across a circuit element (such as an LED) during a short, initial power-up period, and
performing servo control of the treatment current by controlling the bias potential generated by the variable voltage source via an output digital signal.

The data stored by the read/write memory within the proximal portion may also include a count indicative of the number of treatment cycles for which the finger-splint device has been used. This count is incremented (or decremented) for each treatment and the device is permanently deactivated after the count reaches a prescribed number indicative of a predetermined number of treatments. For example, a disable flag for disabling processing circuitry 210 may be set in memory when the count on the counter is indicative of the prescribed number of treatments. Alternatively or additionally, various mechanisms for preventing the supply of power to the electrical components may be used to permanently deactivate the device. For example, processing circuitry 210 could generate a signal to burn a fuse when the count on the counter is indicative of the prescribed number of treatments. Similarly, processing circuitry 210 could generate a signal to deliberately damage a transistor or flip a solid state toggle circuit when the count on the counter is indicative of the prescribed number of treatments. It will be readily apparent that other mechanisms (hardware and/or software) may be used and the invention is not limited in this respect.

In another example implementation, the read/write memory may store a total treatment time, which is incremented (or decremented) in accordance with a timer during treatment. When the total treatment time reaches some prescribed total treatment time, the device may be permanently deactivated. Here again, for example, the various hardware and/or software disabling mechanisms described above may be used to permanently deactivate the device.

In still another example implementation, the proximal portion may be disabled from use for a predetermined time period after each use whereby the next use can only occur after the predetermined time period has expired. In this case, a disable flag could be set for the predetermined time period and processing circuitry 210 could prevent operation of the proximal portion when this flag is set.

Also, the distal portion may be deactivated permanently after a single usage. Here again, various mechanisms for prevention of re-use of the distal portion may be used. For example, processing circuitry 210 could generate a signal to burn a fuse incorporated in the distal portion at the end of a treatment. Similarly, processing circuitry 210 could generate a signal to deliberately damage a transistor or flip a solid state toggle circuit incorporated in the distal portion at the end of a treatment. It will be readily apparent that other mechanisms (hardware and/or software) may be used and the invention is not limited in this respect.

Processing circuitry 210 may be programmed with (or have accessible thereto) instructions for a plurality of different types of treatments (e.g., herpes, eczema, acne, boils, blemishes and the like). For example, the desired treatment current, ramp-up/ramp down characteristics and total treatment time for herpes may be different than the desired treatment current, ramp-up/ramp-down characteristics and total treatment time for eczema. The determination of which instructions to use may be based upon a detection (or "recognition") of a particular type of distal portion attached thereto. For example, a distal portion for the treatment of herpes may be configured (either physically or electrically) differently than the distal portion for the treatment of eczema. The configuration of the distal portion is detectable by processing circuitry 210 so that processing circuitry 210 thereafter executes instructions appropriate for the particular type of distal portion connected thereto.

In another implementation, the distal portion may be provided with an interface for interfacing to a computer. Such an interface may, for example, be a serial port, a parallel port, a USB port, an IEEE 1394 port, etc. The interface may take the form of a cradle or docking station into which the distal portion is placed, the cradle or docking station connecting to the computer. The interface to a computer allows the uploading and downloading of data from/to the distal portion. For example, a physician, pharmacist or other health care provider could download to the distal portion instructions appropriate for a particular treatment. Alternatively, an appropriate one of a plurality of different, pre-programmed instruction sets may be selected. Processing circuitry 210 may be programmed to record in memory treatment information (such as the time a treatment took place, the duration of the treatment, the distal portion type connected thereto, etc.). This recorded information may be uploaded to a database containing treatment records for the user via the computer interface.

Assuming appropriate power is available, the distal and/or proximal portion may be provided with additional elements. For example, a small liquid crystal display (LCD) could be provided to the distal or proximal portion to provide a visual output of timing and/or diagnostics. Sound generating circuitry such as a buzzer may also be added to provide aural indications such as warnings, end-of-treatment, etc.

Figure 47:
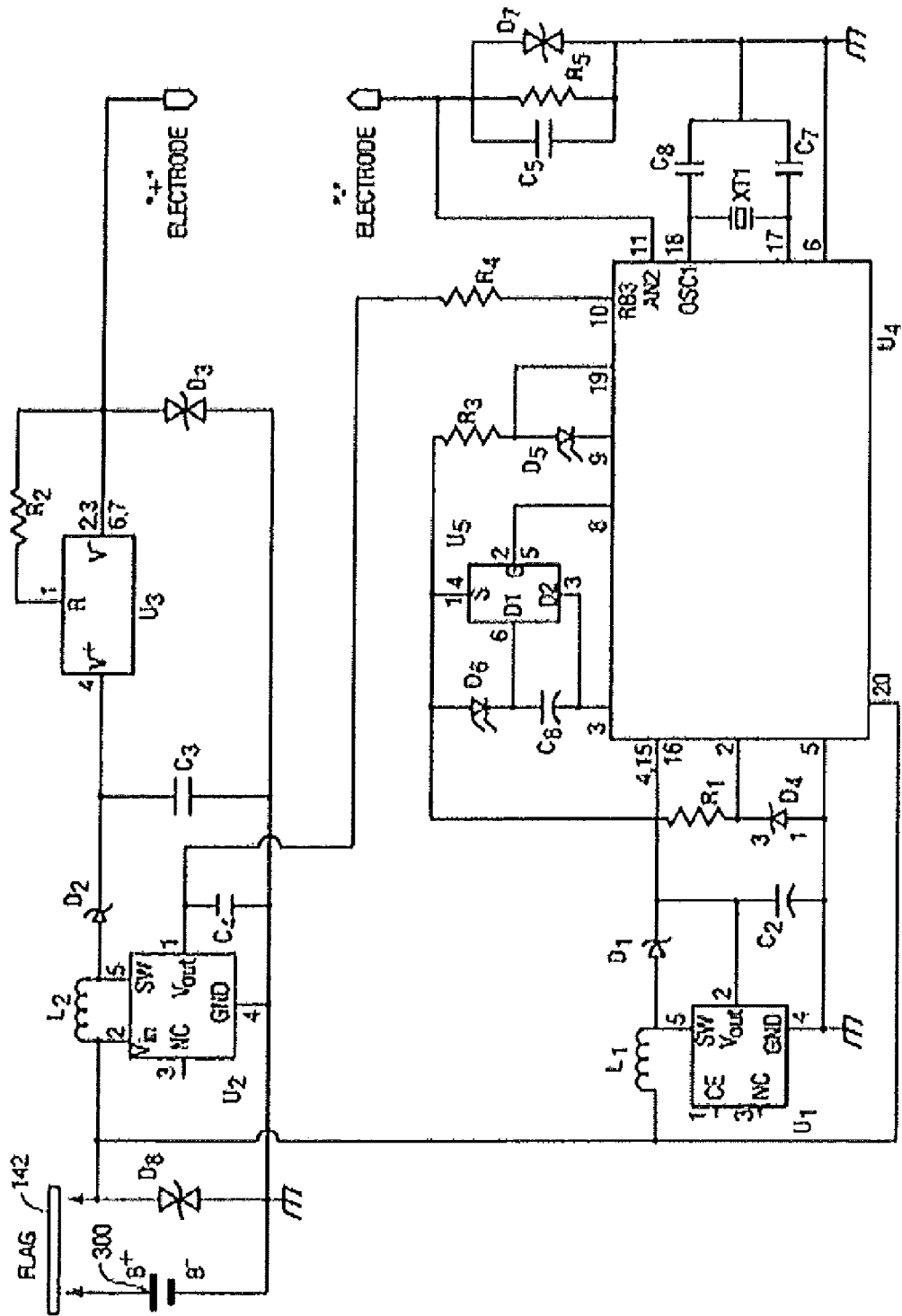
FIG. 47 is a schematic of an example electrical circuit for the device hereof.

FIG. 47 is a schematic showing details of example electrical circuitry 200. Battery 300 corresponds to power source 206 (FIG. 46) and may, for example, have an open-circuit voltage of 1.55V and a rated capacity of 200 mAhr. A suitable battery may be, but is not limited to, EPX76 1.5V silver oxide battery (designation: IEC SR44) available from Eveready Battery Co., Inc. Such a battery would provide for about 10 treatment sessions, if each were ten minutes in length.

Components U1, L1, D1, C1 and C2 correspond to switching regulator 208 (FIG. 46) for converting the battery voltage to a constant value of, for example, 2.7 V. U1 may be, but is not limited to, an NCP1402SN27T1 step-up DC-DC converter (TSOP-5) available from On Semiconductor, Inc. L1 may be, but is not limited to, ELJ-EA470KF, 47 microhenry inductor (SMT-1210) available from Panasonic Industrial Co. D1 may be, but is not limited to, an RB751V40T1 Schottky barrier diode (SOD-323) available from On Semiconductor Inc. C1 and C2 may be, but are not limited to, a 22 microfarad, 4V tantalum capacitor (A case) and a 47 microfarad, 4V tantalum capacitor (B case), respectively.

Component U4 corresponds to processing circuitry 210 and may be, but is not limited to, a PIC16F85 microcontroller (SSOP-20) available from Microchip Technology Inc.

Components U2, L2, D2 and C3 function as variable voltage source 212 (FIG. 46) for converting the low battery voltage to a high output value. U2 may be, but is not limited to, an S-8324D20MC switching regulator (SOT-23-5) available from Seiko Instruments USA. L2 may be, but is not limited to, an ELJ-EA101KF, 100 microhenry inductor available from Panasonic Industrial Co. D2 may be, but is not limited to, an MBRO540T1 Schottky barrier diode (SOD-123) available from On Semiconductor Inc. C3 may be, but is not limited to, a 1 microfarad ceramic capacitor (50V, Y5V, SMT-1206). Variable voltage source 212 is controlled in accordance with a signal from processing circuitry 210. Based on measurements of the treatment current, processing circuitry 210 calculates an appropriate digital output signal to obtain an instantaneous bias potential. Component R4 coupled with C4 functions as a simple digital-to-analog converter. R4 may be, but is not limited to, a 10K ohm, 1% metal film resistor (SMT-0603). C4 may be, but is not limited to, a 0.1 microfarad ceramic capacitor (10V, X7R, SMT-0402).

Components U3 and R2 correspond to current clamp 214 (FIG. 46) and limit the treatment current to a maximum, safe value such as, for example, 450 microamps. U3 may be, but is not limited to, an LM334M current source (SO-8) available from National Semiconductor Corp. R2 may be, but is not limited to, a 150 ohm, 1% metal film resistor (SMT-0603).

D3, D7 and D8 correspond to (ESD) protection circuits 216 (FIG. 46) and D3 comprises 36 V bi-directional voltage suppressor (TVS), which is installed at the positive electrode. This TVS protects internal circuitry from electrostatic damage. D3 may be, but is not limited to, an SMAJ36CA transient voltage suppressor (SMA) available from Diodes Inc. D7 and D8 may be, but are not limited to, a PSD03C 3.3V transient voltage suppressors (SOD-323) available from ProTek Devices.

R5 corresponds to current transducer 218 (FIG. 46) and converts the treatment current to an analog voltage, which is further stabilized by C5. R5 may be, but is not limited to, a 4.99 Kohm, 1% metal film resistor (SMT-0603). C5 may be, but is not limited to, a 0.47 microfarad ceramic capacitor (50V, Z5U, SMT-0805).

Green LED D6 and red LED D5 correspond to LEDs 220. Suitable LED's include, but are not limited to, a green diffused LED and a red diffused LED available from American Bright Optoelectronics Corp. (BL-B22131 and BL-B4531). Green LED D6 remains on during the entire treatment period. The LED normally requires a current limiting resistor for its operation and the resulting power consumption is quite substantial. As shown in FIG. 47, a capacitor C8 switched in accordance with U5 operates as an efficient current limiting device. The situation with red LED D5 is different in that on the rare occasions when it is illuminated, the treatment current is switched off and resistor R3 and the resulting power consumption can be tolerated. U5 may be, but is not limited to, an Si1905DL dual P-channel MOSFET (SC-70-6) available from Vishay Intertechnology Inc.

The electronic circuitry described in connection with FIGS. 46 and 47 is operable so that the finger-splint electrokinetic medicator provides a controlled current for electrokinetically transporting medicament into the treatment site and into the underlying tissue area. The disclosed electronic circuitry provides an effective therapeutic for a skin lesion by incorporating the following features:

the treatment current is increased and decreased gradually to avoid any uncomfortable sensation of electrical shock, the rise and fall of current may follow a linear ramp or an exponential curve with a long time constant, (e.g., 10 seconds), the treatment current per application is accurately controlled by automatic feedback, e.g., maintained at 0.4 milliamperes or less, an upper limit of the treatment current is imposed by a stand-by redundant circuit element in order to safeguard against servo loop malfunction, minimal bias potential, dictated largely by patient skin resistance, is always applied in order to minimize power consumption, ESD protection is implemented for electronic circuitry, indicator light(s) are provided for low battery conditions, diagnostics, hardware malfunction, low treatment current, and test completion, therapeutic phase, the prescribed treatment time period and automatic test termination are accurately controlled, and treatment history is monitored and the device is permanently deactivated after reaching a prescribed length of time and/or number of treatments or uses.

The circuit described in connection with FIGS. 46 and 47 provide these identified features. However, the present invention is not intended to be limited to only circuits that provide for all these features. In addition, it will be appreciated that the specific components and the arrangements thereof shown in FIGS. 46 and 47 are provided by way of example, not limitation. For example, power source 300 may be an adapter for converting power from a conventional wall outlet to power suitable for operation of the finger splint. Alternatively, power source 300 may be a battery that is rechargeable via an adapter connected to a conventional wall outlet. In addition, the electronic circuitry may be adapted to include an alternating current source as described in application Ser. No. 09/523,217, filed on Mar. 10, 2000, the contents of which are incorporated herein by reference, including the hybrid multi-channel design. In still other alternative implementations, the power source may be provided in the distal portion or the distal portion may be provided with a power source to supplement the power source in the proximal portion.

Figure 54A:
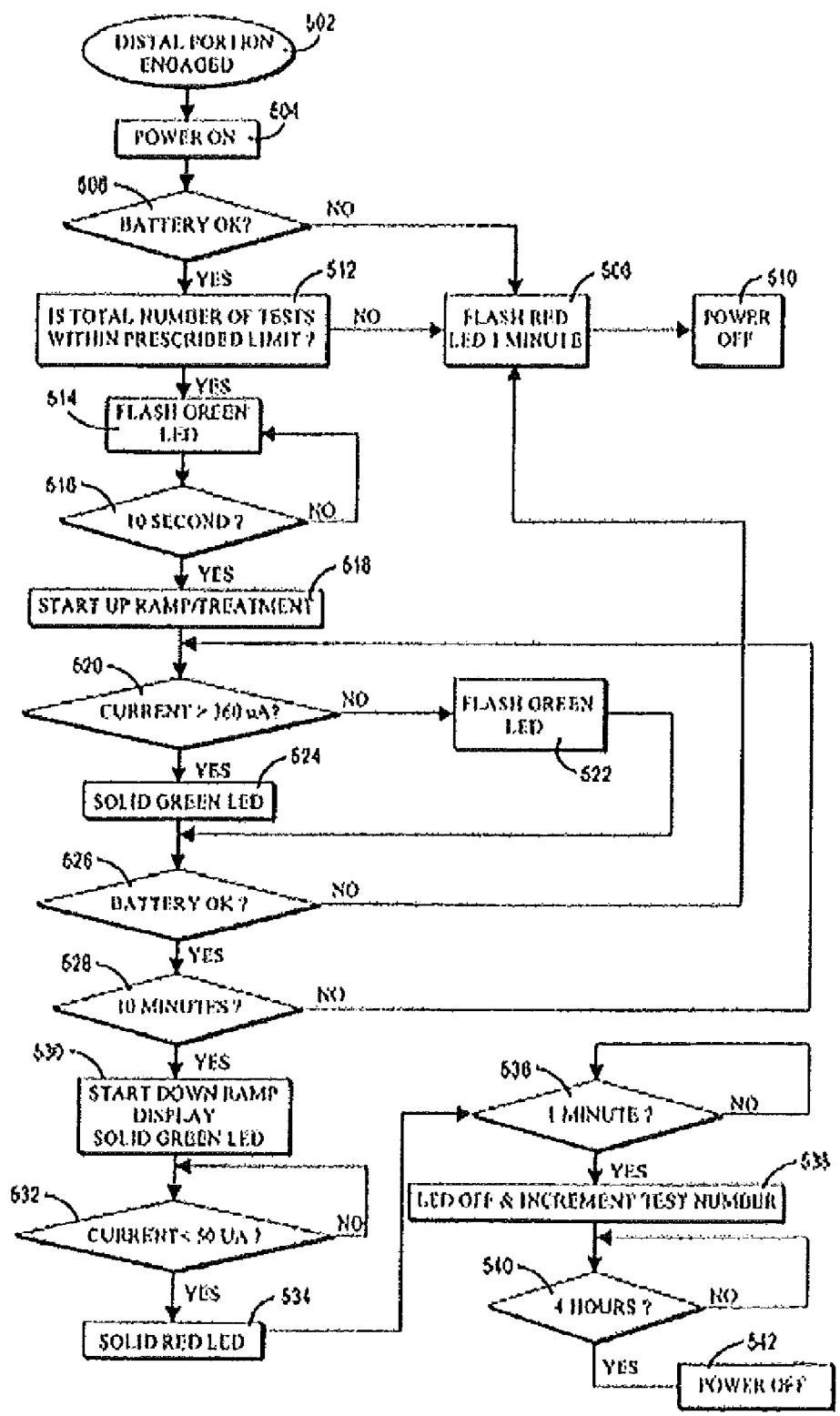
FIGS. 54A and 54B are flow charts illustrating an example operation of the device of FIG. 37.
Figure 54B:
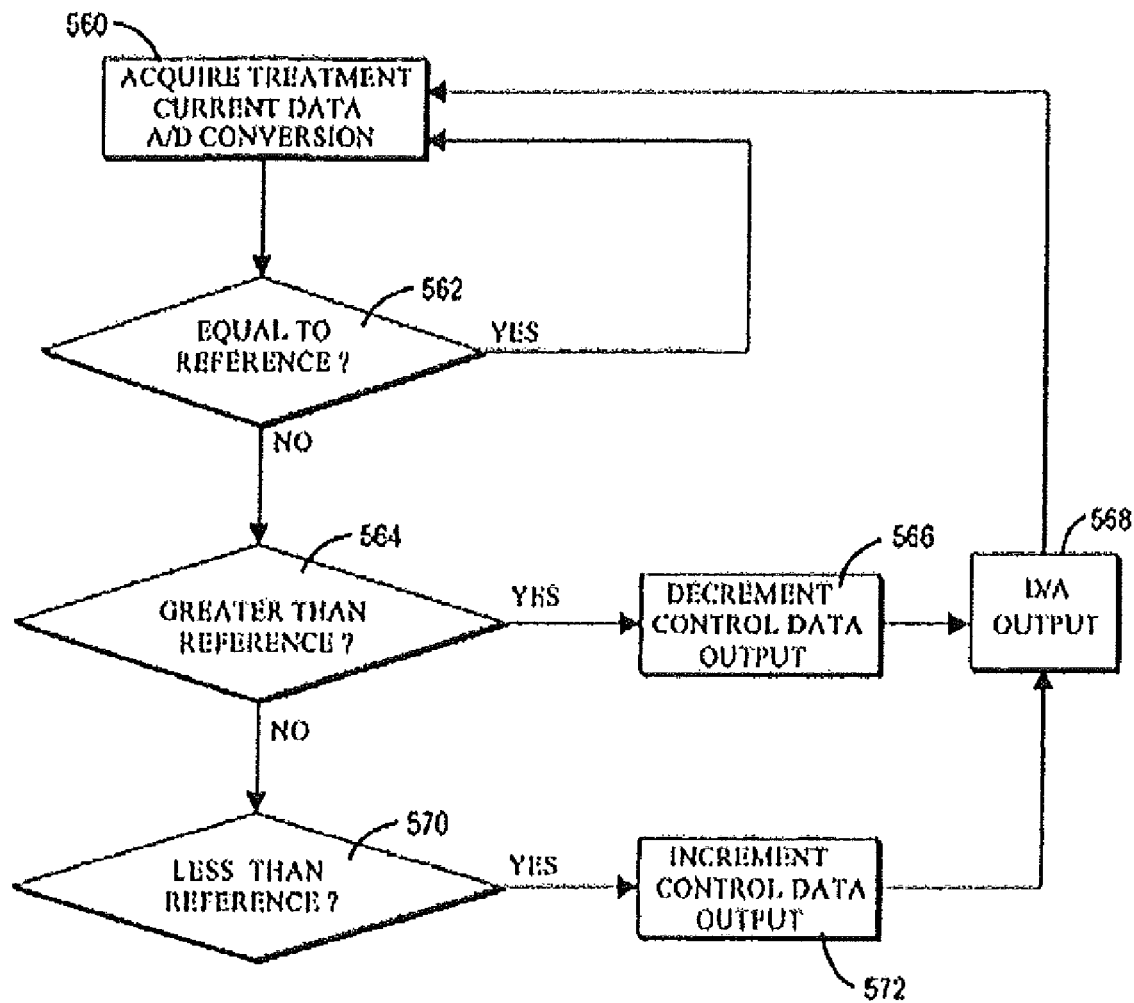

FIGS. 54A and 54B are flow charts illustrating an example operation of the device 10. At step 502, the distal portion 22 is engaged with the proximal portion 20 and power is turned on at step 504 when flag surface 202 completes the circuit of the power on/off switch 204. Processing circuitry 210 performs a battery test operation (step 506) to determine if the battery is okay. If not, the red LED is flashed for a predetermined period of time (e.g., one minute) (step 508) and the power is then switched off (step 510). If the battery is okay, processing circuitry 210 determines whether the number of uses of the proximal portion is less than a prescribed number of uses. If not, the red LED is flashed for a predetermined period of time (step 508) and the power is then switched off (step 510).

If the number of uses is less than the prescribed number, the green LED is flashed for a predetermined period of time (e.g., 10 seconds) (steps 514 and 516). Then, processing circuitry 210 begins to ramp up the treatment current (step 518). After the treatment current is ramped up, treatment begins. During treatment, processing circuitry 210 checks to determine whether the current is greater than 360 microamps. If not, the green LED is flashed (step 522) and the processing circuitry proceeds to the battery test operation (step 526). If the current is greater than 360 microamps, the green LED is kept on (step 524) before proceeding to the battery test operation.

If the battery fails the battery test operation, the red LED is flashed for a predetermined period of time (step 508) and then the power is switched off (step 510). If the battery is okay, processing circuitry 210 determines whether the treatment time period (e.g., 10 minutes) has elapsed. If not, control returns to step 520. If the treatment time period has elapsed, the ramp down of the treatment current begins and the green LED is kept on (step 530). When processing circuitry determines that the treatment current has decreased below 50 microamps (step 532), the red LED is turned on (step 534) and kept on for a predetermined period of time (e.g., one minute) (step 536). After this predetermined period of time, the red LED is turned off and the treatment number is incremented (step 538). After a predetermined period of time elapses (e.g., 4 hours) (step 540), the power is switched off (step 542).

FIG. 54B shows the treatment current servo loop which is executed almost continuously throughout the treatment. At step 560, the treatment current is sampled and converted from an analog value to a digital value. At step 562, a determination is made as to whether the sampled treatment current is equal to the reference treatment current for the current treatment. If so, control returns to step 560 where the treatment current is sampled again.

If the sampled treatment current is not equal to the reference current at step 562, a determination is made at step 564 as to whether the treatment current is greater than the reference current. If so, the control data output of the processing circuit is decreased and this output is converted from a digital value to an analog value at step 568. If the treatment is not greater than the reference current, a determination is made at step 570 as to whether the treatment current is less than the reference current. If so, the control data output of the processing circuit is increased and this output is converted from a digital value to an analog value at step 568.

When using the device 10, 110 hereof, the individual may apply the proximal portion 20, 120 in overlying relation to a finger, preferably the index finger, to be used to apply the medicament to the treatment site. Thus, the proximal portion 20, 120 is overlaid outside portions of the individuals' finger, straddling opposite sides of the first knuckle joint and secured thereto by straps 14, 114. The substrate 56, 156 is preferably prepackaged with a unit dose of medicament and supplied within the applicator head of the distal portion 22, 122. If not, the substrate may be applied to the recess 52, 152 of the applicator head on the distal portion 22, 122 of device 10, 110 with or without the medicament. Particularly, the substrate 56, 156 may be inserted into the recess 52, 152 such that the medicament or hydration material within the substrate makes electrical contact with the active electrode 54, 154. If the medicament is electrokinetically transportable and contained in the substrate, the device is ready for use upon connecting the distal portion 22, 122 with the proximal portion 20, 120. Alternatively, if the medicament is not permeated within the substrate, the individual may apply the medicament to the substrate or over the treatment site with suitable hydration material being applied as necessary or desired. Alternatively, if the medicament is provided in a releasable or rupturable capsule in the substrate, the individual may apply pressure to the substrate in the applicator head, rupturing the capsule, enabling the medicament from the capsule to permeate through the open interstices of the porous substrate. If the medicament is not iontophoretically transportable, the substrate may be hydrated by applying water or saline to the substrate.

Once the medicament is enabled for electrokinetic transport, the frustoconical section 40, 140 of the distal portion 22, 122 may be received about the individual's fingertip and contact made with the proximal portion by interconnecting the contacts 42, 142 and 44, 144. By applying the distal portion 22, 122 to the proximal portion 20, 120 and upon application of the applicator head to the treatment site, the electrical circuit is completed. Thus, the electrical circuit includes the active electrode 54, 154, the medicament or the hydration material used to electrokinetically transport the medicament, the treatment site, the individual's body, a return through the counter electrode, the power source and electronics to the active electrode 54, 154.

A treatment program may comprise one or more applications of medicament to a treatment site using the finger splint device described above. For example, a treatment program may comprise five applications of medicament. After each application of medicament, the disposable distal portion is removed from the proximal portion, and a new distal portion is connected to the (re-usable) proximal portion prior to the next application. In some instances, it may be desirable to vary the amount and/or efficacy of the medicament from one application to the next. For example, the amount of medicament used for the first application may be greater than the amount of medicament used for some subsequent application. Thus, a user of the finger splint device may purchase a treatment "package" comprising a plurality of distal portions (e.g., one or more having different amounts of medicament) to be used in a predetermined order. The distal portions may be configured electrically and/or mechanically in a manner that permits the processing circuitry of the proximal portion to detect which distal portion is connected thereto. By way of example, not limitation, the distal portion may include registers readable by the proximal portion. The registers may include information such as, but not limited to, the number of that distal portion in a particular order of use of distal portions. If the processing circuitry is programmed to track the medicament applications (e.g., by incrementing a hardware or software counter as each medicament application is completed), the proximal portion can inform the user (e.g., via the red LED or some other output device such as an LCD if provided) when a wrong distal portion (e.g., an out-of-sequence distal portion) is connected thereto. The detection of the distal portion connected thereto can also be used by the processing circuitry to set a timer fixing an amount of time that must pass before the next medicament application. The proximal portion is disabled to prohibit its use until this time period elapses.

In addition, it will be appreciated that the same proximal portion may be used with more than one type of distal portion. Thus, for example, the proximal portion may be selectively connected to one type of distal portion containing medicament for use in the treatment of herpes or to another type of distal portion containing medicament for use in the treatment of eczema. These distal portions may be configured electrically and/or mechanically so that the processing circuitry of the proximal portion can detect the type of distal portion connected thereto. In response to this detection, the proximal portion can, for example, use operating instructions suitable for a medicament application using the distal portion connected thereto.

The processing circuitry of the proximal portion may be programmed with (or have accessible thereto, e.g., via a memory) a plurality of different treatment current profiles (treatment current versus time), wherein the treatment current profile that is actually used depends upon the distal portion connected thereto. For example, in the case in which a treatment program comprises a plurality of applications of medicament, the treatment current profile for the first medicament application may be different than the treatment current profile for the last medicament application. Similarly, the treatment current profile for a herpes treatment program may be different than the treatment current profile for an eczema treatment program. Here again, the distal portions may be configured electrically and/or mechanically (e.g., using registers on the distal portion) in a manner that permits the processing circuitry of the proximal portion to detect which distal portion is connected thereto. In this way, the processing circuitry can use the treatment current profile appropriate for the proximal portion connected thereto.

Figure 48:
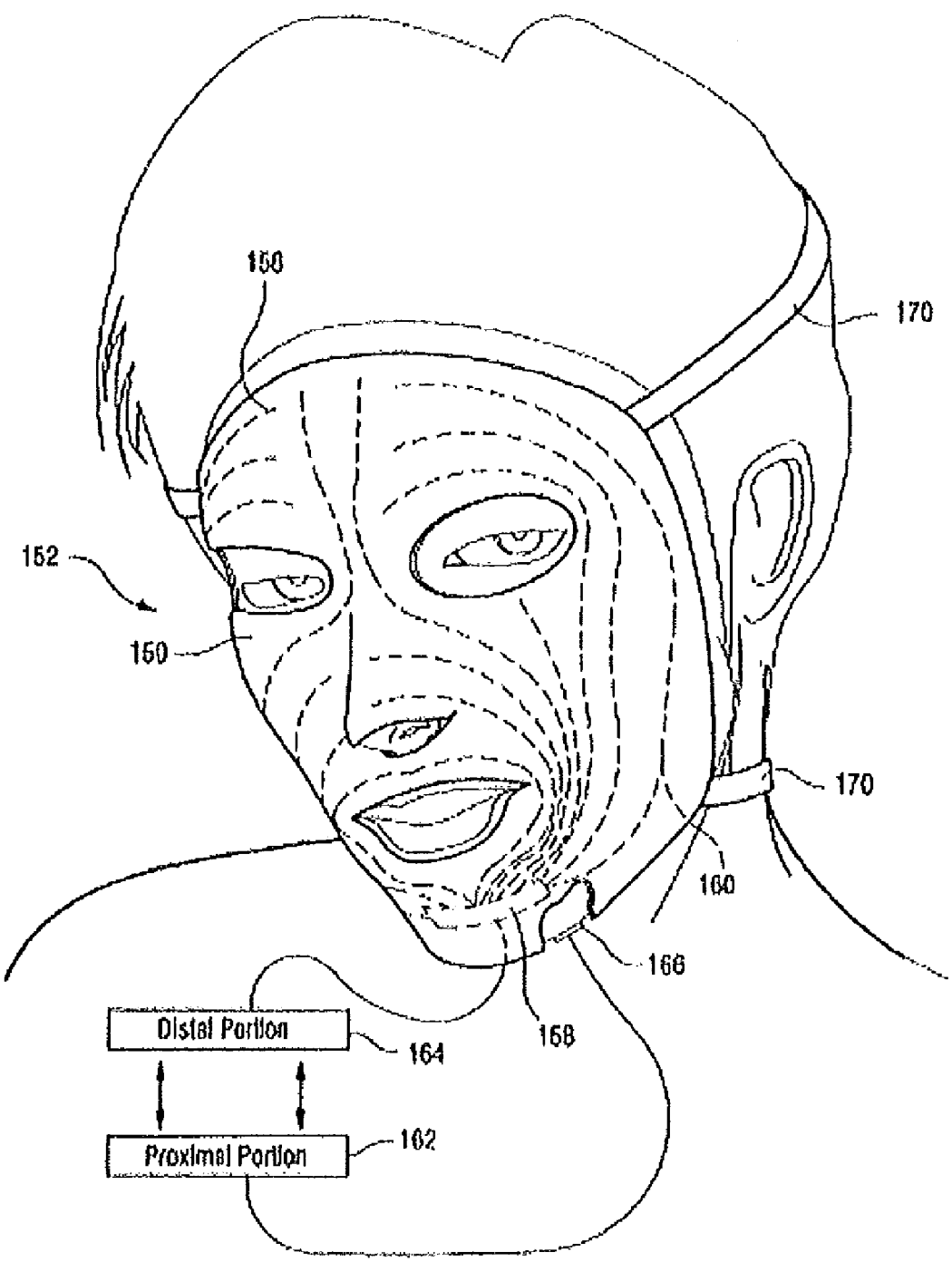
FIG. 48 is a perspective view of a face mask electrokinetic delivery device according to a further preferred embodiment hereof.

Referring now to FIG. 48, there is illustrated a further embodiment of a device for electrokinetically transporting a medicament into the skin and is particularly useful for applying medicament over large wide areas of an individual's face. For example, the illustrated mask, generally designated 150, may be used to treat dermatological conditions, e.g., eczema, psoriasis acne, boils, blemishes, provide anesthesia, or to provide dermal exfoliation. Treatment for wrinkles may be accomplished by delivering a modulator of collagen deposition, an organic nitrate, e.g., gallium nitrate. Treatment with metronidazole for rosecea is also beneficial. In this form of the present invention, there may be provided a full face mask 155 (FIG. 48) or a partial face mask 154 (FIG. 47). The face masks 152 and 154 may be formed of a matrix, e.g., a plastic or fabric material, which may be flexible for providing contact between an underlying medicament-carrying substrate 156. The underlying substrate 156 is formed of a porous material similarly as the substrates previously discussed. The porous material preferably has honeycomb cells which divide the substrate laterally to minimize lateral disbursement of the medicament contained in the substrate.

An electrical connector 158 carried by the mask connects an electrical power source to the mask via a plurality of independent or isolated electrical current channels or lead wires 160 carried by the matrix to form individual electrical conductive channels in the matrix. The current flowing through the channels is separately controlled to prevent tunneling of the current which would adversely affect the user.

The face mask is preferably portable, although it will be appreciated that the power supply can be provided either by an adapter plugged into a conventional electrical current supply or a "tabletop" or "portable" type unit with batteries that may be either disposable or rechargeable. Preferably, however, the power supply may be disposed in a housing portion 162 which corresponds in functionality to the electronics and power source contained in the proximal portion previously discussed. Additionally, another housing portion 164 is adapted for releasably coupling with the portion 162. As in the prior embodiments, connection of housing portions 162 and 164 activates the device. Portions 162 and 164 may serve, in effect, as an on/off switch for activating the device. As illustrated, the proximal portion 162 is electrically coupled to another portion of the face mask through a counter electrode 166. It will be appreciated, however, that the counter electrode 166 may be applied to other parts of the individual's body to complete the electrical circuit. For example, the counter electrode 166 may extend about the periphery of the mask 155 in contact with the individual's skin.

To utilize the electrokinetic device in the form of a face mask, the user dons the mask and attaches the mask to overlie the skin surface on the face by securing straps 170 about the back of the head. It will be appreciated that the substrate contains the medicament to be applied electrokinetically to the individual's face and thus lies in registration with the individual's face. Also note that the electrical conductors or electrodes 160 are closely spaced relative to one another to provide broad coverage, only a small number of the electrodes 160 being illustrated for clarity. Consequently, with the face mask applied as illustrated, the user couples the distal and proximal portions 164 and 162, respectively, to one another, completing the circuit from the power source, through the distal portion, the electrical conductors 160 which electrokinetically motivate the medicament into the facial skin, and the counter electrode for return to the power source. Alternatively, the coupling of the distal and proximal portions may enable the circuit, provided an on/off switch in the circuit is turned "on." A multi-channel system is provided in the face mask and particulars of the multi-channel system are disclosed in U.S. Pat. No. 5,160,316, issued Nov. 3, 1992, the disclosure of which is incorporated herein by reference.

Figure 49:
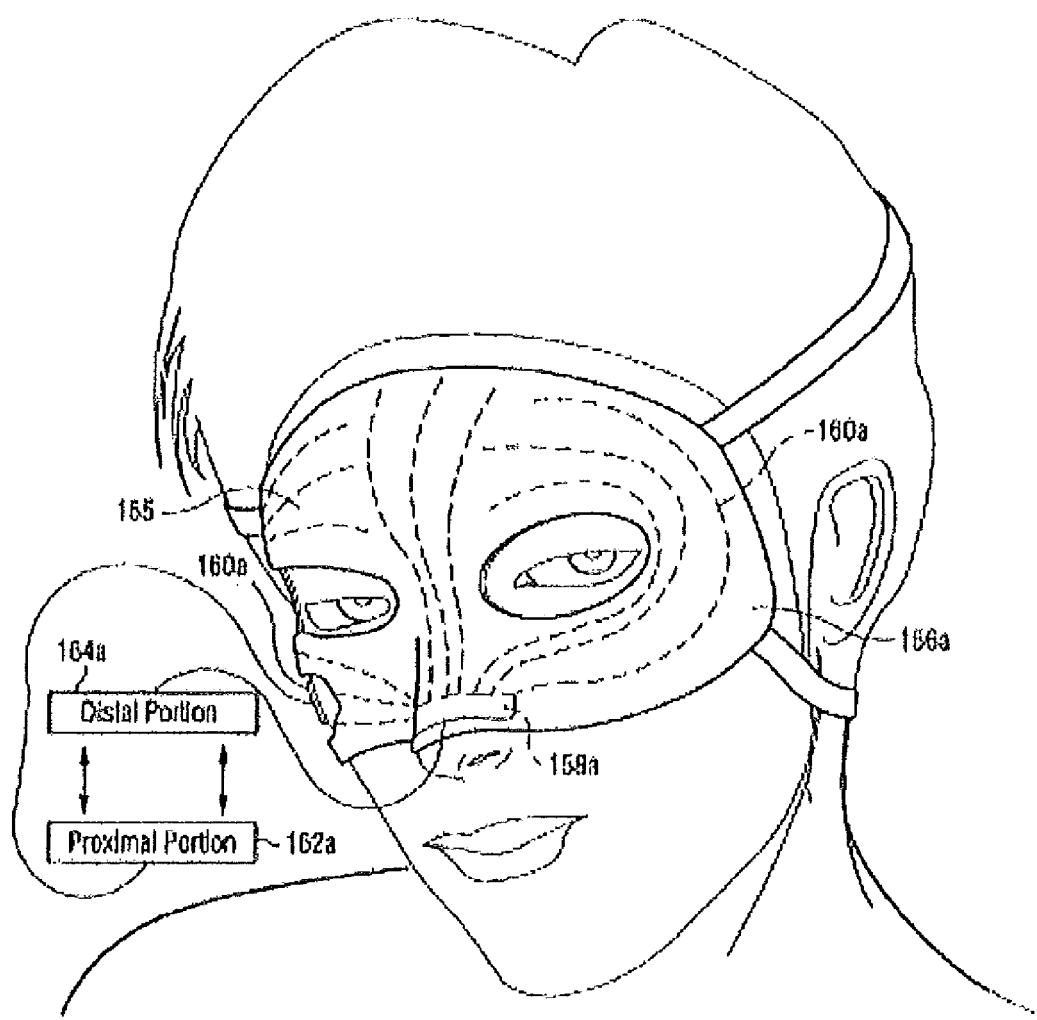
FIG. 49 is a view similar to FIG. 48 illustrating a further form of face mask.

In FIG. 49, like parts as in FIG. 48 are designated by like reference numerals followed by the suffix "a". The mask 155 is abbreviated from that illustrated in FIG. 48 and overlies facial regions about the eyes and nose of the individual and may cover substantially the entire forehead and portions of the cheeks or possibly include the neck or be a separate specific neck treatment applicator. The electromechanical elements of the embodiment are similar to those of FIG. 48 and include the underlying medicament carrying porous substrate 156*a*, electrical connector 158*a*, lead wires 160*a*, proximal and distal portions 162*a* and 164*a*, respectively, and a counter electrode 166*a*. The functionality of these elements is the same as in the previous embodiment.

Figure 50:
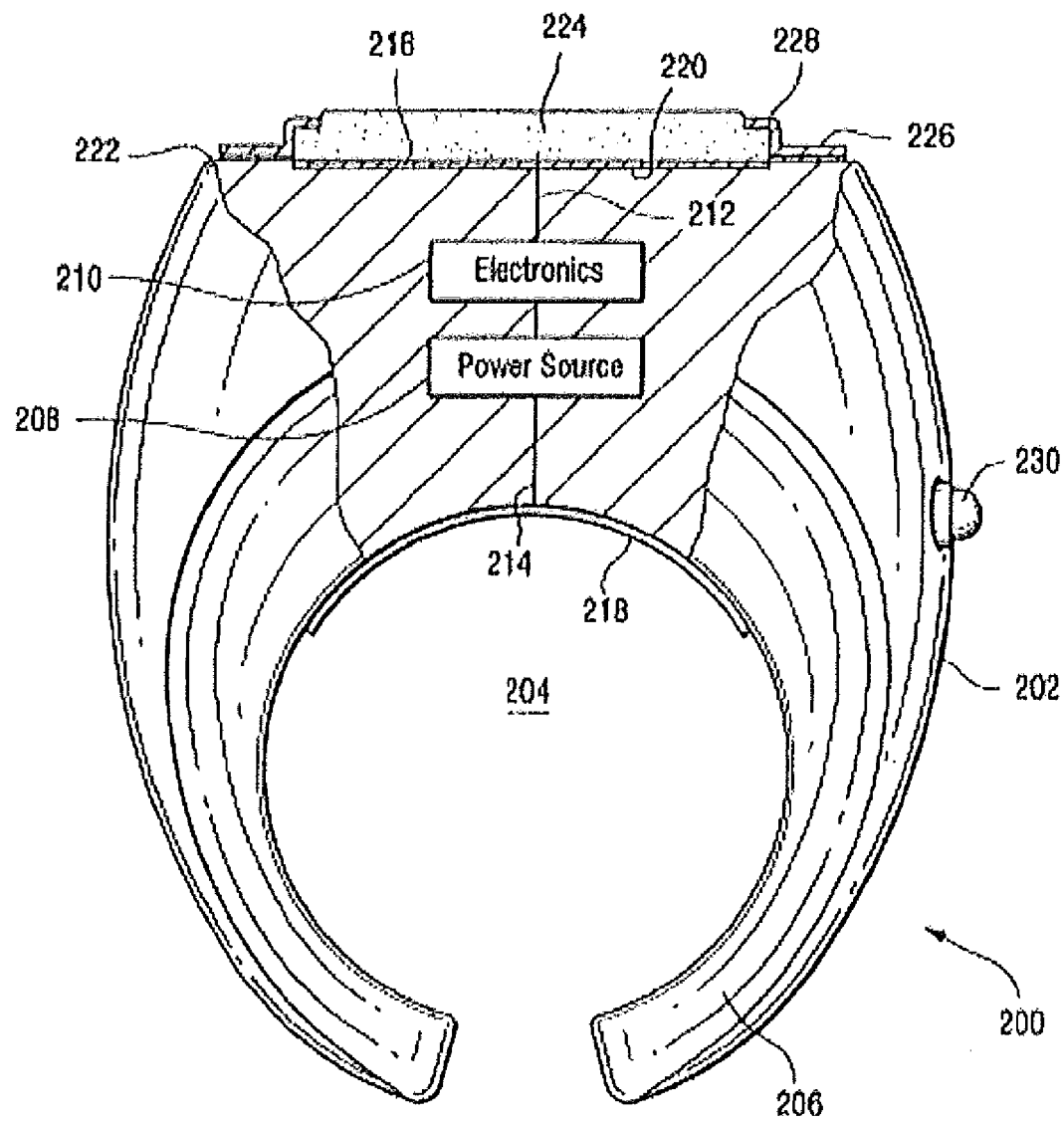
FIG. 50 is a side elevational view of a generally ring-shaped electrokinetic delivery device according to a still further preferred embodiment.
Figure 51:
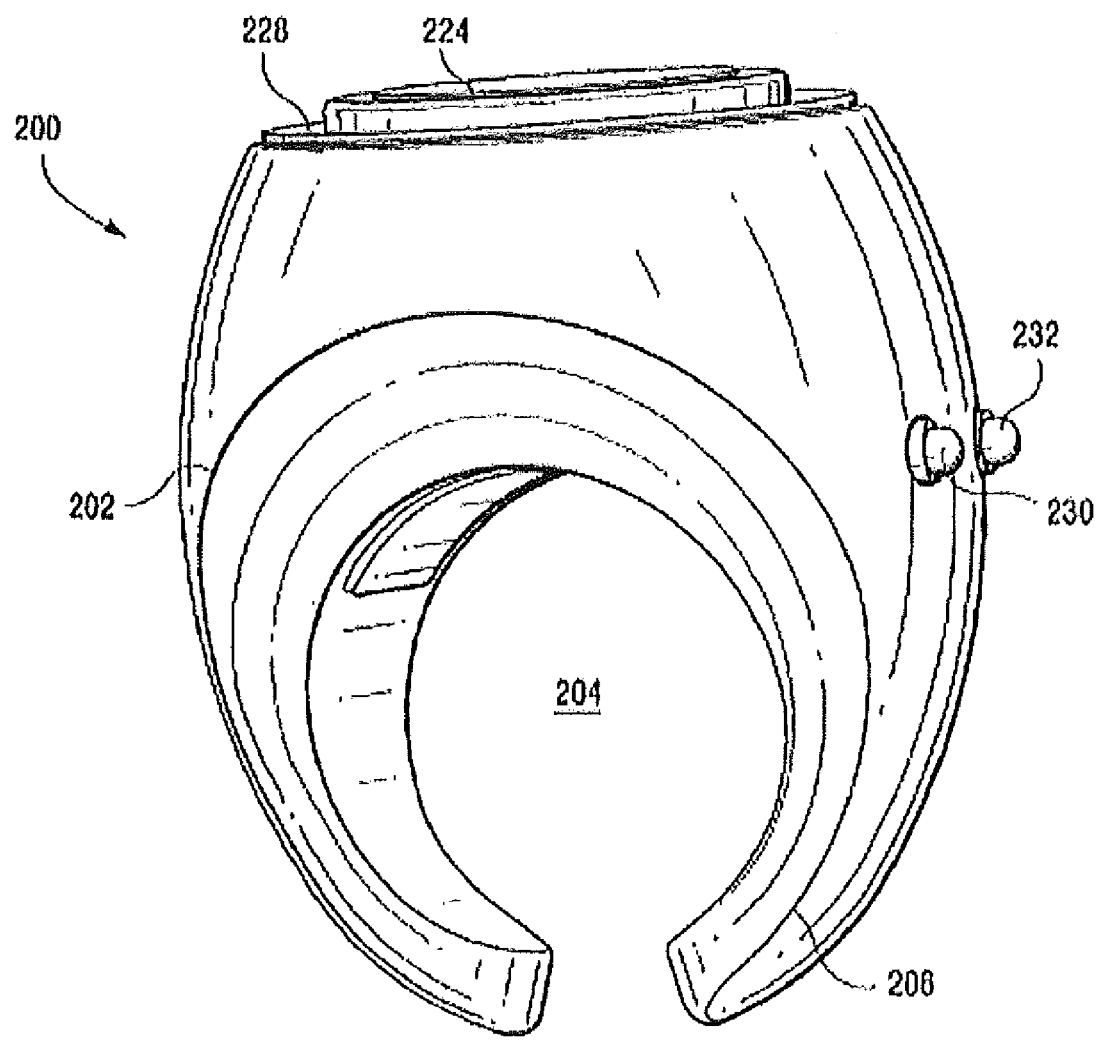
FIG. 51 is a perspective view thereof.

In a further embodiment of the present invention, there is illustrated with reference to FIGS. 50 and 51 a finger-mounted electrokinetic delivery device, generally designated 200, for the self-administration of a medicament and generally in the form of a ring carried by or applied about an individual's finger, preferably the index finger. Ring 200 includes a body 202. The generally ring-shaped body 202 has a through-opening 204 to receive the individual's finger and which opening is flanked by a pair of arcuate sections 206 which, together with a top portion of body 202, form a split ring for maintaining the device 200 on the individuals finger. It will be appreciated, of course, that body 202 may comprise a full circular ring without interruption, although the split ring form is believed preferable to provide flexibility and to accommodate different finger sizes.

The device 200 is self-contained and thus includes within the body 202 a power source 208 and electronics 210, as well as electrical connections 212 and 214 for electrically connecting the power source and electronics to an active electrode 216 and a counter electrode 218, respectively. The power source 208 and electronics 210 are similar to those described previously in the prior embodiments. The active electrode 216 may be in the form of a disk disposed in a recess 220, preferably circular, along the flat outer surface 222 of the ring-shaped body. Overlying the active electrode 216 and in contact therewith is a corresponding generally circular substrate 224 having the same attributes as the substrates 56, 156 previously described. Substrate 224 is maintained on the body 202 by a cap 226 secured to the flat outer surface 222 of the body and having marginal portions 228 overlying margins of the substrate 224. As in the prior embodiments, the substrate 224 contains a unit dose of medicament, and hydration material, if necessary, prepackaged with the device 200 for one-time disposable use. Alternatively, the substrate 224 may be separately packaged with a unit dose of medicament and hydration material, if necessary, apart from device 200 and applied to the device 200 and removed therefrom for each use whereby the device 200 may be reused with successive one-time use prepackaged substrates with medicament. As in previous embodiments, the outer contact surface of the substrate which is to be applied to the treatment site may be overlaid with a foil or releasable film, e.g., as illustrated in FIG. 42, to protect the contact surface and medicament prior to use.

The counter electrode 218 is preferably formed along the inside concave surface of the ring-shaped device 200. It will be appreciated that upon applying the ring-shaped body 202 to the individual's finger, the counter electrode 218 will automatically lie in electrical contact with the individual's finger. That is, the flexible side sections 206 of the device 200 bias the body 202 such that counter electrode 218 is pressed against the individual's finger. As illustrated in FIG. 51, the red and green LED's are indicated 230 and 232 along one side of the device to afford the indications described previously.

To use the device, the ring is disposed about the individual's finger. The device 200 may be provided with an on/off switch to enable the circuit between the active and counter electrodes and through the individuals body. Alternatively, the circuit may be activated in response to application of the ring-shaped body about the individual's finger. For example, the counter electrode 218 may be movable from an outwardly exposed position within the opening 204 to a position lying flush with the interior surface of the ring-shaped body 202 and which movement completes the internal circuit within the body 200 between the active and counter electrodes. With the ring mounted on an individual's finger, it will be appreciated that the substrate can be disposed over a treatment site which completes the electrical circuit through the individual's body and enables electrokinetic transport of the medicament into the treatment site. At the end of the treatment period, the device may be removed from the individual's finger and discarded in its entirety. Alternatively, the device is removed from the individual's finger and substrate may be removed from the ring and replaced by a fresh medicament-containing substrate for subsequent treatment. Of course, if reuse of the device with a fresh substrate is indicated, the on/off switch is placed in the "off" condition or the circuit may be interrupted automatically upon removal of the device from the individuals finger and return of the counter electrode 218 to its projecting position within the opening 204.

Figure 52:
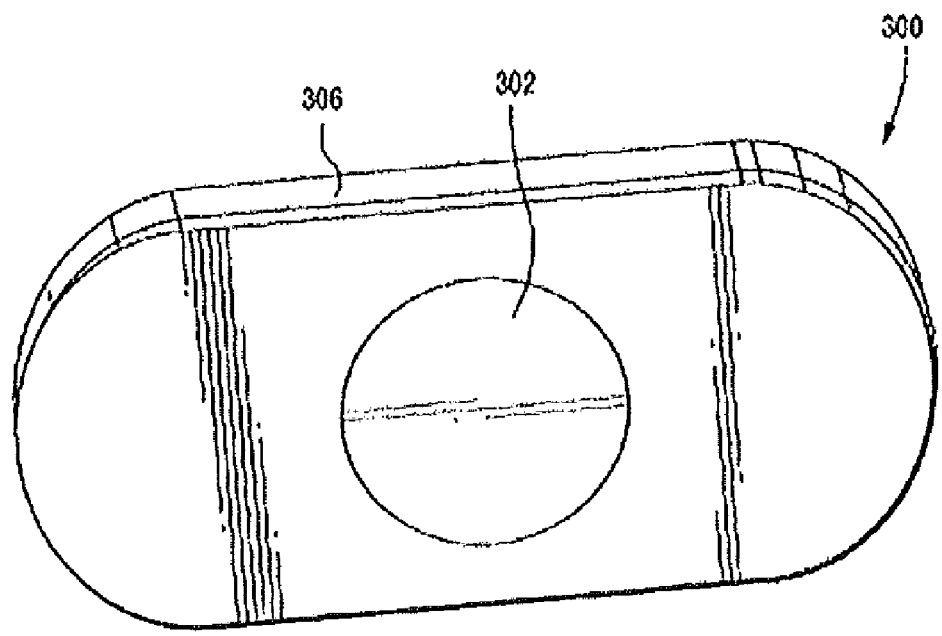
FIGS. 52 and 53 are a bottom view and a side perspective view, respectively, of a patch applicator.
Figure 53:
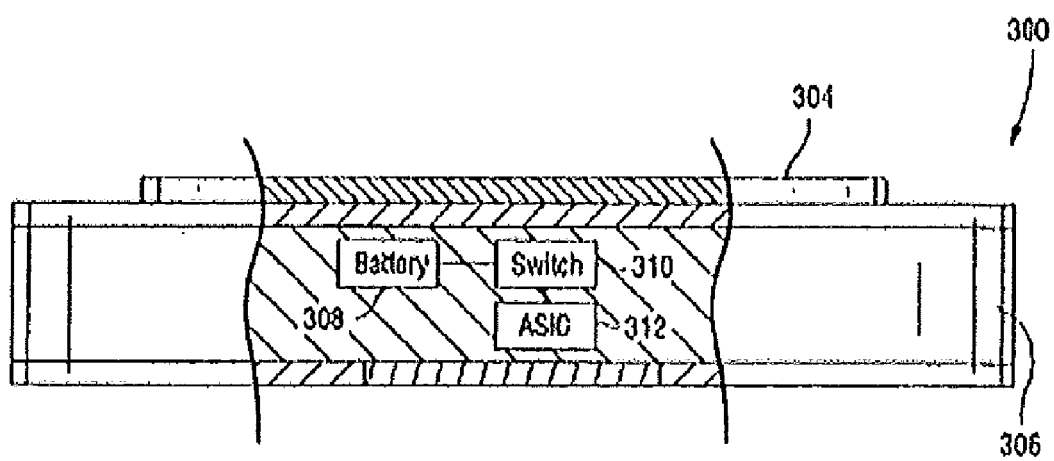

FIGS. 52 and 53 are a bottom view and a side perspective view, respectively, of a patch applicator 300. The patch applicator is intended for limited (one- or two-time) use, after which it is disposed. Patch applicator 300 includes an active electrode 302 and a counter electrode 304. Embedded within the applicator body 306 are a battery 308, a switch 310 and an ASIC 312. Optionally, an LED may be provided. Switch 310 may be a touch-sensitive switch (e.g., membrane) so that the user's finger applied to the counter electrode 304 to hold the applicator in place at the treatment site activates the patch applicator. ASIC 312 controls the treatment current, treatment time, etc. as appropriate for the treatment for which the patch applicator is intended. The optional LED may be illuminated to provide a visual indication that the patch applicator is activated. Alternatively, a non-ultrasound generated vibration can be added or used in lieu of the LED to indicate a working status of the device and that the device lies in a closed current loop via the individuals body surface.

While the invention has been described in connection with what is presently considered to be the most practical and preferred embodiment, it is to be understood that invention is not to be limited to the disclosed embodiment, but on the contrary, is intended to cover various the modifications and equivalent arrangements included within the spirit and scope of the appended claims.

What is claimed is:

1. A method for delivering a substance to an infected nail of an individual, comprising:
    applying a device to at least one infected nail of an individual, wherein the device includes at least one active electrode and at least one counter electrode, wherein the at least one counter electrode is in contact with the individual, and wherein the device is connected to at least one power source;
    disposing a medicament between the at least one active electrode and the at least one infected nail;
    applying a salt solution to the at least one infected nail prior to delivery of the medicament; and
    providing an electrical current from the power source to the at least one active electrode to facilitate delivery of the medicament into the region of the at least one infected nail.

2. The method of claim 1, wherein the medicament is an anti-fungal.
3. The method of claim 1, wherein the medicament is contained within a pad.
4. The method of claim 1, wherein the medicament comprises a conductive fluid.
5. The method of claim 1, wherein the nail is a toenail.
6. The method of claim 1, wherein the medicament is delivered directly into the nail bed.
7. The method of claim 1, wherein the medicament is delivered into the nail bed and surrounding nail tissue.
8. A system for delivering a substance to an infected nail of an individual, comprising:
    a power source;
    a device connected to the power source, the device comprising at least one active electrode and at least one counter electrode, wherein the at least one counter electrode is in contact with the individual;
    a medicament disposed between the at least one active electrode of the device and the infected nail of the individual;
    wherein the infected nail is first treated with a salt solution, and subsequently an electrical current is provided from the power source to the at least one active electrode to electrokinetically drive the medicament into the salt-treated region of the infected nail.
9. The system of claim 8, wherein the substance is delivered directly into the salt-treated nail bed.
10. The system of claim 8, wherein the substance is contained within a pad.
11. The system of claim 8, wherein the substance comprises a conductive fluid.
12. The system of claim 8, wherein the nail is a toenail.
13. The system of claim 9, wherein the substance is an anti-fungal agent.
14. The system of claim 8, wherein the substance is delivered into the salt-treated nail bed and surrounding salt-treated nail tissue.
15. A device for delivery of a substance to a treatment site on an individual, comprising:
    a power supply;
    an applicator including a first electrode and a pad for containing a substance, wherein the first electrode is connected to the power supply and the pad is positioned on a first side of the applicator with the first electrode overlying the pad;
    a second electrode connected to the power supply;
    wherein, after application of a salt solution to the treatment site, the applicator is applied against the treatment site and the second electrode is placed in contact with a portion of the individual's body, an electrical circuit is completed between the first electrode through the treatment site, the portion of the individual's body and the second electrode for electrokinetically driving the substance into the treatment site.
16. The device of claim 15, wherein the substance is an anti-fungal agent.
17. The device of claim 15, wherein the substance comprises a conductive fluid.
18. The device of claim 15, wherein the treatment site is a nail.
19. The device of claim 18, wherein the nail is a toenail.

* * * * *